(12) United States Patent
Corre et al.

(10) Patent No.: US 10,731,137 B2
(45) Date of Patent: Aug. 4, 2020

(54) LACTALDEHYDE REDUCTASES FOR THE PRODUCTION OF 1,2-PROPANEDIOL

(71) Applicant: METABOLIC EXPLORER, Saint Beauzire (FR)

(72) Inventors: Gwénaëlle Corre, Saint Beauzire (FR); Pascale Aliprandi, Surat (FR)

(73) Assignee: METABOLIC EXPLORER, Saint Beauzire (FR)

( * ) Notice: Subject to any disclaimer, the term of this patent is extended or adjusted under 35 U.S.C. 154(b) by 38 days.

(21) Appl. No.: 15/758,885

(22) PCT Filed: Sep. 10, 2015

(86) PCT No.: PCT/IB2015/001890
§ 371 (c)(1),
(2) Date: Mar. 9, 2018

(87) PCT Pub. No.: WO2017/042602
PCT Pub. Date: Mar. 16, 2017

(65) Prior Publication Data
US 2018/0282706 A1     Oct. 4, 2018

(51) Int. Cl.
*C12N 9/04* (2006.01)
*C12P 7/18* (2006.01)
*C12R 1/19* (2006.01)

(52) U.S. Cl.
CPC .............. *C12N 9/0006* (2013.01); *C12P 7/18* (2013.01); *C12R 1/19* (2013.01); *C12Y 101/01* (2013.01); *C12Y 101/01077* (2013.01); *C12Y 101/01283* (2013.01); *C12Y 208/03017* (2013.01); *C12Y 402/03003* (2013.01); *C12Y 404/01005* (2013.01); *C12Y 501/02001* (2013.01)

(58) Field of Classification Search
CPC .............................. C12N 9/0008; C12N 9/04
See application file for complete search history.

(56) References Cited

U.S. PATENT DOCUMENTS 8,969,053 B2 * 3/2015 Voelker ................ C12N 9/0006
435/148
2014/0134690 A1 5/2014 Yan et al.

FOREIGN PATENT DOCUMENTS

| WO | WO 2008/116848 A1 | 10/2008 |
| WO | WO 2011/012693 A1 | 2/2011 |
| WO | WO 2011/012697 A2 | 2/2011 |
| WO | WO 2014/062993 A1 | 4/2014 |

OTHER PUBLICATIONS

Saxena et al. 2010; Microbial production and applications of 1, 2-propanediol. Indian J. Microbiol. 50(1): 2-11.*

Altaras et al., "Enhanced Production of (R)-1,2-Propanediol by Metabolically Engineered *Escherichia coli*," Biotechnol. Prog., vol. 16, No. 6, 2000, pp. 940-946.

Altaras et al., "Metabolic Engineering of a 1,2-Propanediol Pathway in *Escherichia coli*," Applied and Environmental Microbiology, vol. 65, No. 3, Mar. 1999, pp. 1180-1185.

Altschul et al., "Basic Local Alignment Search Tool," J. Mol. Biol., vol. 215, 1990, pp. 403-410.

Author Unknown, "*Escherichia coli* ADH2_ECOLI 1, 3-propanediol oxidoreductase protein," Database Geneseq, ID AZE73396, XP-002757297, Mar. 17, 2011, 1 page.

Badía et al., "Fermentation Mechanism of Fucose and Rhamnose in *Salmonella typhimurium* and Klebsiella pneumoniae," Journal of Bacteriology, vol. 161, No. 1, Jan. 1985, pp. 435-437.

Bennett et al., "Microbial Formation, Biotechnological Production and Applications of 1,2-Propanediol," Appl. Microbiol. Biotechnol., vol. 55, 2001, pp. 1-9.

Berríos-Rivera et al., "The Effect of Carbon Sources and Lactate Dehydrogenase Deletion on 1,2-propanediolPproduction in *Escherichia coli*," J. Ind. Microbiol. Biotechnol., vol. 30, 2003, pp. 34-40.

Blikstad et al., "Functional Characterization of a Stereospecific Diol Dehydrogenase, FucO, from *Escherichia coli*: Substrate Specificity, pH Dependence . . . Solvent Viscosity," Journal of Molecular Catalysis B: Enzymatic, vol. 66, 2010 (published on web May 15, 2010), pp. 148-155.

Bocanegra et al., "Creation of an NADP-Dependent Pyruvate Dehydrogenase Multienzyme Complex by Protein Engineering," Biochemistry, vol. 32, No. 11, Mar. 23, 1993, pp. 2737-2740.

Boronat et al., "Rhamnose-Induced Propanediol Oxidoreductase in *Escherichia coli*: Purification, Properties, and Comparison with the Fucose-Induced Enzyme," Journal of Bacteriology, vol. 140, No. 2, Nov. 1979, pp. 320-326.

Bradford, "A Rapid and Sensitive Method for the Quantitization of Microgram Quantities of Protein Utilizing the Principle of Protein-Dye Binding," Analytical Biochemistry, vol. 72, 1976, pp. 248-254.

Cabiscol et al., "Inactivation of Propanediol Oxidoreductase of *Escherichia coli* by Metal-Catalyzed Oxidation," Biochimica et Biophysica Acta, vol. 1118, 1992, pp. 155-160.

Cameron et al., "Metabolic Engineering of Propanediol Pathways," Biotechnol. Prog., vol. 14, 1998, pp. 116-125.

Cantwell et al., "Lactate Racemase. Direct Evidenec for an α-Carbonyl Intermediate," Biochemistry, vol. 13, No. 2, 1974, pp. 287-291.

Carrier et al., "Library of Synthetic 5' Secondary Structures to Manipulate mRNA Stability in *Escherichia coli*," Biotechnol. Prog., vol. 15, 1999, pp. 58-64.

Centeno-Leija et al., "Metabolic and Transcriptional Response of *Escherichia coli* with a NADP+-dependent Glyceraldheyde 3-Phosphate Dehydrogenase from *Streptococcus mutans*," Antonie van Leeuwenhoek, vol. 104, No. 6, 2013 (published on web Aug. 29, 2013), 12 pages.

(Continued)

*Primary Examiner* — Karen Cochrane Carlson
(74) *Attorney, Agent, or Firm* — Birch, Stewart, Kolasch & Birch, LLP

(57) ABSTRACT

The present invention relates to new lactaldehyde reductase (LAR) enzymes useful for the production of 1,2-propanediol and to microorganisms overexpressing said enzymes. The invention also relates to a method for producing 1,2-propanediol by converting lactaldehyde into 1,2-propanediol with said enzymes.

5 Claims, 2 Drawing Sheets

Figure 1:
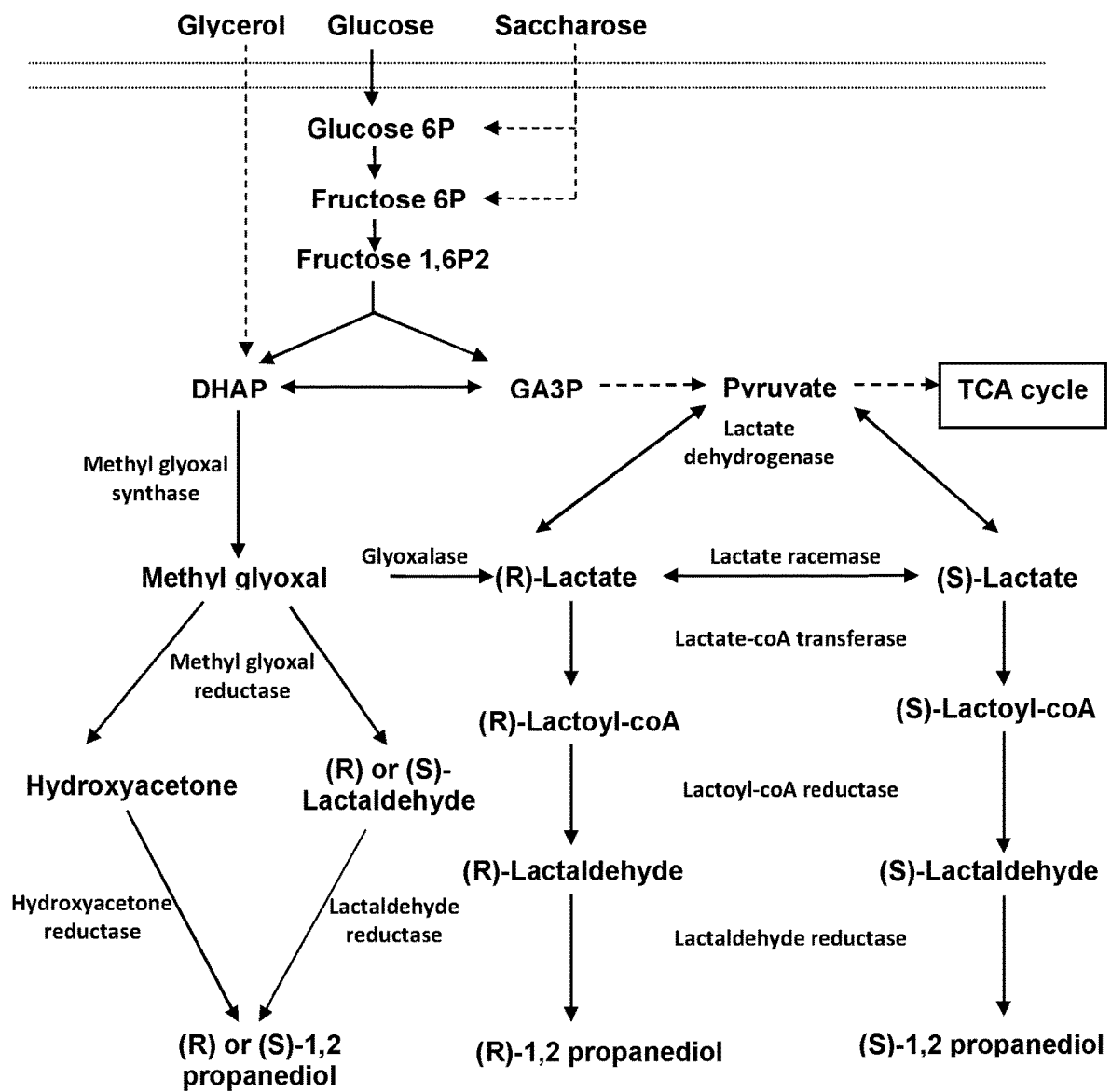

Specification includes a Sequence Listing.

(56) References Cited

OTHER PUBLICATIONS

Cooper et al., "Metabolism of Methylglyoxal in Microorganisms," Ann. Rev. Microbiol., vol. 38, 1984, pp. 49-68.
Davis et al., "Characterizing the Native Codon Usages of a Genome: An Axis Projection Approach," Mol. Biol. Evol., vol. 28, No. 1, 2011 (Advance Access punlication Aug. 2, 2010), pp. 211-221.
Deml et al., "Multiple Effects of Codon Usage Optimization on Expression and Immunogenicity of DNA Candidate Vaccines Encoding the Human Immunodeficiency Virus Type 1 Gag Protein," Journal of Virology, vol. 75, No. 22, Nov. 2001, pp. 10991-11001.
Desguin et al., "Enantioselective Regulation of Lactate Racemization by LarR in Lactobacillus plantarum," J. Bacteriol., 2014 (published on web Oct. 27, 2014), pp. 1-33 (41 pages total).
Desguin et al., "Lactate Racemase is a Nickel-Dependent Enzyme Activated by a Widespread Maturation System," Nature Communications, Apr. 7, 2014, pp. 1-12.
Goffin et al., "Lactate Racemization as a Rescue Pathway for Supplying D-Lactate to the Cell Wall Biosynthesis Machinery in Lactobacillus plantarum," Journal of Bacteriology, vol. 187, No. 19, Oct. 2005, pp. 6750-6761.
Graf et al., "Concerted Action of Multiple cis-Acting Sequences Is Required for Rev Dependence of Late Human Immunodeficiency Virus Type 1 Gene Expression," Journal of Virology, vol. 74, No. 22, Nov. 2000, pp. 10822-10826.
Hino et al., "Presence of Lactate Dehydrogenase and Lactate Racemase in Megasphaera elsdenii Grown on Glucose or Lactate," Applied and Environmental Microbiology, vol. 59, No. 1, Jan. 1993, pp. 255-259.
Hiyama et al., "Purification and Properties of Lactate Racemase from Lactobacillus sake," Journal of Biochemistry, vol. 64, No. 1, 1968, pp. 99-107.
Huang et al., "Characterization of Methylglyoxal Synthase from Clostridium acetobutylicum ATCC 824 and Its Use in the Formation of 1,2-Propanediol," Applied and Environmental Microbiology, vol. 65, No. 7, Jul. 1999, pp. 3244-3247.
Kovach et al., "Four New Derivatives of the Broad-Host-Range Cloning Vector pBBR1MCS, Carrying Different Antibiotic-Resistance Cassettes," Gene., vol. 166, 1995, pp. 175-176.
Lee et al., "Control of Substrate Access to the Active Site in Methane Monooxygenase," Nature, vol. 494, Feb. 21, 2013, pp. 380-384.
Li et al., "Engineering a Cyanobacterium as the Catalyst for the Photosynthetic Conversaion of $CO_2$ to 1,2-Propanediol," Microbiol Cell Factories, vol. 12, No. 4, 2013, pp. 1-9.
Lim et al., "Amplification of the NADPH-Related Genes zwf and gnd for the Oddball Biosynthesis of PHB in an *E. coli* Transformant Harboring a Cloned phbCAB Operon," Journal of Bioscience and Bioengineering, vol. 93, No. 6, 2002, pp. 543-549.
Marbaix et al., "Extremely Conserved ATP- or ADP-dependent Enzymatic System for Nicotinamide Nucleotide Repair," Journal of Biological Chemistry, vol. 286, No. 48, Dec. 2, 2011, pp. 41246-41252.
Misra et al., "Glyoxalase III from *Escherichia coli*: a Single Novel Enzyme for the Conversion of Methylglyoxal into D-Lactate Without Reduced Glutathione," Biochem. J., vol. 305, 1995, pp. 999-1003.
Needleman et al., "A General Method Applicable to the Search for Similarities in the Amino Acid Sequence of Two Proteins," J. Mol. Biol., vol. 48, 1970, pp. 443-453.
Niu et al., "Stereospecific Microbial Conversion of Lactic Acid into 1,2-Propanediol," ACS Synthetic Biology, vol. 4, No. 4, 2015 (published on web Jul. 3, 2014), pp. 378-382 (15 pages total).
Pepple et al., "Hydroxylamine-Dependent $^{18}O$ Exchange of the α-Hydroxyl of Lactic Acid," Biochimica et Biophysica Acta, vol. 429, 1976, pp. 1036-1040.
Salis, "The Ribosome Binding Site Calculator," Methods in Enzymology, vol. 498, 2011, pp. 19-42.
Sambrook et al., "Molecular Cloning: A Laboratory Manual," Cold Spring Harbor Laboratory Press, Fourth Edition, vol. 1, 2012, pp. (i)-(xxxiii) (34 pages total).
Segel, "Enzyme Kinetics," John Wiley & Sons, 1993, pp. 44-55, 100-113.
Studier et al., "Use of T7 RNA Polymerase to Direct Expression of Cloned Genes," Methods in Enzymology, vol. 185, 1990, pp. 60-89.
Sulzenbacher et al., "Crystal Structure of *E. coli* Alcohol Dehydrogenase YqhD: Evidence of a Covalently Modified NADP Coenzyme," J. Mol. Biol., vol. 342, 2004, pp. 489-502.

* cited by examiner

SEQUENCE LISTING

<160> NUMBER OF SEQ ID NOS: 64

<210> SEQ ID NO 1
<211> LENGTH: 382
<212> TYPE: PRT
<213> ORGANISM: Escherichia coli
<220> FEATURE:
<221> NAME/KEY: misc_feature
<223> OTHER INFORMATION: FucO amino acid sequence

<400> SEQUENCE: 1

Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
        20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
 50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
370                 375                 380

<210> SEQ ID NO 2
<211> LENGTH: 1149
<212> TYPE: DNA
<213> ORGANISM: Escherichia coli
<220> FEATURE:
<221> NAME/KEY: misc_feature
<223> OTHER INFORMATION: FucO nucleotide sequence

<400> SEQUENCE: 2

```
atggctaaca gaatgattct gaacgaaacg gcatggtttg gtcggggtgc tgttggggct      60
ttaaccgatg aggtgaaacg ccgtggttat cagaaggcgc tgatcgtcac cgataaaacg     120
ctggtgcaat gcggcgtggt ggcgaaagtg accgataaga tggatgctgc agggctggca     180
tgggcgattt acgacggcgt agtgcccaac ccaacaatta ctgtcgtcaa agaagggctc     240
ggtgtattcc agaatagcgg cgcggattac ctgatcgcta ttggtggtgg ttctccacag     300
gatacttgta aagcgattgg cattatcagc aacaacccgg agtttgccga tgtgcgtagc     360
ctggaagggc tttccccgac caataaaccc agtgtaccga ttctggcaat tcctaccaca     420
gcaggtactg cggcagaagt gaccattaac tacgtgatca ctgacgaaga gaaacggcgc     480
aagtttgttt gcgttgatcc gcatgatatc ccgcaggtgg cgtttattga cgctgacatg     540
atggatggta tgcctccagc gctgaaagct gcgacgggtg tcgatgcgct cactcatgct     600
attgagggt atattacccg tggcgcgtgg gcgctaaccg atgcactgca cattaaagcg     660
attgaaatca ttgctggggc gctgcgagga tcggttgctg gtgataagga tgccggagaa     720
gaaatggcgc tcgggcagta tgttgcgggt atgggcttct cgaatgttgg gttagggttg     780
gtgcatggta tggcgcatcc actgggcgcg ttttataaca ctccacacgg tgttgcgaac     840
gccatcctgt taccgcatgt catgcgttat aacgctgact ttaccggtga agtaccgc      900
gatatcgcgc gcgttatggg cgtgaaagtg gaaggtatga gcctggaaga ggcgcgtaat     960
gccgctgttg aagcggtgtt tgctctcaac cgtgatgtcg gtattccgcc acatttgcgt    1020
gatgttggtg tacgcaagga agacattccg gcactggcgc aggcggcact ggatgatgtt    1080
tgtaccggtg gcaacccgcg tgaagcaacg cttgaggata ttgtagagct ttaccatacc    1140
gcctggtaa                                                             1149
```

<210> SEQ ID NO 3
<211> LENGTH: 383
<212> TYPE: PRT
<213> ORGANISM: Escherichia coli
<220> FEATURE:
<221> NAME/KEY: misc_feature
<223> OTHER INFORMATION: YiaY amino acid sequence

<400> SEQUENCE: 3

```
Met Ala Ala Ser Thr Phe Phe Ile Pro Ser Val Asn Val Ile Gly Ala
1               5                   10                  15

Asp Ser Leu Thr Asp Ala Met Asn Met Met Ala Asp Tyr Gly Phe Thr
            20                  25                  30

Arg Thr Leu Ile Val Thr Asp Asn Met Leu Thr Lys Leu Gly Met Ala
        35                  40                  45

Gly Asp Val Gln Lys Ala Leu Glu Glu Arg Asn Ile Phe Ser Val Ile
    50                  55                  60

Tyr Asp Gly Thr Gln Pro Asn Pro Thr Thr Glu Asn Val Ala Ala Gly
65                  70                  75                  80

Leu Lys Leu Leu Lys Glu Asn Asn Cys Asp Ser Val Ile Ser Leu Gly
                85                  90                  95

Gly Gly Ser Pro His Asp Cys Ala Lys Gly Ile Ala Leu Val Ala Ala
            100                 105                 110

Asn Gly Gly Asp Ile Arg Asp Tyr Glu Gly Val Asp Arg Ser Ala Lys
        115                 120                 125

Pro Gln Leu Pro Met Ile Ala Ile Asn Thr Thr Ala Gly Thr Ala Ser
    130                 135                 140
```

```
Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
            180                 185                 190

Met Asp Ala Leu Thr His Ala Ile Glu Ala Tyr Val Ser Ile Ala Ala
        195                 200                 205

Thr Pro Ile Thr Asp Ala Cys Ala Leu Lys Ala Val Thr Met Ile Ala
    210                 215                 220

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Phe
            260                 265                 270

Tyr Asn Leu Pro His Gly Val Cys Asn Ala Val Leu Leu Pro His Val
        275                 280                 285

Gln Val Phe Asn Ser Lys Val Ala Ala Ala Arg Leu Arg Asp Cys Ala
    290                 295                 300

Ala Ala Met Gly Val Asn Val Thr Gly Lys Asn Asp Ala Glu Gly Ala
305                 310                 315                 320

Glu Ala Cys Ile Asn Ala Ile Arg Glu Leu Ala Lys Lys Val Asp Ile
                325                 330                 335

Pro Ala Gly Leu Arg Asp Leu Asn Val Lys Glu Glu Asp Phe Ala Val
            340                 345                 350

Leu Ala Thr Asn Ala Leu Lys Asp Ala Cys Gly Phe Thr Asn Pro Ile
        355                 360                 365

Gln Ala Thr His Glu Glu Ile Val Ala Ile Tyr Arg Ala Ala Met
    370                 375                 380

<210> SEQ ID NO 4
<211> LENGTH: 1077
<212> TYPE: DNA
<213> ORGANISM: Escherichia coli
<220> FEATURE:
<221> NAME/KEY: misc_feature
<223> OTHER INFORMATION: YiaY nucleotide sequence

<400> SEQUENCE: 4
atggcagatt atggatttac ccgtacctta attgtcactg acaatatgtt aacgaaatta      60
ggtatggcgg gcgatgtgca aaaagcactg aagaacgca atattttag cgttatttat      120 gatggcaccc aacctaaccc caccacggaa aacgtcgccg caggtttgaa attacttaaa      180
gagaataatt gcgatagcgt gatctcctta ggcggtggtt ctccacacga ctgcgcaaaa      240
ggtattgcgc tggtggcagc caatggcggc gatattgcg attacgaagg cgttgaccgc      300
tctgcaaaac cgcagctgcc gatgatcgcc atcaatacca cggcgggtac ggcctctgaa      360
atgacccgtt tctgcatcat cactgacgaa gcgcgtcata tcaaaatggc gattgttgat      420
aaacatgtca ctccgctgct ttctgtcaat gactcctctc tgatgattgg tatgccgaag      480
tcactgaccg ccgcaacggg tatggatgcc ttaacgcacg ctatcgaagc atatgtttct      540
attgccgcca cgccgatcac tgacgcttgt gcactgaaag ccgtgaccat gattgccgaa      600
aacctgccgt tagccgttga agatggcagt aatgcgaaag cgcgtgaagc aatggcttat      660
```

```
gcccagttcc tcgccggtat ggcgttcaat aatgcttctc tgggttatgt tcatgcgatg    720
gcgcaccagc tgggcggttt ctacaacctg ccacacggtg tatgtaacgc cgttttgctg    780
ccgcacgttc aggtattcaa cagcaaagtc gccgctgcac gtctgcgtga ctgtgccgct    840
gcaatgggcg tgaacgtgac aggtaaaaac gacgcggaag gtgctgaagc ctgcattaac    900
gccatccgtg aactggcgaa gaaagtggat atcccggcag gcctacgcga cctgaacgtg    960
aaagaagaag atttcgcggt attggcgact aatgccctga agatgcctg tggctttact    1020 aacccgatcc aggcaactca cgaagaaatt gtggcgattt atcgcgcagc gatgtaa     1077
```

<210> SEQ ID NO 5
<211> LENGTH: 367
<212> TYPE: PRT
<213> ORGANISM: Escherichia coli
<220> FEATURE:
<221> NAME/KEY: misc_feature
<223> OTHER INFORMATION: GldA amino acid sequence

<400> SEQUENCE: 5

```
Met Asp Arg Ile Ile Gln Ser Pro Gly Lys Tyr Ile Gln Gly Ala Asp
 1               5                  10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285
```

| Pro | Val | Glu | Glu | Ile | Glu | Thr | Val | Ala | Ala | Leu | Ser | His | Ala | Val | Gly |
|     |     | 290 |     |     |     | 295 |     |     |     | 300 |     |     |     |     |     |

| Leu | Pro | Ile | Thr | Leu | Ala | Gln | Leu | Asp | Ile | Lys | Glu | Asp | Val | Pro | Ala |
| 305 |     |     |     |     | 310 |     |     |     |     | 315 |     |     |     |     | 320 |

| Lys | Met | Arg | Ile | Val | Ala | Glu | Ala | Ala | Cys | Ala | Glu | Gly | Glu | Thr | Ile |
|     |     |     |     | 325 |     |     |     |     | 330 |     |     |     |     | 335 |     |

| His | Asn | Met | Pro | Gly | Gly | Ala | Thr | Pro | Asp | Gln | Val | Tyr | Ala | Ala | Leu |
|     |     |     | 340 |     |     |     |     | 345 |     |     |     |     | 350 |     |     |

| Leu | Val | Ala | Asp | Gln | Tyr | Gly | Gln | Arg | Phe | Leu | Gln | Glu | Trp | Glu |
|     |     |     | 355 |     |     |     |     | 360 |     |     |     |     | 365 |     |

<210> SEQ ID NO 6
<211> LENGTH: 1104
<212> TYPE: DNA
<213> ORGANISM: Escherichia coli
<220> FEATURE:
<221> NAME/KEY: misc_feature
<223> OTHER INFORMATION: GldA nucleotide sequence

<400> SEQUENCE: 6

```
atggaccgca ttattcaatc accgggtaaa tacatccagg gcgctgatgt gattaatcgt      60
ctgggcgaat acctgaagcc gctggcagaa cgctggttag tggtgggtga caaatttgtt     120
ttaggttttg ctcaatccac tgtcgagaaa agctttaaag atgctggact ggtagtagaa     180
attgcgccgt ttggcggtga atgttcgcaa atgagatcg accgtctgcg tggcatcgcg     240
gagactgcgc agtgtggcgc aattctcggt atcggtggcg aaaaaccct cgatactgcc     300
aaagcactgg cacatttcat gggtgttccg gtagcgatcg caccgactat cgcctctacc     360
gatgcaccgt gcagcgcatt gtctgttatc tacaccgatg agggtgagtt tgaccgctat     420
ctgctgttgc aaataacccc gaatatggtc attgtcgaca ccaaaatcgt cgctggcgca     480
cctgcacgtc tgttagcggc gggtatcggc gatgcgctgg caacctggtt tgaagcgcgt     540
gcctgctctc gtagcggcgc gaccaccatg gcgggcggca gtgcaccca ggctgcgctg     600
gcactggctg aactgtgcta acacccctg ctggaagaag gcgaaaaagc gatgcttgct     660
gccgaacagc atgtagtgac tccggcgctg gagcgcgtga ttgaagcgaa cacctatttg     720
agcggtgttg gttttgaaag tggtggtctg gctgcggcgc acgcagtgca taacggcctg     780
accgctatcc cggacgcgca tcactattat cacggtgaaa agtggcatt cggtacgctg     840
acgcagctgg ttctggaaaa tgcgccggtg gaggaaatcg aaaccgtagc tgcccttagc     900
catgcggtag gtttgccaat aactctcgct caactggata ttaaagaaga tgtcccggcg     960
aaaatgcgaa ttgtggcaga agcggcatgt gcagaaggtg aaaccattca acatgcct    1020
ggcggcgcga cgccagatca ggtttacgcc gctctgctgg tagccgacca gtacggtcag    1080
cgtttcctgc aagagtggga ataa                                           1104
```

<210> SEQ ID NO 7
<211> LENGTH: 387
<212> TYPE: PRT
<213> ORGANISM: Escherichia coli
<220> FEATURE:
<221> NAME/KEY: misc_feature
<223> OTHER INFORMATION: YqhD amino acid sequence

<400> SEQUENCE: 7

| Met | Asn | Asn | Phe | Asn | Leu | His | Thr | Pro | Thr | Arg | Ile | Leu | Phe | Gly | Lys |
| 1   |     |     |     | 5   |     |     |     |     | 10  |     |     |     |     | 15  |     |

| Gly | Ala | Ile | Ala | Gly | Leu | Arg | Glu | Gln | Ile | Pro | His | Asp | Ala | Arg | Val |

```
                   20                  25                  30
Leu Ile Thr Tyr Gly Gly Gly Ser Val Lys Lys Thr Gly Val Leu Asp
            35                  40                  45
Gln Val Leu Asp Ala Leu Lys Gly Met Asp Val Leu Glu Phe Gly Gly
        50                  55                  60
Ile Glu Pro Asn Pro Ala Tyr Glu Thr Leu Met Asn Ala Val Lys Leu
65                  70                  75                  80
Val Arg Glu Gln Lys Val Thr Phe Leu Leu Ala Val Gly Gly Gly Ser
                85                  90                  95
Val Leu Asp Gly Thr Lys Phe Ile Ala Ala Ala Asn Tyr Pro Glu
            100                 105                 110
Asn Ile Asp Pro Trp His Ile Leu Gln Thr Gly Gly Lys Glu Ile Lys
        115                 120                 125
Ser Ala Ile Pro Met Gly Cys Val Leu Thr Leu Pro Ala Thr Gly Ser
    130                 135                 140
Glu Ser Asn Ala Gly Ala Val Ile Ser Arg Lys Thr Thr Gly Asp Lys
145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
Val Asp Ala Phe Val His Thr Val Glu Gln Tyr Val Thr Lys Pro Val
        195                 200                 205
Asp Ala Lys Ile Gln Asp Arg Phe Ala Glu Gly Ile Leu Leu Thr Leu
    210                 215                 220
Ile Glu Asp Gly Pro Lys Ala Leu Lys Glu Pro Glu Asn Tyr Asp Val
225                 230                 235                 240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
            260                 265                 270
Leu Thr Ala Met His Gly Leu Asp His Ala Gln Thr Leu Ala Ile Val
        275                 280                 285
Leu Pro Ala Leu Trp Asn Glu Lys Arg Asp Thr Lys Arg Ala Lys Leu
    290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
    370                 375                 380
Ala Ala Arg
385

<210> SEQ ID NO 8
<211> LENGTH: 1164
<212> TYPE: DNA
<213> ORGANISM: Escherichia coli
<220> FEATURE:
<221> NAME/KEY: misc_feature
<223> OTHER INFORMATION: YqhD nucleotide sequence
```

<400> SEQUENCE: 8

```
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat taaaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
cgcgccaacg tcatgtgggc ggcgactcag gcgctgaacg gtttgattgg cgctggcgta     780
ccgcaggact gggcaacgca tatgctgggc cacgaactga ctgcgatgca cggtctggat     840
cacgcgcaaa cactggctat cgtcctgcct gcactgtgga atgaaaaacg cgataccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa atcatgaca ttacgttgga tgtcagccgc    1140
cgtatatacg aagccgcccg ctaa                                          1164
```

<210> SEQ ID NO 9
<211> LENGTH: 267
<212> TYPE: PRT
<213> ORGANISM: Escherichia coli
<220> FEATURE:
<221> NAME/KEY: misc_feature
<223> OTHER INFORMATION: YafB amino acid sequence

<400> SEQUENCE: 9

```
Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
            20                  25                  30

Ile Asp Thr Ala Gln Ile Tyr Asp Asn Glu Ala Ala Val Gly Gln Ala
        35                  40                  45

Ile Ala Glu Ser Gly Val Pro Arg His Glu Leu Tyr Ile Thr Thr Lys
    50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
```

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
            165                 170                 175

Ser Tyr Met Thr Leu Ala Tyr Gly Lys Ala Leu Lys Asp Glu Val Ile
        180                 185                 190

Ala Arg Ile Ala Ala Lys His Asn Ala Thr Pro Ala Gln Val Ile Leu
            195                 200                 205

Ala Trp Ala Met Gly Glu Gly Tyr Ser Val Ile Pro Ser Ser Thr Lys
        210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
            245                 250                 255

Val Ser Pro Glu Gly Leu Ala Pro Glu Trp Asp
        260                 265

<210> SEQ ID NO 10
<211> LENGTH: 804
<212> TYPE: DNA
<213> ORGANISM: Escherichia coli
<220> FEATURE:
<221> NAME/KEY: misc_feature
<223> OTHER INFORMATION: YafB nucleotide sequence

<400> SEQUENCE: 10

```
atggctatcc ctgcatttgg tttaggtact tccgtctga aagacgacgt tgttatttca      60
tctgtgataa cggcgcttga acttggttat cgcgcaattg ataccgcaca atctatgat     120 aacgaagccg cagtaggtca ggcgattgca gaaagtggcg tgccacgtca tgaactctac    180
atcaccacta aaatctggat tgaaaatctc agcaaagaca aattgatccc aagtctgaaa    240
gagagcctgc aaaaattgcg taccgattat gttgatctga cgctaatcca ctggccgtca    300
ccaaacgatg aagtctctgt tgaagagttt atgcaggcgc tgctggaagc caaaaaacaa    360
gggctgacgc gtgagatcgg tatttccaac ttcacgatcc cgttgatgga aaaagcgatt    420
gctgctgttg gtgctgaaaa catcgctact aaccagattg aactctctcc ttatctgcaa    480
aaccgtaaag tggttgcctg gctaaacag acggcatcc atattacttc ctatatgacg     540
ctggcgtatg gtaaggccct gaaagatgag gttattgctc gtatcgcagc taaacacaat    600
gcgactccgg cacaagtgat tctggcgtgg gctatggggg aaggttactc agtaattcct    660
tcttctacta aacgtaaaaa cctggaaagt aatcttaagg cacaaaattt acagcttgat    720
gccgaagata aaaagcgat cgccgcactg gattgcaacg accgcctggt tagcccggaa     780
ggtctggctc ctgaatggga ttaa                                            804
```

<210> SEQ ID NO 11
<211> LENGTH: 284
<212> TYPE: PRT
<213> ORGANISM: Escherichia coli
<220> FEATURE:
<221> NAME/KEY: misc_feature
<223> OTHER INFORMATION: YeaE amino acid sequence

<400> SEQUENCE: 11

Met Gln Gln Lys Met Ile Gln Phe Ser Gly Asp Val Ser Leu Pro Ala
1               5                   10                  15

Val Gly Gln Gly Thr Trp Tyr Met Gly Asp Ala Ser Gln Arg Lys
            20                  25                  30

Thr Glu Val Ala Ala Leu Arg Ala Gly Ile Glu Leu Gly Leu Thr Leu
        35                  40                  45

Ile Asp Thr Ala Glu Met Tyr Ala Asp Gly Gly Ala Glu Lys Val Val
    50                  55                  60

Gly Glu Ala Leu Thr Gly Leu Arg Glu Lys Val Phe Leu Val Ser Lys
65                  70                  75                  80

Val Tyr Pro Trp Asn Ala Gly Gln Lys Ala Ile Asn Ala Cys Glu
                85                  90                  95

Ala Ser Leu Arg Arg Leu Asn Thr Asp Tyr Leu Asp Leu Tyr Leu Leu
            100                 105                 110

His Trp Ser Gly Ser Phe Ala Phe Glu Glu Thr Val Ala Ala Met Glu
        115                 120                 125

Lys Leu Ile Ala Gln Gly Lys Ile Arg Arg Trp Gly Val Ser Asn Leu
    130                 135                 140

Asp Tyr Ala Asp Met Gln Glu Leu Trp Gln Leu Pro Gly Gly Asn Gln
145                 150                 155                 160

Cys Ala Thr Asn Gln Val Leu Tyr His Leu Gly Ser Arg Gly Ile Glu
                165                 170                 175

Tyr Asp Leu Leu Pro Trp Cys Gln Gln Gln Met Pro Val Met Ala
            180                 185                 190

Tyr Ser Pro Leu Ala Gln Ala Gly Arg Leu Arg Asn Gly Leu Leu Lys
        195                 200                 205

Asn Ala Val Val Asn Glu Ile Ala His Ala His Asn Ile Ser Ala Ala
    210                 215                 220

Gln Val Leu Leu Ala Trp Val Ile Ser His Gln Gly Val Met Ala Ile
225                 230                 235                 240

Pro Lys Ala Ala Thr Ile Ala His Val Gln Gln Asn Ala Ala Val Leu
                245                 250                 255

Glu Val Glu Leu Ser Ser Ala Glu Leu Ala Met Leu Asp Lys Ala Tyr
            260                 265                 270

Pro Ala Pro Lys Gly Lys Thr Ala Leu Asp Met Val
        275                 280

<210> SEQ ID NO 12
<211> LENGTH: 855
<212> TYPE: DNA
<213> ORGANISM: Escherichia coli
<220> FEATURE:
<221> NAME/KEY: misc_feature
<223> OTHER INFORMATION: YeaE nucleotide sequence

<400> SEQUENCE: 12
atgcaacaaa aaatgattca atttagtggc gatgtctcac tgccagccgt agggcaggga      60
acatggtata tgggcgaaga tgccagtcag cgcaaaacag aagttgctgc actacgcgcg     120
ggcattgaac tcggtttaac cctcattgat accgccgaaa tgtatgccga tggcggtgcc     180
gaaaaggtgg ttggggaagc attaaccggt ctgcgagaga aggtctttct cgtctctaaa     240
gtctatccgt ggaatgctgg cgggcaaaaa gcgataaatg catgcgaagc cagtttacgc     300
cgtctcaata ctgattatct cgatctttac ttattacact ggtctggcag tttcgctttt     360
gaagagactg tcgcagcgat ggaaaaattg atcgcccagg gaaaaatccg ccgctggggc     420
gtttctaacc ttgattatgc tgatatgcag gaactctggc agctgccggg gggaaatcag     480
tgtgccacta atcaggtgct ttaccatctc ggttcacgag gaattgagta cgatctactc     540

```
cctggtgcc agcaacagca gatgccggtg atggcttaca gtccgttagc ccaggccggg    600
cggttgcgca atggactgtt aaaaaacgcg gtagtcaacg aaattgcaca tgctcacaat    660
atcagcgcgg cacaagtatt gttggcgtgg gtgatcagtc atcagggtgt gatggcgatt    720
ccaaaagcgg ccacgattgc ccatgtccaa caaaatgcgg ctgtgcttga ggtcgaactt    780
tcttcagcgg aattagctat gctggataag gcatatccgg caccaaaagg aaaaactgcg    840
ctggatatgg tgtga                                                    855
```

```
<210> SEQ ID NO 13
<211> LENGTH: 275
<212> TYPE: PRT
<213> ORGANISM: Escherichia coli
<220> FEATURE:
<221> NAME/KEY: misc_feature
<223> OTHER INFORMATION: YqhE amino acid sequence

<400> SEQUENCE: 13
```

```
Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
            20                  25                  30

Ala Ile Gln Lys Ala Leu Glu Val Gly Tyr Arg Ser Ile Asp Thr Ala
        35                  40                  45

Ala Ala Tyr Lys Asn Glu Glu Gly Val Gly Lys Ala Leu Lys Asn Ala
    50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
            100                 105                 110

Ile Asp His Tyr Val Glu Ala Trp Lys Gly Met Ile Glu Leu Gln Lys
        115                 120                 125

Glu Gly Leu Ile Lys Ser Ile Gly Val Cys Asn Phe Gln Ile His His
    130                 135                 140

Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
            180                 185                 190

Gly Lys Gly Val Phe Asp Gln Lys Val Ile Arg Asp Leu Ala Asp Lys
        195                 200                 205

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
            260                 265                 270

Phe Gly Gly
        275
```

```
<210> SEQ ID NO 14
<211> LENGTH: 828
<212> TYPE: DNA
<213> ORGANISM: Escherichia coli
<220> FEATURE:
<221> NAME/KEY: misc_feature
<223> OTHER INFORMATION: YqhE nucleotide sequence

<400> SEQUENCE: 14
atggctaatc caaccgttat taagctacag gatggcaatg tcatgcccca gctgggactg      60
ggcgtctggc aagcaagtaa tgaggaagta atcaccgcca ttcaaaaagc gttagaagtg     120
ggttatcgct cgattgatac cgccgcggcc tacaagaacg aagaaggtgt cggcaaagcc     180
ctgaaaaatg cctcagtcaa cagagaagaa ctgttcatca ccactaagct gtggaacgac     240
gaccacaagc gcccccgcga agccctgctc gacagcctga aaaaactcca gcttgattat     300
atcgacctct acttaatgca ctggcccgtt cccgctatcg accattatgt cgaagcatgg     360
aaaggcatga tcgaattgca aaagagggga ttaatcaaaa gcatcggcgt gtgcaacttc     420
cagatccatc acctgcaacg cctgattgat gaaactggcg tgacgcctgt gataaaccag     480
atcgaacttc atccgctgat gcaacaacgc cagctacacg cctggaacgc gacacacaaa     540
atccagaccg aatcctggag cccattagcg caaggaggga aaggcgtttt cgatcagaaa     600
gtcattcgcg atctggcaga taaatacggc aaaaccccgg cgcagattgt tatccgctgg     660
catctggata gcggcctggt ggtgatcccg aaatcggtca cccttcacg tattgccgaa      720 aactttgatg tctgggattt ccgtctcgac aaagacgaac tcggcgaaat tgcaaaactc     780
gatcagggca gcgtctcgg tcccgatcct gaccagttcg gcggctaa                    828

<210> SEQ ID NO 15
<211> LENGTH: 298
<212> TYPE: PRT
<213> ORGANISM: Escherichia coli
<220> FEATURE:
<221> NAME/KEY: misc_feature
<223> OTHER INFORMATION: YdhF amino acid sequence

<400> SEQUENCE: 15

Met Val Gln Arg Ile Thr Ile Ala Pro Gln Gly Pro Glu Phe Ser Arg
1               5                   10                  15

Phe Val Met Gly Tyr Trp Arg Leu Met Asp Trp Asn Met Ser Ala Arg
                20                  25                  30

Gln Leu Val Ser Phe Ile Glu Glu His Leu Asp Leu Gly Val Thr Thr
            35                  40                  45

Val Asp His Ala Asp Ile Tyr Gly Gly Tyr Gln Cys Glu Ala Ala Phe
        50                  55                  60

Gly Glu Ala Leu Lys Leu Ala Pro His Leu Arg Glu Arg Met Glu Ile
65                  70                  75                  80

Val Ser Lys Cys Gly Ile Ala Thr Thr Ala Arg Glu Glu Asn Val Ile
                85                  90                  95

Gly His Tyr Ile Thr Asp Arg Asp His Ile Ile Lys Ser Ala Glu Gln
                100                 105                 110

Ser Leu Ile Asn Leu Ala Thr Asp His Leu Asp Leu Leu Ile His
            115                 120                 125

Arg Pro Asp Pro Leu Met Asp Ala Asp Glu Val Ala Asp Ala Phe Lys
        130                 135                 140

His Leu His Gln Ser Gly Lys Val Arg His Phe Gly Val Ser Asn Phe
145                 150                 155                 160
```

```
Thr Pro Ala Gln Phe Ala Leu Leu Gln Ser Arg Leu Pro Phe Thr Leu
            165                 170                 175
Ala Thr Asn Gln Val Glu Ile Ser Pro Val His Gln Pro Leu Leu Leu
        180                 185                 190
Asp Gly Thr Leu Asp Gln Leu Gln Gln Leu Arg Val Arg Pro Met Ala
    195                 200                 205
Trp Ser Cys Leu Gly Gly Arg Leu Phe Asn Asp Asp Tyr Phe Gln
210                 215                 220
Pro Leu Arg Asp Glu Leu Ala Val Val Ala Glu Leu Asn Ala Gly
225                 230                 235                 240
Ser Ile Glu Gln Val Val Tyr Ala Trp Val Leu Arg Leu Pro Ser Gln
            245                 250                 255
Pro Leu Pro Ile Ile Gly Ser Gly Lys Ile Glu Arg Val Arg Ala Ala
        260                 265                 270
Val Glu Ala Glu Thr Leu Lys Met Thr Arg Gln Gln Trp Phe Arg Ile
    275                 280                 285
Arg Lys Ala Ala Leu Gly Tyr Asp Val Pro
290                 295
```

<210> SEQ ID NO 16
<211> LENGTH: 897
<212> TYPE: DNA
<213> ORGANISM: Escherichia coli
<220> FEATURE:
<221> NAME/KEY: misc_feature
<223> OTHER INFORMATION: YdhF nucleotide sequence

<400> SEQUENCE: 16

```
atggttcagc gtattactat tgcgccgcaa ggcccggagt tttcccgttt tgtgatgggc      60
tactggcgat tgatggactg gaatatgtcc gcccgccagc tggtcagttt tattgaagag     120
catctggatc tcggcgtgac caccgtggac catgctgata tttatggtgg ctatcagtgc     180
gaagcggcgt ttggcgaggc actgaaactg caccctcacc tgcgtgaacg gatgaaaatc     240
gtcagtaaat gcggtatcgc gacgaccgcg cgtgaagaaa acgtcattgg tcattacatc     300
actgaccgcg atcacatcat taagagcgcc gaacagtcgc taattaatct cgcgaccgat     360
catctggatt tgctgttaat ccaccgacca gacccgttaa tggatgccga tgaagtggcg     420
gacgcgttca acatctgca tcagagcggc aaagtgcgtc attttggcgt atcgaacttt     480
acgcctgcgc aatttgcccct gttgcaatca cgtctgccgt ttacccttgc cactaatcag     540
gtggaaatat ccccggtgca tcagccgtta ctgctggatg gcacgctcga ccaactacaa     600
caactgcgtg ttcgtccgat ggcgtggtcc tgccttggtg gtggtcgtct gtttaatgat     660
gattatttcc agccgctgcg tgatgaactg gctgtggtgg cagaggagtt aaacgcgggc     720
tcgattgaac aggtggttta cgcctgggta ttacgtttac catcgcagcc gctgccaatt     780
atcggttcag gtaaaattga gcgcgtacgg gcagctgtcg aagcagaaac actgaaaatg     840
acccgtcaac aatggtttcg tatccgtaaa gcggcactgg ggtacgacgt accgtaa     897
```

<210> SEQ ID NO 17
<211> LENGTH: 332
<212> TYPE: PRT
<213> ORGANISM: Gluconobacter oxydans
<220> FEATURE:
<221> NAME/KEY: misc_feature
<223> OTHER INFORMATION: GOX1615 amino acid sequence

<400> SEQUENCE: 17

```
Met Ala Ser Asp Thr Ile Arg Ile Pro Gly Ile Asp Thr Pro Leu Ser
1               5                   10                  15

Arg Val Ala Leu Gly Thr Trp Ala Ile Gly Trp Met Trp Gly Gly
            20                  25                  30

Pro Asp Asp Asn Gly Val Arg Thr Ile His Ala Ala Leu Asp Glu
        35                  40                  45

Gly Ile Asn Leu Ile Asp Thr Ala Pro Val Tyr Gly Phe Gly His Ser
    50                  55                  60

Glu Glu Ile Val Gly Arg Ala Leu Ala Glu Lys Pro Asn Lys Ala His
65                  70                  75                  80

Val Ala Thr Lys Leu Gly Leu His Trp Val Gly Glu Asp Glu Lys Asn
                85                  90                  95

Met Lys Val Phe Arg Asp Ser Arg Pro Ala Arg Ile Arg Lys Glu Val
            100                 105                 110

Glu Asp Ser Leu Arg Arg Leu Arg Val Glu Thr Ile Asp Leu Glu Gln
        115                 120                 125

Ile His Trp Pro Asp Asp Lys Thr Pro Ile Asp Glu Ser Ala Arg Glu
    130                 135                 140

Leu Gln Lys Leu His Gln Asp Gly Lys Ile Arg Ala Leu Gly Val Ser
145                 150                 155                 160

Asn Phe Ser Pro Glu Gln Met Asp Ile Phe Arg Glu Val Ala Pro Leu
                165                 170                 175

Ala Thr Ile Gln Pro Pro Leu Asn Leu Phe Glu Arg Thr Ile Glu Lys
            180                 185                 190

Asp Ile Leu Pro Tyr Ala Glu Lys His Asn Ala Val Val Leu Ala Tyr
        195                 200                 205

Gly Ala Leu Cys Arg Gly Leu Leu Thr Gly Lys Met Asn Arg Asp Thr
    210                 215                 220

Thr Phe Pro Lys Asp Asp Leu Arg Ser Asn Asp Pro Lys Phe Gln Lys
225                 230                 235                 240

Pro Asn Phe Glu Lys Tyr Leu Ala Ala Met Asp Glu Phe Glu Lys Leu
                245                 250                 255

Ala Glu Lys Arg Gly Lys Ser Val Met Ala Phe Ala Val Arg Trp Val
            260                 265                 270

Leu Asp Gln Gly Pro Val Ile Ala Leu Trp Gly Ala Arg Lys Pro Gly
        275                 280                 285

Gln Val Ser Gly Val Lys Asp Val Phe Gly Trp Ser Leu Thr Asp Glu
    290                 295                 300

Glu Lys Lys Ala Val Asp Asp Ile Leu Ala Arg His Val Pro Asn Pro
305                 310                 315                 320

Ile Asp Pro Thr Phe Met Ala Pro Pro Ala Arg Asp
                325                 330

<210> SEQ ID NO 18
<211> LENGTH: 999
<212> TYPE: DNA
<213> ORGANISM: Gluconobacter oxydans
<220> FEATURE:
<221> NAME/KEY: misc_feature
<223> OTHER INFORMATION: GOX1615 nucleotide sequence

<400> SEQUENCE: 18
atggcatccg acaccatccg catccccggc atcgacacgc ctctctcccg cgtcgccctc      60
ggcacctggg ccatcggcgg ctggatgtgg ggcggcccg atgatgacaa tggcgtccgc     120
accattcacg cggccctcga tgaaggcatc aacctgatcg acaccgcccc ggtctacggc     180
```

```
ttcggccatt ccgaggaaat cgtcggccgg gcactcgccg agaagcccaa caaggcgcat    240
gtcgccacga aactcgggct ccactgggtt ggcgaagacg aaaagaatat gaaggtcttc    300
cgggactccc gcccggcccg catccgcaag gaagtcgagg actcgctccg ccgtctgcgt    360
gtggagacga tcgatctcga gcagatccac tggcccgacg acaaaacccc gatcgacgag    420
agcgcccgcg agcttcagaa actccatcag gacggcaaga tccgtgccct cggcgtaagc    480
aacttctcgc cggagcagat ggacatcttc cgcgaagtcg ccccgctcgc cacgatccag    540
cccccgctga acctttcga acgcaccatc gagaaggaca tcctgcccta cgccgaaaag    600
cacaatgccg tcgttctcgc ttacggggcc ctctgccgcg gcctgctgac aggcaagatg    660
aaccgcgata cgaccttccc gaaggatgac ctgcgttcga acgatccgaa gttccagaag    720
ccgaatttcg agaagtacct cgcagccatg gacgagttcg aaaagcttgc cgaaaagcgc    780
ggcaagtctg tgatggcctt cgcggttcgc tgggttctgg atcagggccc ggtaatcgcc    840
ctgtggggtg cccgcaagcc gggtcaggtc tcaggcgtaa aggacgtctt cggctggtcc    900
ctgaccgacg aagagaagaa agccgtggac gacattctgg ctaggcatgt ccccaatccc    960
atcgacccga ctttcatggc gccccggca cgggactga                            999
```

<210> SEQ ID NO 19
<211> LENGTH: 330
<212> TYPE: PRT
<213> ORGANISM: Bacillus subtilis
<220> FEATURE:
<221> NAME/KEY: misc_feature
<223> OTHER INFORMATION: YdhN amino acid sequence

<400> SEQUENCE: 19

Met Glu Tyr Thr Ser Ile Ala Asp Thr Gly Ile Glu Ala Ser Arg Ile
1               5                   10                  15

Gly Leu Gly Thr Trp Ala Ile Gly Gly Thr Met Trp Gly Gly Thr Asp
                20                  25                  30

Glu Lys Thr Ser Ile Glu Thr Ile Arg Ala Ala Leu Asp Gln Gly Ile
            35                  40                  45

Thr Leu Ile Asp Thr Ala Pro Ala Tyr Gly Phe Gly Gln Ser Glu Glu
        50                  55                  60

Ile Val Gly Lys Ala Lys Glu Tyr Gly Lys Arg Asp Gln Val Ile Leu
65                  70                  75                  80

Ala Thr Lys Thr Ala Leu Asp Trp Lys Asn Asn Gln Leu Phe Arg His
                85                  90                  95

Ala Asn Arg Ala Arg Ile Val Glu Glu Val Glu Asn Ser Leu Lys Arg
            100                 105                 110

Leu Gln Thr Asp Tyr Ile Asp Leu Tyr Gln Val His Trp Pro Asp Pro
        115                 120                 125

Leu Val Pro Ile Glu Glu Thr Ala Glu Val Met Lys Glu Leu Tyr Asp
    130                 135                 140

Ala Gly Lys Ile Arg Ala Ile Gly Val Ser Asn Phe Ser Ile Glu Gln
145                 150                 155                 160

Met Asp Thr Phe Arg Ala Val Ala Pro Leu His Thr Ile Gln Pro Pro
                165                 170                 175

Tyr Asn Leu Phe Glu Arg Glu Met Glu Glu Ser Val Leu Pro Tyr Ala
            180                 185                 190

Lys Asp Asn Lys Ile Thr Thr Leu Leu Tyr Gly Ser Leu Cys Arg Gly
        195                 200                 205

Leu Leu Thr Gly Lys Met Thr Glu Glu Tyr Thr Phe Glu Gly Asp Asp
210                 215                 220

Leu Arg Asn His Asp Pro Lys Phe Gln Lys Pro Arg Phe Lys Glu Tyr
225                 230                 235                 240

Leu Ser Ala Val Asn Gln Leu Asp Lys Leu Ala Lys Thr Arg Tyr Gly
            245                 250                 255

Lys Ser Val Ile His Leu Ala Val Arg Trp Ile Leu Asp Gln Pro Gly
                260                 265                 270

Ala Asp Ile Ala Leu Trp Gly Ala Arg Lys Pro Gln Leu Glu Ala
            275                 280                 285

Leu Ser Glu Ile Thr Gly Trp Thr Leu Asn Ser Glu Asp Gln Lys Asp
290                 295                 300

Ile Asn Thr Ile Leu Glu Asn Thr Ile Ser Asp Pro Val Gly Pro Glu
305                 310                 315                 320

Phe Met Ala Pro Pro Thr Arg Glu Glu Ile
                325                 330

```
<210> SEQ ID NO 20
<211> LENGTH: 996
<212> TYPE: DNA
<213> ORGANISM: Bacillus subtilis
<220> FEATURE:
<221> NAME/KEY: misc_feature
<223> OTHER INFORMATION: YdhN nucleotide sequence

<400> SEQUENCE: 20
atggaatata ccagtatagc agatacagga atagaagcct ccagaatcgg cctcggcaca      60
tgggccattg gcggaacgat gtggggaggc actgacgaaa aacatcgat tgaaacaatc     120 cgcgccgctc ttgatcaggg gattacactg attgacaccg caccggctta cggcttcggg     180
cagtccgagg aaattgtcgg aaaggcaatc aaagagtacg gcaaaagaga ccaggtgatt     240
ctcgcaacga aaacggctct ggactggaag acaaccagc tgttccgcca tgcgaacaga     300
gcgagaattg tagaggaagt tgagaattct ttgaagcggc ttcaaacaga ctatattgat     360
ctttatcagg tgcattggcc cgatccgctt gtgccaattg aagaaacggc tgaagtcatg     420
aaggaattat atgatgcggg aaaaatccgg gcgattggcg tcagcaattt ttcaattgag     480
caaatggata catttcgcgc cgtcgcacct ctccatacga ttcagcctcc atataatctg     540
tttgaaagag agatggaaga gagtgtcctt ccttatgcga agataacaa gataacaaca     600 ttattatacg gcagtttatg cagagggctg ttaacaggca aatgactga agaatataca     660 tttgagggcg atgatctgcg taatcacgat ccaaaattcc agaagccccg ctttaaagag     720 tatcttctg ctgtgaatca attggataag ctggcgaaga cacgttatgg aaaatcagtg     780
attcacttgg ctgtcagatg gatcttagat cagccgggag cggatatcgc tctttgggga     840
gcaagaaagc ctgggcagct tgaggcccta tctgagatta caggctggac gctgaacagt     900
gaagatcaga aagatatcaa tactatattg gaaaatacga tatcagaccc tgtcggaccg     960
gagtttatgg ccccgccgac cagagaggaa atataa                               996

<210> SEQ ID NO 21
<211> LENGTH: 318
<212> TYPE: PRT
<213> ORGANISM: Hypocrea jecorina
<220> FEATURE:
<221> NAME/KEY: misc_feature
<223> OTHER INFORMATION: Gld2 amino acid sequence

<400> SEQUENCE: 21
```

```
Met Ala Ser Lys Thr Tyr Thr Leu Asn Thr Gly Ala Lys Ile Pro Ala
1               5                   10                  15

Val Gly Phe Gly Thr Phe Ala Asn Glu Gly Ala Lys Gly Glu Thr Tyr
            20                  25                  30

Ala Ala Val Thr Lys Ala Leu Asp Val Gly Tyr Arg His Leu Asp Cys
        35                  40                  45

Ala Trp Phe Tyr His Asn Glu Asp Glu Val Gly Asp Ala Val Arg Asp
    50                  55                  60

Phe Leu Ala Arg Arg Pro Asp Val Lys Arg Glu Asp Leu Phe Ile Cys
65                  70                  75                  80

Thr Lys Val Trp Asn His Leu His Glu Pro Gly Asp Val Lys Trp Ser
                85                  90                  95

Ala Lys Asn Ser Cys Glu Asn Leu Lys Val Asp Tyr Ile Asp Leu Phe
            100                 105                 110

Leu Val His Trp Pro Ile Ala Ala Glu Lys Asn Ser Asp Arg Ser Val
        115                 120                 125

Lys Leu Gly Pro Asp Gly Lys Tyr Val Ile Asn Gln Ala Leu Thr Glu
    130                 135                 140

Asn Pro Glu Pro Thr Trp Arg Ala Met Glu Glu Leu Val Glu Ser Gly
145                 150                 155                 160

Leu Val Lys Ala Ile Gly Val Ser Asn Trp Thr Ile Pro Gly Leu Lys
                165                 170                 175

Lys Leu Leu Gln Ile Ala Lys Ile Lys Pro Ala Val Asn Gln Ile Glu
            180                 185                 190

Ile His Pro Phe Leu Pro Asn Glu Glu Leu Val Ala Phe Cys Phe Glu
        195                 200                 205

Asn Gly Ile Leu Pro Glu Ala Tyr Ser Pro Leu Gly Ser Gln Asn Gln
    210                 215                 220

Val Pro Ser Thr Gly Glu Arg Val Arg Asp Asn Pro Thr Leu Lys Ala
225                 230                 235                 240

Val Ala Glu Arg Ser Gly Tyr Ser Leu Ala Gln Ile Leu Leu Ala Trp
                245                 250                 255

Gly Leu Lys Arg Gly Tyr Val Val Leu Pro Lys Ser Ser Thr Pro Ser
            260                 265                 270

Arg Ile Glu Ser Asn Phe Asn Ile Pro Glu Leu Ser Asp Glu Asp Phe
        275                 280                 285

Glu Ala Ile Gln Gln Val Ala Lys Gly Arg His Thr Arg Phe Val Asn
    290                 295                 300

Met Lys Asp Thr Phe Gly Tyr Asn Val Trp Pro Glu Glu Glu
305                 310                 315

<210> SEQ ID NO 22
<211> LENGTH: 957
<212> TYPE: DNA
<213> ORGANISM: Hypocrea jecorina
<220> FEATURE:
<221> NAME/KEY: misc_feature
<223> OTHER INFORMATION: Gld2 nucleotide sequence

<400> SEQUENCE: 22
atggcctcca agacgtacac tctgaacacc ggtgccaaga tacccgcggt cgggttcggc    60
acattcgcca atgagggtgc caagggcgag acatacgcag ctgttacaaa ggcactggac   120
gttggatacc gccaccttga ttgcgcgtgg ttttaccaca cgaagatgaa ggttggtgac   180
gcggtacgcg atttctcgc cgccgaccc gacgtgaaac gcgaggatct cttcatttgc   240
```

```
accaaagttt ggaaccacct gcatgagcca gaggacgtca agtggagcgc caagaactcg    300
tgcgaaaacc tcaaggtcga ttacattgac ctgttcctcg tccactggcc aatcgcggcc    360
gagaagaaca gcgacaggag cgtcaagctg ggccccgatg gcaagtatgt catcaaccaa    420
gccctgacgg aaaacccaga gccaacatgg cgagccatgg aagagcttgt tgaaagcggc    480
ctcgtcaagg caattggagt atccaactgg acgattccgg ggttgaagaa gctccttcag    540
atcgccaaga tcaagccggc agtgaaccag attgagattc acccattcct accaaacgaa    600
gagcttgtgg cgttctgctt tgagaacggg atcctgcccg aagcctactc gccgctgggc    660
tcgcagaacc aggtcccaag caccggcgag cgagtgcgcg caacccgac  actcaaagcg    720 gttgccgagc gaagcggcta cagccttgcc cagatcctat ggcatgggg  cctgaagcga    780 ggatatgtgg tcctcccaaa gagctcaact ccaagccgta ttgaaagcaa cttcaacatt    840
ccggagctga gtgatgaaga ctttgaggcg attcaacagg ttgctaaggg gagacatact    900
agatttgtca acatgaagga cacgtttgga tacaacgttt ggccagagga ggaataa      957
```

```
<210> SEQ ID NO 23
<211> LENGTH: 284
<212> TYPE: PRT
<213> ORGANISM: Leishmania donovani
<220> FEATURE:
<221> NAME/KEY: misc_feature
<223> OTHER INFORMATION: Alr amino acid sequence

<400> SEQUENCE: 23

Met Ala Asp Val Gly Lys Ala Met Val Thr Leu Ser Asn Gly Val Gln
1               5                   10                  15

Met Pro Gln Leu Gly Leu Gly Val Trp Gln Ser Pro Ala Gly Glu Val
                20                  25                  30

Thr Ala Asn Ala Val Lys Trp Ala Leu Cys Ala Gly Tyr Arg His Ile
            35                  40                  45

Asp Thr Ala Ala Ile Tyr Lys Asn Glu Glu Ser Val Gly Ala Gly Leu
        50                  55                  60

Arg Ala Ser Gly Val Pro Arg Glu Asp Val Phe Ile Thr Thr Lys Leu
65                  70                  75                  80

Trp Asn Thr Glu Gln Gly Tyr Glu Ser Thr Leu Ala Ala Phe Glu Glu
                85                  90                  95

Ser Arg Gln Lys Leu Gly Val Asp Tyr Ile Asp Leu Tyr Leu Ile His
                100                 105                 110

Trp Pro Arg Gly Lys Asp Ile Val Ser Lys Glu Gly Lys Lys Tyr Leu
            115                 120                 125

Asp Ser Trp Arg Ala Phe Glu Gln Leu Tyr Lys Asp Lys Lys Val Arg
        130                 135                 140

Ala Ile Gly Val Ser Asn Phe His Ile His His Leu Glu Asp Val Leu
145                 150                 155                 160

Ala Met Cys Thr Val Thr Pro Met Val Asn Gln Val Glu Leu His Pro
                165                 170                 175

Leu Asn Asn Gln Ala Glu Leu Arg Ala Phe Cys Asp Ala Lys Gln Ile
                180                 185                 190

Lys Val Glu Ala Trp Ser Pro Leu Gly Gln Gly Lys Leu Leu Ser Asn
            195                 200                 205

Pro Ile Leu Ala Ala Ile Gly Ala Lys Tyr Asn Lys Thr Ala Ala Gln
        210                 215                 220

Val Ile Leu Arg Trp Asn Ile Gln Lys Asn Leu Ile Thr Ile Pro Lys
```

```
                    225                 230                 235                 240
Ser Val His Lys Glu Arg Ile Glu Glu Asn Ala Asp Val Phe Asn Phe
                245                 250                 255

Glu Leu Asp Ala Glu Asp Val Met Ser Ile Asp Ala Leu Asn Thr Asn
            260                 265                 270

Ser Arg Tyr Gly Pro Asp Pro Asp Glu Ala Gln Phe
        275                 280

<210> SEQ ID NO 24
<211> LENGTH: 855
<212> TYPE: DNA
<213> ORGANISM: Leishmania donovani
<220> FEATURE:
<221> NAME/KEY: misc_feature
<223> OTHER INFORMATION: Alr nucleotide sequence

<400> SEQUENCE: 24
atggctgacg ttggtaaggc aatggtcacg ctgagcaacg gcgtccagat gccgcagctc      60
ggcctcggcg tgtggcagtc ccccgccggc gaggtaactg cgaacgccgt caagtgggcg     120
ctgtgtgccg gctaccgcca catcgacact gcagccatct acaagaatga ggagagcgtc     180
ggcgccgggc tgcgtgcctc tggtgtaccg cgcgaggatg tgttcatcac gacgaagctc     240
tggaacacgg agcaaggcta cgagagcacg ctcgcggcct tcgaggagag tcgacagaag     300
ctcggtgttg actacattga tctctacctc atccactggc cgcgcggcaa agacatcgtg     360
tcgaaagagg gcaagaagta cctggactcg tggcgcgcct tcgagcagct ctacaaggat     420
aagaaggtgc gggcgattgg ggtgtcgaac tttcacatcc accatctgga ggacgtgctt     480
gcaatgtgca cggtgacgcc aatggtgaac caggtggagc ttcacccgtt gaacaatcag     540
gccgagctgc gggccttctg cgacgccaag caaatcaaag tcgaggcttg gtcgccgcta     600
gggcagggca agctgctctc caacccgatc ctcgccgcaa tcggcgcaaa gtacaataag     660
acggccgcgc aggtgatcct ccgctggaac atccaaaaga atctcatcac gatccccaag     720
tcggtccaca aggagcgtat cgaggagaac gcggacgtct tcaatttcga gctcgacgcc     780
gaggacgtga tgagtatcga cgctctcaac acgaactcac gctacggccc cgaccccgat     840
gaggcgcagt tctaa                                                      855

<210> SEQ ID NO 25
<211> LENGTH: 424
<212> TYPE: PRT
<213> ORGANISM: Lactobacillus sake
<220> FEATURE:
<221> NAME/KEY: misc_feature
<223> OTHER INFORMATION: LarA amino acid sequence

<400> SEQUENCE: 25

Met Val Ala Ile Lys Leu Pro Tyr Asp Gln Lys Ile Ile Thr Ala Asn
1               5                   10                  15

Ile Ala Asp Ala Asn Phe Ala Gly Lys Leu Val Ser Gln Ala Ala Thr
            20                  25                  30

Tyr Gln Asn Pro Leu Ser Glu Val Glu Thr Val Glu Gln Ser Leu Asp
        35                  40                  45

Asn Pro Ile Asp Ser Pro Lys Leu Glu Glu Leu Ala Lys Gly Lys Lys
    50                  55                  60

Asn Ile Val Ile Ile Ser Ser Asp His Thr Arg Pro Val Pro Ser His
65                  70                  75                  80

Ile Met Thr Pro Ile Leu Leu Arg Arg Ile Arg Ser Val Ala Pro Asp
```

```
            85                  90                  95
Ala Arg Ile Arg Ile Leu Val Ala Thr Gly Phe His Arg Pro Ser Thr
                100                 105                 110

His Glu Glu Leu Val Asn Lys Tyr Gly Glu Ile Val Ala Asn Glu
        115                 120                 125

Glu Ile Val Met His Ile Ser Thr Asp Asp Ser Ser Val Val Lys Ile
130                 135                 140

Gly Gln Leu Pro Ser Gly Gly Asp Cys Ile Ile Asn Lys Ile Ala Val
145                 150                 155                 160

Glu Ala Asp Leu Leu Ile Ser Glu Gly Phe Ile Glu Ser His Phe Phe
                165                 170                 175

Ala Gly Phe Ser Gly Gly Arg Lys Ser Ile Leu Pro Gly Val Ala Ser
                180                 185                 190

Tyr Lys Thr Ile Met Ala Asn His Ser Gly Glu Phe Ile Asn Ser His
                195                 200                 205

Tyr Ser Arg Thr Gly Asn Leu Met His Asn Pro Val His Lys Asp Met
210                 215                 220

Val Tyr Ala Ala Lys Thr Ala Gly Leu Lys Phe Ile Leu Asn Val Val
225                 230                 235                 240

Leu Asp Glu Asp Lys His Ile Ile Gly Ser Phe Ala Gly Asn Leu Glu
                245                 250                 255

Thr Ala His Lys Lys Gly Cys Asp Phe Val Glu Ser Leu Ser Glu Val
                260                 265                 270

Asp Lys Ile Asp Cys Asp Ile Ala Ile Ser Thr Asn Gly Gly Tyr Pro
                275                 280                 285

Leu Asp Gln Asn Ile Tyr Gln Ala Val Lys Gly Met Thr Ala Ala Glu
290                 295                 300

Ala Thr Asn Lys Gln Gly Gly Val Ile Ile Met Val Ala Gly Ala Arg
305                 310                 315                 320

Asp Gly His Gly Gly Asp Gly Phe Tyr His Asn Ile Ala Asp Val Lys
                325                 330                 335

Asp Pro Lys Glu Phe Leu Asp Gln Ala Ile Asn Thr Pro Arg Leu Glu
                340                 345                 350

Thr Val Pro Asp Gln Trp Thr Ser Gln Ile Leu Ala Arg Ile Leu Val
                355                 360                 365

Gln His His Val Ile Phe Val Ser Asp Leu Val Asp Pro Gln Leu Ile
        370                 375                 380

Thr Asp Met His Met Glu Leu Ala Thr Ser Leu Asp Ala Ala Leu Glu
385                 390                 395                 400

Arg Ala Tyr Ala Ile Glu Gly Val Asp Ala Lys Val Thr Val Ile Pro
                405                 410                 415

Asp Gly Leu Gly Val Ile Val Lys
            420

<210> SEQ ID NO 26
<211> LENGTH: 1275
<212> TYPE: DNA
<213> ORGANISM: Lactobacillus sake
<220> FEATURE:
<221> NAME/KEY: misc_feature
<223> OTHER INFORMATION: LarA nucleotide sequence

<400> SEQUENCE: 26
ttggtagcta taaaattacc ttacgatcaa aaaattatta cggctaatat tgcagatgct      60
aattttgccg gcaagttggt ttctcaagca gccacttatc aaaatccatt gagtgaggtc     120
```

```
gaaacagttg aacagtcatt ggataatcct attgatagtc cgaagttgga agaattggcg    180
aagggaaaga agaacattgt catcatcagt tctgaccaca cccgaccagt accttcacat    240
attatgacgc ctattttatt aagacggatt cgttcagtgg cacctgatgc acgcattcgc    300
attttggtgg ccaccggatt tcaccggcct tcaacgcacg aagaactcgt caataagtat    360
ggtgaagaaa tcgttgctaa tgaagaaatc gtcatgcaca tctcaactga tgatagttca    420
gtggttaaaa ttggccaatt accttcaggt ggcgattgta ttatcaataa aattgctgtt    480
gaagctgact tgttaatttc agaaggtttc attgaatctc atttctttgc cggttttttca   540 ggcggtcgga atcaattct accgggtgtg gcgtcataca aaacaattat ggccaaccac    600
tcaggtgaat ttatcaattc ccattattca agaactggga acttaatgca taatccagtc    660
cacaaggata tggtttacgc tgctaaaaca gccggtctta aatttatttt gaatgttgtt    720
ttggatgaag ataaacatat catcggttct tttgccggta atttagaaac ggcgcacaaa    780
aaaggctgtg acttcgttga agtctatca gaagtcgaca aaattgattg tgacatcgca    840
atttcaacca acggtggtta tccacttgat caaaatatct accaagcggt caagggatg    900 actgctgctg aagccacgaa taacaaggt ggcgtaatta ttatggtcgc tggtgcacgt    960
gatggtcatg gtggcgatgg tttctaccat aatattgccg acgttaaaga tccaaaggaa   1020
ttcttagacc aagcaattaa cacaccacgg cttgaaacgg tgcccgatca atggacgtca   1080
caaattttag ctcgaatttt agtgcaacat cacgtgattt tcgtatcaga tttagttgat   1140
cctcaattaa ttaccgatat gcatatggaa ctggcaacta gtttagatgc tgccttagaa   1200
cgagcctatg caattgaagg tgtggacgca aaagtgactg taatccctga tggtttaggg   1260
gttattgtga aataa                                                    1275

<210> SEQ ID NO 27
<211> LENGTH: 424
<212> TYPE: PRT
<213> ORGANISM: Lactobacillus plantarum
<220> FEATURE:
<221> NAME/KEY: misc_feature
<223> OTHER INFORMATION: LarA amino acid sequence

<400> SEQUENCE: 27

Met Val Ala Ile Asp Leu Pro Tyr Asp Lys Arg Thr Ile Thr Ala Gln
1               5                   10                  15

Ile Asp Asp Glu Asn Tyr Ala Gly Lys Leu Val Ser Gln Ala Ala Thr
            20                  25                  30

Tyr His Asn Lys Leu Ser Glu Gln Glu Thr Val Glu Lys Ser Leu Asp
        35                  40                  45

Asn Pro Ile Gly Ser Asp Lys Leu Glu Glu Leu Ala Arg Gly Lys His
    50                  55                  60

Asn Ile Val Ile Ile Ser Ser Asp His Thr Arg Pro Val Pro Ser His
65                  70                  75                  80

Ile Ile Thr Pro Ile Leu Leu Arg Arg Leu Arg Ser Val Ala Pro Asp
                85                  90                  95

Ala Arg Ile Arg Ile Leu Val Ala Thr Gly Phe His Arg Pro Ser Thr
            100                 105                 110

His Glu Glu Leu Val Asn Lys Tyr Gly Glu Asp Ile Val Asn Asn Glu
        115                 120                 125

Glu Ile Val Met His Val Ser Thr Asp Asp Ser Met Val Lys Ile
    130                 135                 140
```

Gly Gln Leu Pro Ser Gly Gly Asp Cys Ile Ile Asn Lys Val Ala Ala
145                 150                 155                 160

Glu Ala Asp Leu Leu Ile Ser Glu Gly Phe Ile Glu Ser His Phe Phe
                165                 170                 175

Ala Gly Phe Ser Gly Gly Arg Lys Ser Val Leu Pro Gly Ile Ala Ser
            180                 185                 190

Tyr Lys Thr Ile Met Ala Asn His Ser Gly Glu Phe Ile Asn Ser Pro
        195                 200                 205

Lys Ala Arg Thr Gly Asn Leu Met His Asn Ser Ile His Lys Asp Met
210                 215                 220

Val Tyr Ala Ala Arg Thr Ala Lys Leu Ala Phe Ile Ile Asn Val Val
225                 230                 235                 240

Leu Asp Glu Asp Lys Lys Ile Ile Gly Ser Phe Ala Gly Asp Met Glu
                245                 250                 255

Ala Ala His Lys Val Gly Cys Asp Phe Val Lys Glu Leu Ser Ser Val
            260                 265                 270

Pro Ala Ile Asp Cys Asp Ile Ala Ile Ser Thr Asn Gly Gly Tyr Pro
        275                 280                 285

Leu Asp Gln Asn Ile Tyr Gln Ala Val Lys Gly Met Thr Ala Ala Glu
290                 295                 300

Ala Thr Asn Lys Glu Gly Gly Thr Ile Ile Met Val Ala Gly Ala Arg
305                 310                 315                 320

Asp Gly His Gly Gly Glu Gly Phe Tyr His Asn Leu Ala Asp Val Asp
                325                 330                 335

Asp Pro Lys Glu Phe Leu Asp Gln Ala Ile Asn Thr Pro Arg Leu Lys
            340                 345                 350

Thr Ile Pro Asp Gln Trp Thr Ala Gln Ile Phe Ala Arg Ile Leu Val
        355                 360                 365

His His His Val Ile Phe Val Ser Asp Leu Val Asp Pro Asp Leu Ile
370                 375                 380

Thr Asn Met His Met Glu Leu Ala Lys Thr Leu Asp Glu Ala Met Glu
385                 390                 395                 400

Lys Ala Tyr Ala Arg Glu Gly Gln Ala Ala Lys Val Thr Val Ile Pro
                405                 410                 415

Asp Gly Leu Gly Val Ile Val Lys
            420

<210> SEQ ID NO 28
<211> LENGTH: 1275
<212> TYPE: DNA
<213> ORGANISM: Lactobacillus plantarum
<220> FEATURE:
<221> NAME/KEY: misc_feature
<223> OTHER INFORMATION: LarA nucleotide sequence

<400> SEQUENCE: 28
atggttgcaa ttgatttacc atatgacaag cgcacaatta cggctcagat tgatgatgaa      60
aattacgccg gtaagttagt gtcgcaagct gcaacatatc ataacaaatt atcagaacag     120
gaaacggtcg agaagtcgct ggataatcca atcggctccg ataagctgga ggaacttgct     180
cgtgggaagc acaatattgt gattattagt tctgatcaca cgcgcccagt tccttcacat     240
attatcaccc cgatcctatt gcggcggtta cggtcagtgg cgcccgatgc acggattcgg     300
atcctcgtag ctactggttt ccatcggcca tcaacccacg aagaattggt gaataagtat     360
ggtgaagaca tcgtcaataa cgaagaaatc gtgatgcatg tctcaaccga tgacagtagt     420

```
atggtcaaga ttggccaatt accatctggc ggcgattgca ttattaataa ggtcgctgct     480
gaagcagatt tgctaatctc cgaaggcttt atcgaatcac atttctttgc tggttttca     540 ggtggtcgga agtccgtttt acctgggatt gcttcataca agacgattat ggcgaaccat     600
tccggcgaat ttattaactc accgaaggcc cggaccggta atttaatgca taattcgatt     660
cataaggata tggtgtacgc tgctcggacc gctaaacttg cctttattat caatgttgtt     720
ttagacgaag ataaaaaaat cattgggtca tttgccggtg acatggaagc cgcccataaa     780
gtgggctgtg actttgtcaa agaacttcct agtgtaccag ccattgattg tgacattgcg     840
atttcgacga atggtggtta tccgcttgat caaaatattt atcaggccgt aaaggaatg      900 accgctgctg aagcaacaaa caagaaggc ggcacgatta ttatggttgc cggtgctcgt      960
gatggtcacg gttggtgaagg gttttatcac aacttagctg acgttgatga tcctaaggaa   1020
ttcctggacc aagcaatcaa cacgccacgg cttaaaacta ttcctgacca atggacggcc   1080
caaatctttg ctcgaatctt agttcatcat cacgtgattt ttgtgtcaga cctcgttgat   1140
cctgatttga ttacgaatat gcatatggaa ctagccaaga cgttagatga agccatggaa   1200
aaggcctacg cacgcgaggg tcaagccgct aaagtgacgg ttattcctga tggtttaggc   1260
gttattgtga agtag                                                     1275
```

<210> SEQ ID NO 29
<211> LENGTH: 100
<212> TYPE: DNA
<213> ORGANISM: artificial
<220> FEATURE:
<223> OTHER INFORMATION: yafB deletion

<400> SEQUENCE: 29

```
atggctatcc ctgcatttgg tttaggtact ttccgtgtga agacgacgt tgttatttca      60 tctgtgataa cggcgcttgg tgtaggctgg agctgcttcg                          100
```

<210> SEQ ID NO 30
<211> LENGTH: 100
<212> TYPE: DNA
<213> ORGANISM: artificial
<220> FEATURE:
<223> OTHER INFORMATION: yafB deletion

<400> SEQUENCE: 30

```
tcccattcag gagccagacc ttccgggcta accaggcggt cgttgcaatc cagtgcggcg      60
atcgcttttt tatcttcggc catatgaata tcctccttag                           100
```

<210> SEQ ID NO 31
<211> LENGTH: 999
<212> TYPE: DNA
<213> ORGANISM: artificial
<220> FEATURE:
<223> OTHER INFORMATION: Gldgo optimized nucleotide sequence

<400> SEQUENCE: 31

```
atggcaagcg ataccattcg tattccgggt attgatacac cgctgagccg tgttgcactg      60
ggcacctggg caattggtgg ttggatgtgg ggtggtccgg atgatgataa tggtgttcgt     120
accattcatg cagcactgga tgaaggtatt aatctgattg ataccgctcc ggtttatggt     180
tttggtcata gcgaagaaat tgttggtcgt gcactggcag aaaaaccgaa taaagcacat     240
gttgcaacca aactgggtct gcattgggtt ggtgaagatg agaaaaacat gaaagtgttt     300
cgtgatagcc gtccggcacg tattcgtaaa gaagttgaag atagcctgcg tcgtctgcgt     360
```

```
gttgaaacca ttgatctgga acaaattcat tggcctgatg ataaaacccc gattgatgaa    420
agcgcacgtg aactgcagaa actgcatcag gatggtaaaa ttcgtgccct gggtgttagc    480
aattttagtc cggaacaaat ggatatcttt cgtgaagttg caccgctggc aaccattcag    540
cctccgctga acctgtttga acgtaccatt gaaaaagata ttctgccgta tgccgaaaaa    600
cataatgcag ttgttctggc atatggtgca ctgtgtcgtg gtctgctgac cggcaaaatg    660
aatcgtgata ccacctttcc gaaagatgat ctgcgtagca atgatccgaa atttcagaaa    720
ccgaacttcg agaaatatct ggctgcaatg gatgagtttg aaaaactggc cgagaaacgt    780
ggtaaaagcg ttatggcatt tgcagttcgt tgggttctgg atcagggtcc ggttattgca    840
ctgtggggtg cacgtaaacc gggtcaggtt agcggtgtta agatgttttt tggttggagc    900
ctgaccgacg aagaaaaaaa agcagttgat gatattctgg cacgtcatgt tccgaatccg    960
attgatccga cctttatggc accgcctgca cgtgattaa                            999
```

<210> SEQ ID NO 32
<211> LENGTH: 101
<212> TYPE: DNA
<213> ORGANISM: artificial
<220> FEATURE:
<223> OTHER INFORMATION: gldA deletion

<400> SEQUENCE: 32

```
atggaccgca ttattcaatc accgggtaaa tacatccagg gcgctgatgt gattaatcgt     60
ctgggcgaat acctgaagcc gtgtaggctg gagctgcttc g                        101
```

<210> SEQ ID NO 33
<211> LENGTH: 100
<212> TYPE: DNA
<213> ORGANISM: artificial
<220> FEATURE:
<223> OTHER INFORMATION: gldA deletion

<400> SEQUENCE: 33

```
ttattcccac tcttgcagga aacgctgacc gtactggtcg gctaccagca gagcggcgta     60
aacctgatct ggcgtcgcgc catatgaata tcctccttag                          100
```

<210> SEQ ID NO 34
<211> LENGTH: 957
<212> TYPE: DNA
<213> ORGANISM: artificial
<220> FEATURE:
<223> OTHER INFORMATION: gld2 optimized nucleotide sequence

<400> SEQUENCE: 34

```
atggcaagca aaacctatac cctgaataca ggtgcaaaaa ttccggcagt tggttttggc     60
acctttgcaa atgaaggtgc gaaaggtgaa acctatgcag cagttaccaa agcactggat    120
gttggttatc gtcatctgga ttgtgcatgg ttttatcaca atgaagatga agttggtgat    180
gccgttcgtg attttctggc acgtcgtccg gatgttaaac gtgaggacct gtttatttgt    240
accaaagtgt ggaatcatct gcacgaaccg aagatgttta atggtcagc aaaaaatagc    300 tgcgagaacc tgaaagtgga ttatattgac ctgtttctgg ttcattggcc gattgcagca    360
gaaaaaaaca gcgatcgtag cgttaaactg ggtccggatg caaatatgt tattaatcag    420 gcactgaccg aaaatccgga accgacctgg cgtgcaatgg aagaactggt tgaaagcggt    480
ctggttaaag caattggtgt tagcaattgg accattccgg gtctgaaaaa actgctgcag    540
```

```
attgcaaaaa tcaaaccggc agttaaccag attgaaatcc atccgtttct gccgaatgag       600
gaactggtgg cattttgttt tgaaaatggt attctgccgg aagcatatag tccgctgggt       660
agccagaatc aggttccgag cacaggtgaa cgtgttcgtg ataatccgac cctgaaagca       720
gttgcagaac gtagcggtta tagcctggca cagattctgc tggcatgggg actgaaacgt       780
ggttatgttg tgctgccgaa aagcagcacc ccgagccgta ttgaaagcaa tttcaatatt       840
ccggaactga gcgacgaaga ttttgaagca attcagcagg ttgcaaaagg tcgtcatacc       900
cgttttgtga atatgaaaga taccttcggc tataacgttt ggcctgaaga agaataa          957

<210> SEQ ID NO 35
<211> LENGTH: 855
<212> TYPE: DNA
<213> ORGANISM: artificial
<220> FEATURE:
<223> OTHER INFORMATION: Alr1d optimized nucleotide sequence

<400> SEQUENCE: 35
atggcagatg ttggtaaagc aatggttacc ctgagcaatg gtgttcagat gccgcaactg        60
ggtctgggtg tttggcagag tccggcaggc gaagttaccg caaatgcagt taaatgggca       120
ctgtgtgcag gttatcgtca tattgatacc gcagccatct acaaaaatga gaaagcgtt        180 ggtgcaggtc tgcgtgcaag cggtgttccg cgtgaagatg tgtttattac caccaaactg       240
tggaataccg aacagggtta tgaaagcacc ctggcagcat tgaagaaag tcgtcagaaa        300 ctgggtgtgg attatattga tctgtatctg attcattggc ctcgcggtaa agatattgtt       360
agcaaagaag gcaaaaaata cctggatagc tggcgtgcat tgagcaact gtataaagat        420 aaaaaagtgc gtgccattgg cgtgagcaac tttcatattc atcatctgga agatgttctg       480
gccatgtgta ccgttacccc gatggttaat caggttgaac tgcatccgct gaataatcag       540
gcagaactgc gtgccttttg tgatgccaaa caaattaaag ttgaagcatg gtcaccgctg       600
ggtcagggta aactgctgag caatccgatt ctggcagcaa ttggtgcgaa atacaataaa       660
accgcagcac aggttattct cgttggaat attcagaaaa acctgatcac cattccgaaa       720
agcgttcata agaacgcat tgaagaaaac gccgatgtgt tcaatttga actggatgcc        780 gaagatgtga tgagcattga tgcactgaat accaatagcc gttatggtcc tgatccggat       840
gaagcacagt tttaa                                                        855

<210> SEQ ID NO 36
<211> LENGTH: 101
<212> TYPE: DNA
<213> ORGANISM: artificial
<220> FEATURE:
<223> OTHER INFORMATION: frdABCD deletion

<400> SEQUENCE: 36
cgtgcaaacc tttcaagccg atcttgccat tgtaggcgcc ggtggcgcgg gattacgtgc        60
tgcaattgct gccgcgcagg ccatatgaat atcctcctta g                           101

<210> SEQ ID NO 37
<211> LENGTH: 100
<212> TYPE: DNA
<213> ORGANISM: artificial
<220> FEATURE:
<223> OTHER INFORMATION: frdABCD deletion

<400> SEQUENCE: 37
cgttagattg taacgacacc aatcagcgtg acaactgtca ggatagcagc cagaccgtag        60
```

```
aaaacccatt tgcccgcagg tgtaggctgg agctgcttcg                    100
```

<210> SEQ ID NO 38
<211> LENGTH: 103
<212> TYPE: DNA
<213> ORGANISM: artificial
<220> FEATURE:
<223> OTHER INFORMATION: ppsA deletion

<400> SEQUENCE: 38

```
ccaacaatgg ctcgtcaccg ctggtgcttt ggtataacca actcggcatg aatgatgtag    60
acagggttgg gggcaaaaat gcctgtaggc tggagctgct tcg                     103
```

<210> SEQ ID NO 39
<211> LENGTH: 100
<212> TYPE: DNA
<213> ORGANISM: artificial
<220> FEATURE:
<223> OTHER INFORMATION: ppsA deletion

<400> SEQUENCE: 39

```
gccaggctta accaggtttg caccacggtg tccgggttca gagacaggct atcgatcccc    60
tcttccatca accatgcggc catatgaata tcctccttag                         100
```

<210> SEQ ID NO 40
<211> LENGTH: 1554
<212> TYPE: DNA
<213> ORGANISM: artificial
<220> FEATURE:
<223> OTHER INFORMATION: Pct optimized nucleotide sequence

<400> SEQUENCE: 40

```
atgcgtaaag ttgaaattat taccgcagaa caggcagcac agctggttaa agataatgat    60
accattacca gcattggctt tgttagcagc gcacatccgg aagcactgac caaagcactg   120
gaaaaacgtt ttctggatac caatacaccg cagaatctga cctatattta tgcaggtagc   180
cagggtaaac gtgatggtcg tgcagcagaa catctggcac atacaggtct gctgaaacgt   240
gcaattattg gtcattggca gaccgttccg gcaattggta aactggcagt ggaaaataaa   300
attgaagcct ataattttag ccagggcacc ctggttcatt ggtttcgtgc actggcaggt   360
cataaactgg gtgtttttac cgatattggc ctggaaacct ttctggaccc gcgtcagctg   420
ggtggtaaac tgaatgatgt taccaaagag gatctggtta aactgattga agtggatggt   480
catgaacagc tgttttatcc gacctttccg gttaatgttg catttctgcg tggcaccctat   540 gcagatgaaa gcggtaatat acaatggat gaagaaattg gtccgtttga aagcaccagc   600
gttgcacagc agttcataa ttgtggtggt aaagttgtgg ttcaggttaa agatgttgtt   660
gcacatggta gcctggaccc gcgtatggtt aaaattccgg gtatttatgt ggattatgtt   720
gttgttgcag caccggaaga tcatcagcag acctatgatt gtgaatatga tccgagcctg   780
agcggtgaac atcgtgcacc ggaaggtgca gcagatgcag cactgccgat gagcgcaaaa   840
aaaattattg gtcgtcgtgg tgcactggaa ctgaccgaaa atgcagttgt taatctgggt   900
gttggtgcac cggaatatgt tgcaagcgtt gccggtgaag aaggtattgc agataccatt   960
acactgaccg ttgaaggtgg tgcaattggt ggtgttccgc agggtggtgc acgttttggt  1020
agcagccgta tgcagatgc cattattgat cataccctatc agtttgattt ttatgatggt   1080
ggtggcctgg atattgcata tctgggtctg gcacagtgtg atggtagtgg taatattaat  1140
```

```
gtgagcaaat ttggcaccaa tgttgcaggt tgtggtggtt ttccgaatat tagccagcag   1200 acccgaatg tttattttg tggcaccttt accgcaggcg gtctgaaaat tgcagttgaa    1260
gatggcaaag tgaaaattct gcaggaaggc aaagccaaaa aatttattaa agccgtggat   1320
cagattacct ttaatggtag ctatgcagcc cgtaatggta acatgttct gtatattacc    1380 gaacgctgcg tttttgaact gacaaaagaa ggtctgaaac tgatcgaagt tgcaccgggt   1440
attgatattg aaaagatat tctggcccac atggatttta aaccgattat tgataatccg    1500
aaactgatgg atgcccgtct gtttcaggat ggtccgatgg gtctgaaaaa ataa          1554
```

<210> SEQ ID NO 41
<211> LENGTH: 1395
<212> TYPE: DNA
<213> ORGANISM: Salmonella enterica
<220> FEATURE:
<221> NAME/KEY: misc_feature
<223> OTHER INFORMATION: PduP nucleotide sequence

<400> SEQUENCE: 41

```
atgaatactt ctgaactcga aaccctgatt cgcaccattc ttagcgagca attaaccacg    60
ccggcgcaaa cgccggtcca gcctcagggc aaagggattt tccagtccgt gagcgaggcc   120
atcgacgccg cgcaccaggc gttcttacgt tatcagcagt gcccgctaaa aacccgcagc   180
gccattatca gcgcgatgcg tcaggagctg acgccgctgc tggcgcccct ggcggaagag   240
agcgccaatg aaacggggat gggcaacaaa gaagataaat ttctcaaaaa caaggctgcg   300
ctggacaaca cgccgggcgt agaagatctc accaccaccg cgctgaccgg cgacggcggc   360
atggtgctgt ttgaatactc accgtttggc gttatcggtt cggtcgcccc aagcaccaac   420
ccgacggaaa ccatcatcaa caacagtatc agcatgctgg cggcgggcaa cagtatctac   480
tttagcccgc atccgggagc gaaaaaggtc tctctgaagc tgattagcct gattgaagag   540
attgccttcc gctgctgcgg catccgcaat ctggtggtga ccgtggcgga acccaccttc   600
gaagcgaccc agcagatgat ggcccaccag cgaatcgcag tactggccat taccggcggc   660
ccgggcattg tggcaatggg catgaagagc ggtaagaagg tgattggcgc tggcgcgggt   720
aacccgccct gcatcgttga tgaaacggcg gacctggtga agcggcgga agatatcatc   780 aacggcgcgt cattcgatta caacctgccc tgcattgccg agaagagcct gatcgtagtg   840
gagagtgtcg ccgaacgtct ggtgcagcaa atgcaaacct tcggcgcgct gctgttaagc   900
cctgccgata ccgacaaact cgcgccgtc tgcctgcctg aaggccaggc gaataaaaaa    960
ctggtcggca gagcccatc ggccatgctg gaagccgccg ggatcgctgt ccctgcaaaa   1020
gcgccgcgtc tgctgattgc gctggttaac gctgacgatc cgtgggtcac cagcgaacag   1080
ttgatgccga tgctgccagt ggtaaaagtc agcgatttcg ataggcgct ggcgctggcc   1140 ctgaaggttg aagaggggct gcatcatacc gccattatgc actcgcagaa cgtgtcacgc   1200
ctgaacctcg cggcccgcac gctgcaaacc tcgatattgc tcaaaaacgg ccctctcttat  1260 gccgggatcg gcgtcggcgg cgaaggcttt accacttca ctatcgccac accaaccggt    1320
gaagggacca cgtcagcgcg tactttgcc cgttcccggc gctgcgtact gaccaacggc   1380
ttttctattc gctaa                                                    1395
```

<210> SEQ ID NO 42
<211> LENGTH: 939
<212> TYPE: DNA
<213> ORGANISM: Bacillus coagulans
<220> FEATURE:

<221> NAME/KEY: misc_feature
<223> OTHER INFORMATION: Ldh nucleotide sequence

<400> SEQUENCE: 42

```
atgaaaaagg tcaatcgtat tgcagtggtt ggaacgggtg cagttggtac aagttactgc      60
tacgccatga ttaatcaggg tgttgcagaa gagcttgttt taatcgatat taacgaagca     120
aaagcagaag gggaagccat ggacctgaac cacggcctgc catttgcgcc tacgccgacc     180
cgcgtttgga aggcgatta ttccgattgc ggcactgccg atcttgttgt cattacggca     240
ggttccccgc aaaaaccggg cgaaacaagg cttgatcttg tttccaaaaa cgcaaaaatt     300
tttaaaggca tgattaagag catcatggac agcggcttta cgggattttt cttgttgcc     360
agcaacccgg ttgacatttt gacatatgta acttggaaag agtccggcct gccgaaagaa     420
catgttatcg gttcgggcac agtgcttgac tccgcgcgtc tccgcaactc tttgagcgcc     480
caatttggaa ttgacccgcg caatgtgcat gctgcgatta cggcgaaca cggcgatacg     540
gaacttccgg tatggagcca tacaaatatc ggttacgata cgattgaaag ctatctacaa     600
aaaggaatta ttgacgaaaa gacgttagat gacattttg tcaatacgag agatgcggct     660
tatcatatta ttgaacgaaa aggggccaca ttttacggca tcgggatgtc cctgaccccg     720
attacaaggg caatcctgaa caatgaaaac agcgtattga cggtctctgc atttcttgaa     780
ggccaatacg aaacagcga tgtgtacgtt ggcgttccgg ccatcatcaa tcgccagggc     840
atccgtgaag tggttgaaat caaactgaac gaaaagaaac aggaacagtt caatcattct     900
gtaaaagtgc taaagaaac gatggcacct gtattgtaa                             939
```

<210> SEQ ID NO 43
<211> LENGTH: 109
<212> TYPE: DNA
<213> ORGANISM: artificial
<220> FEATURE:
<223> OTHER INFORMATION: gloA reconstruction

<400> SEQUENCE: 43

```
cggttacaaa attgagttaa tcgaagagaa agacgccggt cgcggtctgg gcaactaatc      60
tcctgccggg cgtgaactca tcgcgcccgt gtaggctgga gctgcttcg                 109
```

<210> SEQ ID NO 44
<211> LENGTH: 110
<212> TYPE: DNA
<213> ORGANISM: artificial
<220> FEATURE:
<223> OTHER INFORMATION: gloA reconstruction

<400> SEQUENCE: 44

```
gttgagcgtt atcggacatc tgattctctt aatacggata aattgcagcg cgcattatga      60
caaatattac ttgtcgatgc agtaaagatg catatgaata tcctccttag                110
```

<210> SEQ ID NO 45
<211> LENGTH: 387
<212> TYPE: PRT
<213> ORGANISM: artificial
<220> FEATURE:
<223> OTHER INFORMATION: yqhD*(G149E) amino acid sequence

<400> SEQUENCE: 45

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
```

```
              20                  25                  30
Leu Ile Thr Tyr Gly Gly Gly Ser Val Lys Lys Thr Gly Val Leu Asp
         35                  40                  45

Gln Val Leu Asp Ala Leu Lys Gly Met Asp Val Leu Glu Phe Gly Gly
 50                  55                  60

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                 85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
                115                 120                 125

Ser Ala Ile Pro Met Gly Cys Val Leu Thr Leu Pro Ala Thr Gly Ser
             130                 135                 140

Glu Ser Asn Ala Glu Ala Val Ile Ser Arg Lys Thr Thr Gly Asp Lys
145                 150                 155                 160

Gln Ala Phe His Ser Ala His Val Gln Pro Val Phe Ala Val Leu Asp
                 165                 170                 175

Pro Val Tyr Thr Tyr Thr Leu Pro Pro Arg Gln Val Ala Asn Gly Val
                 180                 185                 190

Val Asp Ala Phe Val His Thr Val Glu Gln Tyr Val Thr Lys Pro Val
             195                 200                 205

Asp Ala Lys Ile Gln Asp Arg Phe Ala Glu Gly Ile Leu Leu Thr Leu
 210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                 245                 250                 255

Gly Ala Gly Val Pro Gln Asp Trp Ala Thr His Met Leu Gly His Glu
             260                 265                 270

Leu Thr Ala Met His Gly Leu Asp His Ala Gln Thr Leu Ala Ile Val
                 275                 280                 285

Leu Pro Ala Leu Trp Asn Glu Lys Arg Asp Thr Lys Arg Ala Lys Leu
             290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                 325                 330                 335

Leu Gly Val Pro Thr His Leu Ser Asp Tyr Gly Leu Asp Gly Ser Ser
             340                 345                 350

Ile Pro Ala Leu Leu Lys Lys Leu Glu Glu His Gly Met Thr Gln Leu
         355                 360                 365

Gly Glu Asn His Asp Ile Thr Leu Asp Val Ser Arg Arg Ile Tyr Glu
370                 375                 380

Ala Ala Arg
385

<210> SEQ ID NO 46
<211> LENGTH: 387
<212> TYPE: PRT
<213> ORGANISM: artificial
<220> FEATURE:
<223> OTHER INFORMATION: yqhD*(T142S) amino acid sequence
```

<400> SEQUENCE: 46

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Ser Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385
```

<210> SEQ ID NO 47

```
<211> LENGTH: 387
<212> TYPE: PRT
<213> ORGANISM: artificial
<220> FEATURE:
<223> OTHER INFORMATION: yqhD*(T142G) amino acid sequence

<400> SEQUENCE: 47
```

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Gly Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 48
<211> LENGTH: 387
<212> TYPE: PRT
<213> ORGANISM: artificial
<220> FEATURE:
<223> OTHER INFORMATION: yqhD*(S144A) amino acid sequence

<400> SEQUENCE: 48

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Thr Gly Val Leu Asp
            35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ala
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
    195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
    275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350
```

```
Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 49
<211> LENGTH: 387
<212> TYPE: PRT
<213> ORGANISM: artificial
<220> FEATURE:
<223> OTHER INFORMATION: yqhD*(G149A) amino acid sequence

<400> SEQUENCE: 49

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Ala Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320
```

Glu Arg Ile Asp Ala Ala Ile Ala Ala Thr Arg Asn Phe Phe Glu Gln
            325                 330                 335

Leu Gly Val Pro Thr His Leu Ser Asp Tyr Gly Leu Asp Gly Ser Ser
        340                 345                 350

Ile Pro Ala Leu Leu Lys Lys Leu Glu Glu His Gly Met Thr Gln Leu
    355                 360                 365

Gly Glu Asn His Asp Ile Thr Leu Asp Val Ser Arg Arg Ile Tyr Glu
370                 375                 380

Ala Ala Arg
385

<210> SEQ ID NO 50
<211> LENGTH: 387
<212> TYPE: PRT
<213> ORGANISM: artificial
<220> FEATURE:
<223> OTHER INFORMATION: yqhD*(G149H) amino acid sequence

<400> SEQUENCE: 50

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala His Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

```
Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 51
<211> LENGTH: 387
<212> TYPE: PRT
<213> ORGANISM: artificial
<220> FEATURE:
<223> OTHER INFORMATION: yqhD*(G149K) amino acid sequence

<400> SEQUENCE: 51

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Lys Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255
```

```
Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
            325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
            370                 375                 380

Ala Ala Arg
385

<210> SEQ ID NO 52
<211> LENGTH: 387
<212> TYPE: PRT
<213> ORGANISM: artificial
<220> FEATURE:
<223> OTHER INFORMATION: yqhD*(G149M) amino acid sequence

<400> SEQUENCE: 52

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
            85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
            130                 135                 140

Glu Ser Asn Ala Met Ala Val Ile Ser Arg Lys Thr Thr Gly Asp Lys
145                 150                 155                 160

Gln Ala Phe His Ser Ala His Val Gln Pro Val Phe Ala Val Leu Asp
            165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220
```

```
Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
            245                 250                 255

Gly Ala Gly Val Pro Gln Asp Trp Ala Thr His Met Leu Gly His Glu
        260                 265                 270

Leu Thr Ala Met His Gly Leu Asp His Ala Gln Thr Leu Ala Ile Val
    275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 53
<211> LENGTH: 387
<212> TYPE: PRT
<213> ORGANISM: artificial
<220> FEATURE:
<223> OTHER INFORMATION: yqhD*(G149T) amino acid sequence

<400> SEQUENCE: 53

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Thr Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190
```

```
Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
210             215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 54
<211> LENGTH: 387
<212> TYPE: PRT
<213> ORGANISM: artificial
<220> FEATURE:
<223> OTHER INFORMATION: yqhD*(G149N) amino acid sequence

<400> SEQUENCE: 54

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Asn Ala Val Ile Ser Arg Lys Thr Thr Gly Asp Lys
145                 150                 155                 160
```

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 55
<211> LENGTH: 387
<212> TYPE: PRT
<213> ORGANISM: artificial
<220> FEATURE:
<223> OTHER INFORMATION: yqhD*(G149R) amino acid sequence

<400> SEQUENCE: 55

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Arg Ala Val Ile Ser Arg Lys Thr Thr Gly Asp Lys
145                 150                 155                 160

Gln Ala Phe His Ser Ala His Val Gln Pro Val Phe Ala Val Leu Asp
            165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 56
<211> LENGTH: 387
<212> TYPE: PRT
<213> ORGANISM: artificial
<220> FEATURE:
<223> OTHER INFORMATION: yqhD*(G149S) amino acid sequence

<400> SEQUENCE: 56

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
        130                 135                 140

Glu Ser Asn Ala Ser Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 57
<211> LENGTH: 387
<212> TYPE: PRT
<213> ORGANISM: artificial
<220> FEATURE:
<223> OTHER INFORMATION: yqhD*(G149V) amino acid sequence

<400> SEQUENCE: 57

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

```
Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                 85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Val Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 58
<211> LENGTH: 387
<212> TYPE: PRT
<213> ORGANISM: artificial
<220> FEATURE:
<223> OTHER INFORMATION: yqhD*(A162I) amino acid sequence

<400> SEQUENCE: 58

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30
```

Leu Ile Thr Tyr Gly Gly Ser Val Lys Thr Gly Val Leu Asp
        35                  40                  45

Gln Val Leu Asp Ala Leu Lys Gly Met Asp Val Leu Glu Phe Gly Gly
 50                  55                  60

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                 85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
        130                 135                 140

Glu Ser Asn Ala Gly Ala Val Ile Ser Arg Lys Thr Thr Gly Asp Lys
145                 150                 155                 160

Gln Ile Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 59
<211> LENGTH: 387
<212> TYPE: PRT
<213> ORGANISM: artificial
<220> FEATURE:
<223> OTHER INFORMATION: yqhD*(A162K) amino acid sequence

<400> SEQUENCE: 59

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
            130                 135                 140

Glu Ser Asn Ala Gly Ala Val Ile Ser Arg Lys Thr Thr Gly Asp Lys
145                 150                 155                 160

Gln Lys Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
                195                 200                 205

Asp Ala Lys Ile Gln Asp Arg Phe Ala Glu Gly Ile Leu Leu Thr Leu
            210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 60
<211> LENGTH: 387
```

```
<212> TYPE: PRT
<213> ORGANISM: artificial
<220> FEATURE:
<223> OTHER INFORMATION: yqhD*(A162D) amino acid sequence

<400> SEQUENCE: 60

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Asp Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380
```

Ala Ala Arg
385

<210> SEQ ID NO 61
<211> LENGTH: 387
<212> TYPE: PRT
<213> ORGANISM: artificial
<220> FEATURE:
<223> OTHER INFORMATION: yqhD*(A162L) amino acid sequence

<400> SEQUENCE: 61

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Leu Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
    370                 375                 380

Ala Ala Arg
385

<210> SEQ ID NO 62
<211> LENGTH: 387
<212> TYPE: PRT
<213> ORGANISM: artificial
<220> FEATURE:
<223> OTHER INFORMATION: yqhD*(A162N) amino acid sequence

<400> SEQUENCE: 62

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Asn Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

```
Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385
```

<210> SEQ ID NO 63
<211> LENGTH: 387
<212> TYPE: PRT
<213> ORGANISM: artificial
<220> FEATURE:
<223> OTHER INFORMATION: yqhD*(V151L) amino acid sequence

<400> SEQUENCE: 63

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Leu Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285
```

```
Leu Pro Ala Leu Trp Asn Glu Lys Arg Asp Thr Lys Arg Ala Lys Leu
    290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
370                 375                 380
Ala Ala Arg
385

<210> SEQ ID NO 64
<211> LENGTH: 387
<212> TYPE: PRT
<213> ORGANISM: artificial
<220> FEATURE:
<223> OTHER INFORMATION: yqhD*(V151M) amino acid sequence

<400> SEQUENCE: 64

Met Asn Asn Phe Asn Leu His Thr Pro Thr Arg Ile Leu Phe Gly Lys
1               5                   10                  15
Gly Ala Ile Ala Gly Leu Arg Glu Gln Ile Pro His Asp Ala Arg Val
            20                  25                  30
Leu Ile Thr Tyr Gly Gly Gly Ser Val Lys Lys Thr Gly Val Leu Asp
        35                  40                  45
Gln Val Leu Asp Ala Leu Lys Gly Met Asp Val Leu Glu Phe Gly Gly
    50                  55                  60
Ile Glu Pro Asn Pro Ala Tyr Glu Thr Leu Met Asn Ala Val Lys Leu
65                  70                  75                  80
Val Arg Glu Gln Lys Val Thr Phe Leu Leu Ala Val Gly Gly Gly Ser
                85                  90                  95
Val Leu Asp Gly Thr Lys Phe Ile Ala Ala Ala Ala Asn Tyr Pro Glu
            100                 105                 110
Asn Ile Asp Pro Trp His Ile Leu Gln Thr Gly Gly Lys Glu Ile Lys
        115                 120                 125
Ser Ala Ile Pro Met Gly Cys Val Leu Thr Leu Pro Ala Thr Gly Ser
    130                 135                 140
Glu Ser Asn Ala Gly Ala Met Ile Ser Arg Lys Thr Thr Gly Asp Lys
145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
Val Asp Ala Phe Val His Thr Val Glu Gln Tyr Val Thr Lys Pro Val
        195                 200                 205
Asp Ala Lys Ile Gln Asp Arg Phe Ala Glu Gly Ile Leu Leu Thr Leu
    210                 215                 220
Ile Glu Asp Gly Pro Lys Ala Leu Lys Glu Pro Glu Asn Tyr Asp Val
225                 230                 235                 240
Arg Ala Asn Val Met Trp Ala Ala Thr Gln Ala Leu Asn Gly Leu Ile
                245                 250                 255
```

-continued

```
Gly Ala Gly Val Pro Gln Asp Trp Ala Thr His Met Leu Gly His Glu
            260             265                 270

Leu Thr Ala Met His Gly Leu Asp His Ala Gln Thr Leu Ala Ile Val
        275             280                 285

Leu Pro Ala Leu Trp Asn Glu Lys Arg Asp Thr Lys Arg Ala Lys Leu
    290             295             300

Leu Gln Tyr Ala Glu Arg Val Trp Asn Ile Thr Glu Gly Ser Asp Asp
305             310             315                 320

Glu Arg Ile Asp Ala Ala Ile Ala Ala Thr Arg Asn Phe Phe Glu Gln
            325             330                 335

Leu Gly Val Pro Thr His Leu Ser Asp Tyr Gly Leu Asp Gly Ser Ser
            340             345             350

Ile Pro Ala Leu Leu Lys Lys Leu Glu Glu His Gly Met Thr Gln Leu
        355             360             365

Gly Glu Asn His Asp Ile Thr Leu Asp Val Ser Arg Arg Ile Tyr Glu
    370             375             380

Ala Ala Arg
385
```

LACTALDEHYDE REDUCTASES FOR THE PRODUCTION OF 1,2-PROPANEDIOL

INTRODUCTION

The present invention relates to new lactaldehyde reductase (LAR) enzymes useful for the production of 1,2-propanediol and to microorganisms overexpressing said enzymes. The invention also relates to a method for producing 1,2-propanediol by converting lactaldehyde into 1,2-propanediol with said enzymes.

1,2-propanediol or propylene glycol, a C3 di-alcohol with formula $C_3H_8O_2$ or HO—CH2-CHOH—CH3, is a widely-used chemical, well-known under its CAS number 57-55-6. It is a colorless, nearly odorless, clear, viscous liquid with a faintly sweet taste, hygroscopic and miscible with water, acetone and chloroform, that is generally used as a component of unsaturated polyester resins, liquid detergents, coolants, anti-freeze and de-icing fluids for aircrafts. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water, employs highly toxic substances and generates by-products such as tert-butanol and 1-phenyl ethanol. Chemical processes further typically lead to the production of a mixture of (R)-1,2-propanediol and (S)-1,2-propanediol, which requires further purification in order to separate said enantiomers.

Natural or synthetic metabolic pathway(s) for 1,2-propanediol production in microorganisms represents an attractive alternative as it alleviates many of the above-mentioned problems.

Up to this day, two natural biological pathways have been characterized for the fermentative production of 1,2-propanediol from sugars in microorganisms.

In the first pathway, functional in *E. coli* under anaerobic conditions, 6-deoxy sugars (e.g. L-rhamnose or L-fucose) are cleaved into dihydroxyacetone phosphate and (S)-lactaldehyde, which can be further reduced into (S)-1,2-propanediol by a 1,2-propanediol oxidoreductase, also called lactaldehyde reductase (LAR) and encoded by the fucO gene (Badia et al., 1985). However, fermentation processes relying on this pathway are not economically viable due to the elevated costs of the deoxyhexoses substrates.

The second natural pathway involves the metabolism of common sugars (e.g. glucose or xylose), including more specifically the glycolysis pathway followed by the methylglyoxal pathway. It converts dihydroxyacetone phosphate into methylglyoxal, which can then be reduced either into (R)-lactaldehyde or hydroxyacetone (acetol). These two compounds are then transformed into (R)-1,2-propanediol. This pathway is typically observed in microorganisms naturally producing (R)-1,2-propanediol, such as *Clostridium sphenoides* and *Thermoanaerobacter thermosaccharolyticum*. However, the production performances exhibited by these organisms are highly limited.

Given that the methylglyoxal pathway is functional in Enterobacteriaceae, several investigations have been conducted to engineer a synthetic pathway for improving the production of 1,2-propanediol using simple carbon sources in said microorganisms, more particularly in *E. coli* (WO 98/37204; Cameron et al., 1998; Altaras and Cameron, 1999; Huang et al., 1999; Altaras and Cameron, 2000; Berrios-Rivera et al., 2003). Improved 1,2-propanediol producing *E. coli* strains obtained by a combination of rational design and evolution have been reported in patent applications WO 2005/073364, WO2008/116848, WO2008/116852, WO2008/116853, WO2010/051849, WO2011/012693, WO2011/012697 and WO2011/012702, which are herein included by reference.

More recently, a new synthetic pathway for the production of 1,2-propanediol proceeding through lactate and involving a lactate coA-transferase, a lactoyl-coA reductase, and the lactaldehyde reductase FucO has been disclosed in WO 2012/172050 and Niu & Guo (2014), incorporated herein by reference. The FucO enzyme employs more particularly NADH as a cofactor, and preferably catalyzes (S)-lactaldehyde thereby mainly producing (S)-1,2-propanediol (Bliksad & Widersten, 2010). A particular disadvantage of this enzyme is its inactivation, under aerobic conditions, by metal-catalyzed oxidation (Cabiscol et al., 1992). The FucO enzyme is therefore not a good candidate for producing 1,2-propanediol through (R)-lactaldehyde and/or under aerobic conditions.

There is thus a need in the art to provide alternative lactaldehyde reductases (LAR), which can act in aerobic and/or anaerobic conditions, on (S)-, (R)- or (R,S)-lactaldehyde, so as to efficiently produce 1,2-propanediol.

The present invention addresses the above discussed needs in the art.

The inventors have indeed surprisingly discovered that enzymes known so far as aldehyde reductases or alcohol dehydrogenases are also capable of using lactaldehyde as a substrate, and thereby of converting said substrate into 1,2-propanediol. The later can be produced either directly into a container in vitro by mere contact of the enzymes according to the invention with lactaldehyde, or by a fermentation process relying on a genetically modified microorganism which recombinantly overexpresses the enzymes according to the invention. The later process can proceed either through the methylglyoxal or the lactate pathway in said microorganism. Based on this discovery, the inventors further designed specific mutants of said enzymes which display an unexpected improved LAR activity compared to the native enzyme.

The present invention therefore provides herein an alternative method for producing 1,2-propanediol, comprising the step of converting (R)-, (S)- and/or (R,S)-lactaldehyde into 1,2-propanediol with at least one enzyme having one or more of the following properties:
  a) a specific lactaldehyde reductase activity of at least 1850 mU/mg towards (R)-lactaldehyde and NADH in anaerobic conditions,
  b) a specific lactaldehyde reductase activity of at least 600 mU/mg towards (R)-lactaldehyde and NADH in aerobic conditions,
  c) a specific lactaldehyde reductase activity of at least 4350 mU/mg towards (S)-lactaldehyde and NADH in aerobic conditions,
  d) a specific lactaldehyde reductase activity of at least 200 mU/mg towards (R)-lactaldehyde and NADPH, and
  e) a specific lactaldehyde reductase activity of at least 150 mU/mg towards (S)-lactaldehyde and NADPH.

Said enzymes are preferably selected among YiaY, GldA, YqhD, YafB, YeaE, YqhE, YdhF, GOX1615, YhdN, Gld2, Alr, functional fragments and functional mutants thereof, and combinations thereof.

The invention also relates to a lactaldehyde reductase consisting of a functional mutant of YqhD, to a nucleic acid encoding said lactaldehyde reductase, to an expression vector comprising said nucleic acid, and to a recombinant microorganism comprising said nucleic acid or said expression vector so as to overexpress said lactaldehyde reductase.

DETAILED DESCRIPTION OF THE INVENTION

It shall be understood that the following detailed description is not limitative and that various modifications, substitutions, omissions, and changes may be made without departing from the scope of the invention. It shall also be understood that the terminology used herein is for the purpose of describing particular embodiments of the invention, and is not intended to be limiting.

All publications, patents and patent applications cited herein, whether supra or infra, are hereby incorporated by reference in their entirety.

Furthermore, unless otherwise stated, all technical and scientific terms used herein have the same meanings as commonly understood by one of ordinary skill in the art. Conventional microbiological and molecular biological techniques are also those well-known and commonly used in the art. Such techniques are well known to the skilled person in the art and are fully explained in the literature.

The singular forms "a", "an", and "the" include plural reference unless the context clearly dictates otherwise.

The terms "comprise", "contain", "involve" or "include" or variations such as "comprises", "comprising", "containing", "involved", "includes", "including" are used herein in an inclusive sense, i.e. to specify the presence of the stated features but not to preclude the presence or addition of further features in various embodiments of the invention.

The term "activity", "catalytic activity" or "function" of an enzyme designates, in the context of the invention, the reaction that is catalyzed by said enzyme for converting its corresponding substrate into another molecule (product). It corresponds to the number of moles of substrate converted per unit time.

The term "specific activity" designates the activity of an enzyme per milligram of protein and can be expressed in μmol of substrate converted per unit time ($min^{-1}$) and per mg of protein ($mg^{-1}$) or $U \cdot mg^{-1}$ where $1 U=1$ $\mu mol \cdot min^{-1}$. It refers more particularly to the amount of product formed by an enzyme in a given amount of time under given conditions per milligram of total proteins, and typically equals to the rate of reaction multiplied by the volume of reaction divided by the mass of total protein. The specific activity can either be measured on the pure enzyme, in which case the amount of protein will be equal to the amount of enzyme, or on a crude extract containing the enzyme, in which case the amount of protein will be the quantity of proteins contained in the crude extract. Methods for quantifying proteins are well known from the man skilled in the art and include as an example the Bradford assay (Bradford, 1976).

The term "catalytic efficiency" of an enzyme designates how efficiently an enzyme converts a substrate into a product.

It is within the skill of the person in the art to measure the above-mentioned activities of an enzyme.

The terms "lactaldehyde reductase activity" or "LAR activity" refer to the activity of reducing an aldehyde function into an alcohol function, i.e. herein of converting a lactaldehyde into 1,2-propanediol. Said activity may be NADPH dependent or NADH dependent (i.e. cofactor dependent), and can occur in aerobic and/or anaerobic conditions. In the context of the present invention, said activity is preferably specific towards a form of lactaldehyde that is (S)-lactaldehyde, (R)-lactaldehyde or (R,S)-lactaldehyde. For illustrative purposes, a specific lactaldehyde reductase activity towards (S)-lactaldehyde means that the substrate (S)-lactaldehyde is preferably reduced over (R)- or (R,S)-lactaldehyde, thereby preferably producing (S)-1,2-propanediol. Lactaldehyde reductase activity and specific activity can be measured as described in Boronat & Aguilar (1979).

Additional definitions are provided throughout the specification.

In a first aspect of the present invention, the present invention is directed to a method for producing 1,2-propanediol, comprising the step of converting (R)-, (S)- and/or (R,S)-lactaldehyde into 1,2-propanediol with at least one enzyme having one or more of the following properties:
  a) a specific lactaldehyde reductase activity of at least 1850 mU/mg towards (R)-lactaldehyde and NADH in anaerobic conditions,
  b) a specific lactaldehyde reductase activity of at least 600 mU/mg towards (R)-lactaldehyde and NADH in aerobic conditions,
  c) a specific lactaldehyde reductase activity of at least 4350 mU/mg towards (S)-lactaldehyde and NADH in aerobic conditions,
  d) a specific lactaldehyde reductase activity of at least 200 mU/mg towards (R)-lactaldehyde and NADPH, and
  e) a specific lactaldehyde reductase activity of at least 150 mU/mg towards (S)-lactaldehyde and NADPH.

In other words, the invention relates to the use of at least one enzyme having one or more of the above listed properties to produce 1,2-propanediol.

It must be noted that enzymes displaying features d) and/or e) can equally act in aerobic and anaerobic conditions.

According to a preferred embodiment, said enzyme is selected from the group consisting of enzymes belonging to the Enzyme Commission classification EC 1.1.1.1, EC 1.1.1.2, EC 1.1.1.6, EC 1.1.1.19, EC 1.1.1.21, EC 1.1.1.55, EC 1.1.1.71, EC 1.1.1.77, EC 1.1.1.156, EC 1.1.1.274 and EC 1.1.1.346.

Preferably, said enzyme is selected among YiaY (SEQ ID NO:3), GldA (SEQ ID NO:5), YqhD (SEQ ID NO:7), YafB (SEQ ID NO:9), YeaE (SEQ ID NO:11), YqhE (SEQ ID NO:13), YdhF (SEQ ID NO:15), GOX1615 (SEQ ID NO:17), YhdN (SEQ ID NO:19), Gld2 (SEQ ID NO:21), Alr (SEQ ID NO:23), functional fragments and functional mutants thereof, and combinations thereof. Information about the corresponding amino-acid and nucleotide sequences, and catalytic properties of said enzymes are provided in Table 1 below. It notably indicates that said enzymes are not known to exhibit a lactaldehyde reductase activity.

According to a preferred embodiment, said enzyme has a specific lactaldehyde reductase activity of at least 1850 mU/mg towards (R)-lactaldehyde and NADH in anaerobic conditions, and a specific lactaldehyde reductase activity of at least 600 mU/mg towards (R)-lactaldehyde and NADH in aerobic conditions, and is selected among GldA, YiaY, functional fragments and functional mutants thereof, and combinations thereof.

According to another preferred embodiment, said enzyme has a specific lactaldehyde reductase activity of at least 4350 mU/mg towards (S)-lactaldehyde and NADH in aerobic conditions, and is selected among GldA, functional fragments and functional mutants thereof, and combinations thereof.

According to another preferred embodiment, said enzyme has a specific lactaldehyde reductase activity of at least 200 mU/mg, preferably of at least 5000 mU/mg and most preferably of at least 10000 mU/mg towards (R)-lactaldehyde and NADPH, and is selected among YafB, YqhE, GOX1615, YhdN, functional fragments and functional mutants thereof, and combinations thereof.

According to another preferred embodiment, said enzyme has a specific lactaldehyde reductase activity of at least 150 mU/mg, preferably of at least 2500 mU/mg and most preferably of at least 5000 mU/mg, towards (S)-lactaldehyde and NADPH in aerobic conditions, and is selected among YafB, YqhE, YhdN, Gld2, functional fragments and functional mutants thereof, and combinations thereof.

The invention encompasses functional fragments and functional mutants of the above listed enzymes.

By "functional fragment" of a protein of reference having a biological activity of interest (i.e. a catalytic activity as defined above), it is meant parts of the amino acid sequence of this reference protein, said parts comprising at least all the regions essential for exhibiting the biological activity of said protein. These parts of sequences can be of various lengths, provided the biological activity of the amino acid sequence of reference is retained by said parts. In other words, the functional fragment of a lactaldehyde reductase is capable herein to reduce an aldehyde function into an alcohol function, and more particularly to convert lactaldehyde into 1,2-propanediol. The capacity of said fragments to exhibit such activity can be assessed as described above. It must however be noted that the activity of said fragments may differ in catalytic efficiency compared to the activity of the lactaldehyde reductases of reference.

By "functional mutants", it is meant herein proteins that structurally differ from the amino acid sequence of a protein of reference but that generally retain all the essential functional characteristics of said protein of reference. A mutant of a protein may be a naturally-occurring mutant or a non-naturally occurring mutant. Such non-naturally occurring mutants of the reference protein can be made, for example, by mutagenesis techniques on the encoding nucleic acids or genes, for example by random mutagenesis or site-directed mutagenesis.

Structural differences may be limited in such a way that the amino acid sequence of reference protein and the amino acid sequence of the mutant may be closely similar overall, and identical in many regions. Structural differences may result from conservative or non-conservative amino acid substitutions, deletions and/or additions between the amino acid sequence of the reference protein and the mutant. The only proviso is that, even if some amino acids are substituted, deleted and/or added, the biological activity of the amino acid sequence of the reference protein is retained by the mutant. That is to say, in the context of the present invention, the functional mutant of a lactaldehyde reductase is capable to reduce an aldehyde function into an alcohol function, and more particularly to convert lactaldehyde into 1,2-propanediol. The capacity of said mutants to exhibit such activity can be assessed as described above. It must however be noted that the activity of said mutants may differ in catalytic efficiency compared to the activity of the lactaldehyde reductases of reference.

"Functional mutants" of lactaldehyde reductases according to the present invention include, but are not limited to, proteins having amino acid sequences which are at least 60% identical after alignment to the amino acid sequence encoding said lactaldehyde reductases of reference. Preferably, said mutants have 60% 70%, 75%, 80%, 85%, 90%, 95% sequence identity to said lactaldehyde reductases, and more preferably have 96%, 97%, 98%, 99%, or 99.999% sequence identity to said lactaldehyde reductases.

Sequence identity between amino acid sequences can be determined by comparing a position in each of the sequences which may be aligned for the purposes of comparison. When a position in the compared sequences is occupied by the same amino acid, then the sequences are identical at that position. A degree of sequence identity between proteins is a function of the number of identical amino acid residues at positions shared by the sequences of said proteins.

To determine the percentage of identity between two amino acid sequences, the sequences are aligned for optimal comparison. For example, gaps can be introduced in the sequence of a first amino acid sequence for optimal alignment with the second amino acid sequence. The amino acid residues at corresponding amino acid positions are then compared. When a position in the first sequence is occupied by the same amino acid residue as the corresponding position in the second sequence, the molecules are identical at that position.

The percentage of identity between the two sequences is a function of the number of identical positions shared by the sequences. Hence % identity=number of identical positions/total number of overlapping positions×100.

Optimal alignment of sequences may be conducted by the global homology alignment algorithm of Needleman and Wunsch (1972), by computerized implementations of this algorithm (such as CLUSTAL W) or by visual inspection. The best alignment (i.e., resulting in the highest percentage of identity between the compared sequences) generated by the various methods is selected.

In other words, the percentage of sequence identity is calculated by comparing two optimally aligned sequences, determining the number of positions at which the identical amino acid occurs in both sequences to yield the number of matched positions, dividing the number of matched positions by the total number of positions and multiplying the result by 100 to yield the percentage of sequence identity.

In the context of the present invention, the functional mutants preferably exhibit an enhanced LAR activity compared to the native enzymes from which they are derived.

Particularly preferred functional mutants of the invention include, without limitation, functional mutants of YqhD (YqhD*) which comprise at least one amino acid mutation selected from the group consisting of T142G (threonine replaced by a glycine), T142S, (threonine replaced by a serine), S144A (serine replaced by an alanine), G149A (glycine replaced by an alanine), G149E (glycine replaced by a glutamate), G149H (glycine replaced by a histidine), G149K (glycine replaced by a lysine), G149T (glycine replaced by a threonine), G149N (glycine replaced by an asparagine), G149R (glycine replaced by an arginine), G149S (glycine replaced by a serine), V151M (valine replaced by a methionine), V151L (valine replaced by a leucine), A162K (alanine replaced by a lysine), A162D (alanine replaced by an aspartate), A162L (alanine replaced by a leucine), A162N (alanine replaced by an asparagine), and combinations thereof, the amino acids numbers being made by reference to the YqhD *E. coli* amino acid sequence (SEQ ID NO:7).

In a preferred embodiment, the functional mutant of YqhD according to the invention comprises at least the amino acid mutation G149K, in order to produce (R)-1,2-propanediol. Said mutant is preferably of sequence SEQ ID NO:51.

In another preferred embodiment, the functional mutant of YqhD according to the invention comprises at least the amino acid mutation V151L, in order to produce (S)-1,2-propanediol. Said mutant is preferably of sequence SEQ ID NO:63.

It must be noted that this is the first report herein of the above described mutants exhibiting a lactaldehyde reductase activity. Accordingly, the invention further encompasses a lactaldehyde reductase consisting of a functional mutant of YqhD as described above; a nucleic acid encoding said lactaldehyde reductase; an expression vector comprising said nucleic acid; and a recombinant microorganism comprising at least one of said nucleic acid or at least one of said expression vector so as to overexpress said lactaldehyde reductase. Details and preferred embodiments regarding said microorganism are provided further below.

reductase activity as described above. To do so, the method according to the invention preferably comprises the steps of:
i) providing a solution containing (R)-, (S)- and/or (R,S)-lactaldehyde and NADPH;
ii) heating said solution in vitro;
iii) contacting the solution of step ii) in vitro with at least one enzyme having a lactaldehyde reductase activity as described above;
thereby providing a solution comprising 1,2-propanediol.

To do so, the lactaldehyde reductase enzyme according to the invention can be freely mixed in the solution containing the substrates R)-, (S)- and/or (R,S)-lactaldehyde and NADPH, or can be immobilized by an attachment to an inert, insoluble material and contacted with said solution.

TABLE 1

LAR enzymes according to the invention - except for the FuCO enzyme, which is sensitive to oxygen, the activity (mUI/mg) of the LAR enzymes below is the activity measured in aerobia conditions.

| Name | Microorganism | Known function | Uniprot Reference | Protein SEQ ID NO: | Gene SEQ ID NO: | Cofactor | R-LAR (mUI/mg) | S-LAR (mUI/mg) |
|---|---|---|---|---|---|---|---|---|
| FuCO | E. coli | Lactaldehyde reductase (EC: 1.1.1.77) | P0A9S1 | 1 | 2 | NADH | 1835 (anaerobia) 593 (aerobia) | 19362 (anaerobia) 4313 (aerobia) |
| YiaY | E. coli | Putative alcohol dehydrogenase (EC: 1.1.1.1) | P37686 | 3 | 4 | NADH | 4175 | 4199 |
| GldA | E. coli | Glycerol dehydrogenase (EC: 1.1.1.6) | P0A9S5 | 5 | 6 | NADH | 46891 | 13827 |
| YqhD | E. coli | Alcohol dehydrogenase YqhD (EC: 1.1.1.—) | Q46856 | 7 | 8 | NADPH | 234 | 627 |
| YqhD* (G149E) | artificial | — | — | 45 | — | NADPH | 238 | 1654 |
| YafB | E. coli | 2,5-diketo-D-gluconic acid reductase B (EC: 1.1.1.346) | P30863 | 9 | 10 | NADPH | 6698 | 2959 |
| YeaE | E. coli | Uncharacterized protein YeaE | P76234 | 11 | 12 | NADPH | 241 | 206 |
| YqhE | E. coli | 2,5-diketo-D-gluconic acid reductase A (EC: 1.1.1.274) | Q46857 | 13 | 14 | NADPH | 6768 | 4527 |
| YdhF | E. coli | Oxidoreductase YdhF (EC: 1.—.—.—) | P76187 | 15 | 16 | NADPH | 537 | 196 |
| GOX1615 | Gluconobacter oxydans | Putative oxidoreductase (EC: 1.1.1.—) | Q5FQJ0 | 17 | 18 | NADPH | 23594 | 1555 |
| YhdN | Bacillus subtilis | General stress protein 69 (EC: 1.1.1.—) | P80874 | 19 | 20 | NADPH | 6880 | 5751 |
| Gld2 | Hypocrea jecorina | Glycerol 2-dehydrogenase (NADP(+)) (EC: 1.1.1.156) | Q0GYU4 | 21 | 22 | NADPH | 4875 | 2638 |
| Alr | Leishmania donovani | Prostaglandin f2-alpha synthase | A4UTP6 | 23 | 24 | NADPH | 1512 | 1453 |

The above method can be performed either directly into a container in vitro by mere contact of the enzyme(s) having lactaldehyde reductase activity according to the invention with lactaldehyde, or by a fermentation process relying on a genetically modified microorganism which recombinantly overexpresses said enzyme(s).

Accordingly, in a preferred embodiment, the conversion of (R)-, (S)- and/or (R,S)-lactaldehyde into 1,2-propanediol is made by contacting in vitro a solution comprising said lactaldehyde with at least one enzyme having a lactaldehyde In a preferred embodiment, the above method can also comprise a further step of regenerating NADPH by introducing a coupling reaction with at least one other enzyme and substrate thereof.

Finally, in a preferred embodiment, the above method can comprise a further step of recovering 1,2-propanediol from the solution, or in other words of collecting the produced 1,2-propanediol.

It is within the skill of the person in the art to adjust the pH of the solution of step i) and the heating temperature of step ii) to maximize 1,2-propanediol output, to select another enzyme and substrate for a coupling reaction, and/or to recover said product so as to maximize its purity.

In another preferred embodiment, the conversion of (R)-, (S)- and/or (R,S)-lactaldehyde into 1,2-propanediol is made by culturing a recombinant microorganism in a culture medium comprising a source of carbon, wherein said microorganism is genetically modified to comprise at least one pathway for the production of (R), (S) and/or (R,S) lactaldehyde and the conversion thereof into 1,2-propanediol.

In other words, according to this preferred embodiment, the method according to the invention relates to a fermentation method for the production of 1,2-propanediol comprising at least the step of culturing a recombinant microorganism in a culture medium comprising a carbon source, wherein said microorganism is genetically modified to comprise at least one pathway for the production of (R), (S) and/or (R,S) lactaldehyde and the conversion thereof into 1,2-propanediol.

It shall be understood that the genetic modification for the conversion of lactaldehyde into 1,2-propanediol is preferably an overexpression of at least one enzyme of the invention having a lactaldehyde reductase activity.

The above method can comprise a further step of recovering 1,2-propanediol from the culture medium, or in other words of collecting the produced 1,2-propanediol. The action of "recovering 1,2-propanediol from the culture medium" designates the action of recovering 1,2-propanediol from the fermentation medium whatever its purity degree. "Recovering" means recovering the first product directly obtained from the fermentative process (fermentation must) which contains the product of interest (in this case 1,2-propanediol) and other co-products of the fermentation so with a more or less acceptable purity degree.

The above method can also comprise a further step of purifying 1,2-propanediol if the purity degree obtained after the step of recovering is less acceptable. The "purifying" step consists of specifically purify the product of interest (in this case 1,2-propanediol) in order to obtain said product of interest with an improved purity degree that is to say by eliminating all the co-products.

1,2-propanediol can be recovered and purified by techniques and means well known by the man skilled in the art which have notably been described in patent applications WO2011/076690 and WO2012/130316, herein incorporated by reference.

The terms "fermentative process", "fermentation" or "culture" are used herein interchangeably to denote the growth of a microorganism. This growth is generally conducted in fermenters with an appropriate growth medium adapted to the microorganism being used.

A "culture medium" designates a medium (e.g., sterile, liquid media) comprising nutrients essential or beneficial to the maintenance and/or growth of a cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "source of carbon", "carbon source" or "carbon substrate" according to the present invention refers to any carbon source capable of being metabolized by a microorganism wherein the substrate contains at least one carbon atom.

The term "carbohydrate" refers to any carbon source capable of being metabolized by a microorganism and containing at least one carbon atom, two atoms of hydrogen and one atom of oxygen. Examples of carbohydrates include, without limitation, monosaccharides such as glucose, fructose, mannose, xylose, arabinose, galactose and the like; disaccharides such as sucrose, cellobiose, maltose, lactose and the like; oligosaccharides such as raffinose, stacchyose, maltodextrins and the like; polysaccharides such as cellulose, hemicellulose, starch and the like, methanol, formaldehyde and glycerol. Particularly preferred carbohydrates according to the invention are arabinose, fructose, galactose, glucose, lactose, maltose, sucrose, xylose and any mixture thereof. More preferably, the carbon source according to the invention is sucrose.

In a preferred embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

The person skilled in the art can easily determine the culture conditions necessary for growing the microorganism according to the invention. In particular, it is well know that bacteria can be fermented at a temperature comprised between 20° C. and 55° C., preferentially between 25° C. and 40° C. *E. coli* can more particularly be cultured at a temperature comprised between about 30° C. and about 37° C.

The method of the invention can be performed either in a batch process, in a fed-batch process or in a continuous process, and under aerobic, micro-aerobic or anaerobic conditions.

A fermentation "under aerobic conditions" means that oxygen is provided to the culture by dissolving gas into the liquid phase of the culture. This can be achieved by (1) sparging oxygen containing gas (e.g. air) into the liquid phase, or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes, thereby improving the general metabolism of the strain.

Micro-aerobic conditions can be used herein and are defined as culture conditions wherein low percentages of oxygen (e.g. using a mixture of gas containing between 0.1 and 10% of oxygen, completed to 100% with nitrogen) are dissolved into the liquid phase.

By contrast, "anaerobic conditions" are defined as culture conditions wherein no oxygen is provided to the culture medium. Strictly anaerobic conditions can be obtained by sparging an inert gas like nitrogen into the culture medium to remove traces of other gas. Nitrate can be used as an electron acceptor to improve ATP production by the strain and improve its metabolism.

The term "microorganism", as used herein, refers to a living microscopic organism, which may be a single cell or a multicellular organism and which can generally be found in nature. In the context of the present invention, the microorganism is preferably a bacterium, yeast or fungus. More preferably, the microorganism of the invention is selected among Enterobacteriaceae, Bacillaceae, Clostridiaceae, Corynebacteriaceae, Streptomycetaceae, and yeast. Even more preferably, the microorganism of the invention is a species of *Escherichia*, *Corynebacterium*, *Klebsiella*, *Thermoanaerobacterium*, *Clostridium* or *Saccharomyces*. Yet, even more preferably, the microorganism of the invention is selected from *Escherichia coli*, *Corynebacterium glutamicum*, *Klebsiella pneumoniae*, *Thermoanaerobacterium thermosaccharolyticum*, *Clostridium* or *Saccharomyces*. Most preferably, the microorganism of the invention is *Escherichia coli*.

The term "recombinant microorganism", "genetically modified microorganism", or "genetically engineered microorganism", as used herein, refers to a microorganism as defined above that is not found in nature and therefore genetically differs from its natural counterpart. In other words, it refers to a microorganism that is modified by introduction and/or by deletion and/or by modification of its genetic elements. Such modification can be performed by genetic engineering, by forcing the development and evolution of new metabolic pathways by culturing the microorganism under specific selection pressure, or by combining both methods (see, e.g. WO2005/073364 or WO2008/116852).

A microorganism genetically modified to comprise a pathway for the production of (R), (S) and/or (R,S) lactaldehyde and its conversion into 1,2-propanediol means that said microorganism is a recombinant microorganism as defined above that is capable of producing (R), (S) and/or (R,S) lactaldehyde and converting said lactaldehyde into 1,2-propanediol. In other words, said microorganism has been genetically modified to allow production of 1,2-propanediol through the conversion of (R), (S) and/or (R,S) lactaldehyde.

As further explained below, the microorganism of the invention can be genetically modified by modulating the expression level of one or more endogenous genes, and/or by expressing one or more heterologous genes in said microorganism.

By "gene", it is meant herein a nucleic acid molecule or polynucleotide that codes for a particular protein (i.e. polypeptide) such as an enzyme, or in certain cases, for a functional or structural RNA molecule. In the context of the present invention, the genes referred herein encode enzymes. Genes according to the invention are either endogenous genes or exogenous. By "endogenous gene", it is meant herein that said gene is naturally present in the microorganism, while the term "exogenous gene" (or alternatively, "heterologous gene" or "transgene") refers to a gene is not naturally occurring in the microorganism.

In the context of the present invention, should the microorganism be genetically modified to "modulate" the expression level of one or more endogenous genes, it is meant herein that the expression level of said gene is up-regulated (overexpressed), downregulated (i.e. attenuated or underexpressed), or even completely abolished by comparison to its natural expression level. Such modulation can therefore result in an enhancement of the activity of the gene product, or alternatively, in a lower or null activity of the endogenous gene product.

An endogenous gene can be overexpressed by introducing heterologous sequences which favour upregulation in addition to endogenous regulatory elements or by substituting those endogenous regulatory elements with such heterologous sequences, or by introducing one or more supplementary copies of the endogenous gene into the chromosome or a plasmid within the microorganism. Endogenous gene activity and/or expression level can also be modified by introducing mutations into their coding sequence to modify the gene product. A deletion of an endogenous gene can also be performed to inhibit totally its expression within the microorganism. Another way to modulate the expression of an endogenous gene is to exchange its promoter (i.e. wild type promoter) with a stronger or weaker promoter to up or down regulate the expression level of this gene. Promoters suitable for such purpose can be homologous or heterologous and are well-known in the art. It is within the skill of the person in the art to select appropriate promoters for modulating the expression of an endogenous gene.

In addition, or alternatively, the microorganism of the invention can be genetically modified to express one or more exogenous genes, provided that said genes are introduced into the microorganism with all the regulatory elements necessary for their expression in the host microorganism. The modification or "transformation" of microorganisms with exogenous DNA is a routine task for those skilled in the art. In the context of the present invention, the term "overexpression" or "overexpressing" is also used herein in relation to the expression of exogenous genes in the microorganism.

In order to express an exogenous gene in a microorganism, such gene can be directly integrated into the microorganism chromosome, or be expressed extra-chromosomally by plasmids or vectors within the microorganism. A variety of plasmids, which differ in respect of their origin of replication and of their copy number in a cell, are well known in the art and can be easily selected by the skilled practitioner for such purpose. Exogenous genes according to the invention are advantageously homologous genes.

In the context of the invention, the term "homologous gene" or "homolog" not only refers to a gene inherited by two species (i.e. microorganism species) by a theoretical common genetic ancestor, but also includes genes which may be genetically unrelated that have, nonetheless, evolved to encode proteins, such as enzymes, which perform similar functions and/or have similar structure (i.e. functional homolog). Therefore, the term "functional homolog" refers herein to a gene that encodes a functionally homologous protein.

Using the information available in databases such as Uniprot (for proteins), Genbank (for genes), or NCBI (for proteins or genes), those skilled in the art can easily determine the sequence of a specific protein and/or gene of a microorganism, and identify based on this sequence the one of equivalent genes, or homologs, in another microorganism. This routine work can be performed by a sequence alignment of a specific gene sequence of a microorganism with gene sequences or the genome of other microorganisms, which can be found in the above mentioned databases. Such sequence alignment can advantageously be performed using the BLAST algorithm developed by Altschul et al. (1990). Once a sequence homology has been established between those sequences, a consensus sequence can be derived and used to design degenerate probes in order to clone the corresponding homolog gene of the related microorganism. These routine methods of molecular biology are well known to those skilled in the art.

It shall be further understood that, in the context of the present invention, should an exogenous gene encoding an enzyme of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described in Graf et al. (2000), Deml et al. (2001) or Davis & Olsen (2011). Several softwares have been developed for codon optimization determination such as the GeneOptimizer® software (Lifetechnologies) or the OptimumGene™ software (GenScript).

In other words, the exogenous gene encoding a protein of interest is preferably codon-optimized for expression in a specific microorganism.

The microorganism according to the invention can also be genetically modified to increase or decrease the activity of one or more proteins, notably enzymes.

The activity of an enzyme as described above can be enhanced so as to increase the yield of the reaction, i.e. the yield in product.

The terms "increased activity" or "enhanced activity" of an enzyme compared to the non-modified enzyme designates either an increased specific catalytic activity of the enzyme and/or an increased specificity for its substrate, and/or an increased concentration/availability of the enzyme in a cell.

Increasing an activity can be achieved by improving the protein catalytic efficiency or decreasing protein (i.e. enzyme) turnover, by decreasing messenger RNA (mRNA) turnover, by increasing transcription of a gene coding for said enzyme, or by increasing translation of the mRNA.

Improving the protein catalytic efficiency means increasing the kcat and/or decreasing the Km for a given substrate and/or a given cofactor, and/or increasing the Ki for a given inhibitor. Kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well-known to the skilled person in the art. Those include rational engineering with sequence and/or structural analysis and directed mutagenesis, as well as random mutagenesis and screening. Mutations can be introduced by site-directed mutagenesis by conventional methods such as Polymerase Chain Reaction (PCR), by random mutagenesis techniques, for example via mutagenic agents (Ultra-Violet rays or chemical agents like nitrosoguanidine (NTG) or ethylmethanesulfonate (EMS)) or DNA shuffling or error-prone PCR. Stabilizing the protein can also be achieved by adding a "tag" peptide sequence either at the N-terminus or the C-terminus of the protein. Such tags are well known in the art, and include, among others, the Glutathione-S-Transferase (GST).

Decreasing mRNA turnover can be achieved by modifying the gene sequence of the 5'-untranslated region (5'-UTR) and/or the coding region, and/or the 3'-UTR (Carrier and Keasling, 1999).

Increasing the transcription of a gene, whether endogenous or exogenous, can be achieved by increasing the number of its copies within a microorganism expressing said gene and/or by using a promoter leading to a higher level of expression of the gene compared to the wild type promoter. In the context of the present invention, the term "overexpression" or "overexpressing" is also used to designate an increase in transcription of a gene in a microorganism.

As indicated above, to increase the number of copies of a gene in a microorganism, said gene can be encoded chromosomally or extra-chromosomally. When the gene of interest is to be encoded on the chromosome, several copies of the gene can be introduced on the chromosome by methods of genetic recombination, which are well-known to in the art (e.g. gene replacement). When the gene is to be encoded extra-chromosomally in the microorganism, it can be carried by different types of plasmid that differ in respect to their origin of replication depending on the microorganism in which they can replicate, and by their copy number in the cell. The microorganism transformed by said plasmid can contain 1 to 5 copies of the plasmid, or about 20 copies of it, or even up to 500 copies of it, depending on the nature of the plasmid. Examples of low copy number plasmids which can replicate in *E. coli* include, without limitation, the pSC101 plasmid (tight replication), the RK2 plasmid (tight replication), as well as the pACYC and pRSF1010 plasmids, while an example of high copy number plasmid which can replicate in *E. coli* is pSK bluescript II.

Promoters which can increase the expression level of a gene are also well-known to the skilled person in the art, and can be homologous (originating from same species) or heterologous (originating from a different species). Examples of such promoters widely used for such purpose include, without limitation, the promoters Ptrc, Ptac, and P/ac, as well as the lambda promoters $P_R$ and $P_L$. These promoters can also be induced ("inducible promoters") by a particular compound or by specific external condition like temperature or light.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, to proportionally alter its production rate, and control its activity inside the cell. It is also possible to optimize the strength of a RBS sequence to achieve a targeted translation initiation rate by using the software RBS CALCULATOR (Salis, 2011). It is within the skill of the person in the art to select the RBS sequence based on the nature of the mRNA.

As stated above, the microorganism is genetically modified to comprise at least one pathway for the production of (R), (S) and/or (R,S) lactaldehyde and the conversion thereof into 1,2-propanediol. In such case, lactaldehyde is thus used as an intermediate obtained from the catabolism of a carbon source, so as to produce 1,2-propanediol.

Synthetic pathways involving the catabolism of different carbon sources into 1,2-propanediol are well-known to the skilled person, and have notably been described in patent applications WO 2005/073364, WO 2008/116848, WO 2008/116853, WO 2011/012693, WO 2011/012697, WO 2011/012702 and EP2532751, which are incorporated herein by reference.

Two main pathways allowing the microbial production of 1,2-propanediol, and involving lactaldehyde as an intermediate, are the methylglyoxal pathway and the pyruvate pathway, which are both described in FIG. 1. In the context of the present invention, said pathways can be combined in the microorganism.

In the first pathway, dihydroxyacetone phosphate (DHAP) can be converted into methylglyoxal with the methylglyoxal synthase.

In microorganisms and in particular in *Escherichia coli*, three pathways of methylglyoxal degradation have been identified:

the first system is the degradation of methylglyoxal by a methylglyoxal reductase into hydroxyacetone also named acetol (Cameron et al, 1998, Bennett and San, 2001), the second system is the reduction of methylglyoxal by a methylglyoxal reductase into (R)- or (S)-lactaldehyde (Cameron et al, 1998, Bennett and San, 2001), and the third system is the conversion of methylglyoxal into R-lactate by the glyoxalases systems (Cooper, 1984 and Misra et al, 1995).

It is known to the skilled person in the art that methylglyoxal reductases can lead to the concomitant production of hydroxyacetone and lactaldehyde.

From the first system (degradation of methylglyoxal into hydroxyacetone), hydroxyacetone can be reduced into 1,2-propanediol by hydroxacetone reductase. In this case the preferred genetic modifications are the following and described in the patent application WO 2008/116848, WO 2008/116853, WO 2011/012693, WO 2011/012697, WO 2011/012702 or EP2532751 incorporated by herein reference:

increased expression of at least one gene selected among mgsA gene encoding methylglyoxal synthase, yqhD, yafB, ycdW, yqhE, yeaE, yghZ, yajO, tas, ydjG or ydbC genes encoding methylglyoxal reductase, gldA gene encoding glycerol dehydrogenase and fucO gene encoding lactaldehyde reductase;

deletion of either the edd gene encoding phosphogluconate dehydratase or eda gene encoding 2-keto-3-deoxy-gluconate 6-phosphate aldolase or both;

attenuation of the synthesis of unwanted by-products by deletion of the genes coding for enzymes involved in synthesis of lactate from methylglyoxal (such as gloA encoding glyoxalase I, aldA encoding aldehyde dehydrogenase A, aldB encoding acetaldehyde dehydrogenase), lactate from pyruvate (ldhA encoding lactate dehydrogenase), formate (pflA encoding pyruvate formate-lyase activating enzyme, pflB encoding pyruvate formate-lyase), ethanol (adhE encoding aldehyde-alcohol dehydrogenase) and acetate (ackA encoding acetate kinase, pta encoding phosphate acetyltransferase, poxB encoding pyruvate oxidase);

elimination of the pathways consuming PEP like pyruvates kinases (encoded by the pykA and pykF genes) and/or by promoting the synthesis of PEP e. g. by overexpressing the ppsA gene coding for PEP synthase;

specific mutation in the/pd gene encoding lipoamide dehydrogenase;

the arcA gene encoding ArcA transcriptional dual regulator and the ndh gene encoding NADH:ubiquinone oxidoreductase II can be deleted, the gapA gene encoding glyceraldehyde 3-phosphate dehydrogenase is under the control of temperature inducible promoter, genes involved in the importation and metabolism of sucrose (cscB gene encoding sucrose permease, cscA gene encoding sucrose hydrolase, cscK gene encoding fructokinase, scrA gene encoding EnzymeI of the phosphoenolypyruvate-dependent phosphotransferase system, scrK gene encoding ATP-dependent fructokinase, scrB gene encoding sucrose 6-phosphate hydrolase (invertase), scrY gene encoding sucrose porine) are added or their expression is increased.

A preferred genetic modification is the improvement of methylglyoxal reductase activity, obtained by an increased expression of the gene yqhD*(G149E).

Another preferred genetic modification is the improvement of methylglyoxal synthase activity, obtained by an increased expression of the gene mgsA*(H21Q).

Another preferred genetic modification is the improvement of hydroxyacetone reductase activity, obtained by an increased expression of the gene gldA*(A160T) or by an increased expression of the gene adh from *Clostridium beijerinckii*.

From the second system, lactaldehyde can be reduced into 1,2-propanediol by an enzyme having a lactaldehyde reductase activity as described above.

Accordingly, in a preferred embodiment, the genetic modification in said microorganism for the production of (R), (S) and/or (R,S) lactaldehyde is an overexpression of at least one the following enzymes:
methylglyoxal synthase;
methylglyoxal reductase; and
any combination thereof.

From the third system (conversion of methylglyoxal into R-lactate), lactate can be further transformed into pyruvate by lactate dehydrogenases. (R)-lactate or (S)-lactate can also be converted into (R)-lactaldehyde or (S)-lactaldehyde, as described in patent WO2012/172050, via a lactate coA-transferase and a lactoyl-coA reductase.

Accordingly, in a preferred embodiment, the genetic modification in said microorganism for the production of (R), (S) and/or (R,S) lactaldehyde is an overexpression of at least one the following enzymes:
methylglyoxal synthase;
glyoxalase;
lactate dehydrogenase;
lactate coA-transferase;
lactoyl-coA reductase; and
any combination thereof.

Lactate coA-transferase can be encoded by the pct gene from *Clostridium propionicum*, the pct gene from *Megasphaera elsdenii* or the cat1 gene from *Clostridium kluyveri*. Lactoyl-coA reductase can be encoded by the sucD gene from *Clostridium kluyveri*, the Msed_0709 gene from *Metallosphaera sedula* DSM5348, the mcr gene from *Sulfolobus tokodaii*, the pduP gene from *Salmonella typhimurium*, the mcr gene from *Chloroflexus aurantiacus*, the aldh gene from *Clostridium beijerinckii* or the dmpF gene from *Pseudomonas*.

In the second pathway, pyruvate can be converted into lactate with a lactate dehydrogenase. Lactate can then be converted into the intermediate lactaldehyde, as described in patent application WO2012/172050, via a lactate coA-transferase and a lactoyl-coA reductase.

Accordingly, in a preferred embodiment, the genetic modification in said microorganism for the production of (R), (S) and/or (R,S) lactaldehyde is an overexpression of at least one the following enzymes:
lactate dehydrogenase;
lactate coA-transferase;
lactoyl-coA reductase; and
any combination thereof.

Preferred genes encoding lactate coA-transferases and lactoyl-coA reductases are as described above.

The skilled person in the art would readily understand that enzymes of the first pathway as described above, or of the first and second pathways, can be combined, so as to maximize the output of 1,2-propanediol.

Thus, according to a preferred embodiment, the genetic modification in said microorganism for the production of (R), (S) and/or (R,S) lactaldehyde is an overexpression of at least one the following enzymes:
methylglyoxal synthase;
methylglyoxal reductase;
glyoxalase;
lactate dehydrogenase;
lactate coA-transferase;
lactoyl-coA reductase; and
any combination thereof.

Figure 2:
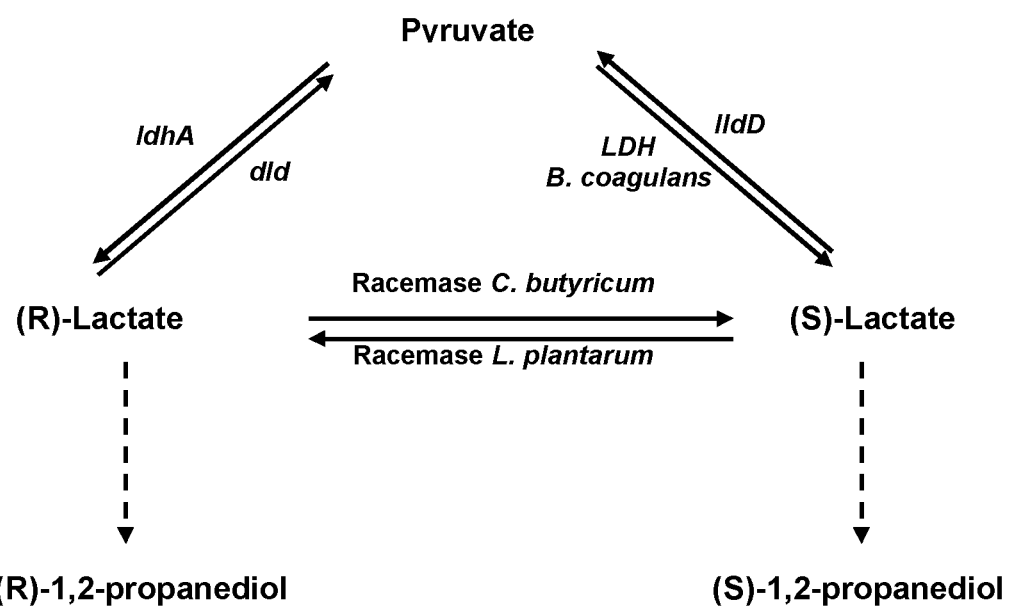

Each of the two stereoisomers (R)-1,2-propanediol and (S)-1,2-propanediol may be of interest for applications requiring for example specific chiral starting materials in specialized chemicals and pharmaceutical products. The conversion of (R)-lactaldehyde into (R)-1,2-propanediol or the conversion of (S)-lactaldehyde into (S)-1,2-propanediol by equally using (R)-lactate or (S)-lactate as the intermediate can notably be genetically engineered in the microorganism. To do so, a racemase can be overexpressed to allow the conversion between (R)-lactate and (S)-lactate or between (S)-lactate and (R)-lactate, as shown in FIG. 2.

Accordingly, in a preferred embodiment, the microorganism is further genetically modified to allow the conversion of (R)-lactate into (S)-lactate, and/or of (S)-lactate into (R)-lactate. Preferably, said genetic modification is an overexpression of at least one lactate racemase, which may be selected from lactate racemases of *Clostridium butyricum*, *Lactobacillus plantarum*, *Megasphaera elsdenii* or *Lactobacillus sakei* (Desguin et al, 2014a and b, Goffin et al, 2005, Cantwell et al, 1974, Hino et al, 1993, Hiyama et al, 1968 and Pepple et al, 1976).

Particularly preferred lactate racemases according to the invention are described in Table 2 below.

TABLE 2

Lactate racemases according to the invention

| Name | Organism | Function | Uniprot Reference | Protein SEQ ID NO: | Gene SEQ ID NO: |
|---|---|---|---|---|---|
| LarA | *Lactobacillus sakei* | Lactate racemase allowing the conversion of (R)-lactate into (S)-lactate | A0A095ABC4 | 25 | 26 |
| LarA | *Lactobacillus plantarum* | Lactate racemase allowing the conversion of (S)-lactate into (R)-lactate | F9USS9 | 27 | 28 |

The microorganism as described above can also be further modified to favour a pathway producing (R)-lactate or (S)-lactate from pyruvate as described in FIG. 2.

To do so, the dld and lldD genes, both encoding lactate dehydrogenases, or the ldhA, dld and lldD genes can be deleted in the microorganism.

Accordingly, in a preferred embodiment, the microorganism is further genetically modified to favour the production of (R)-lactate or the production of (S)-lactate. Preferably said genetic modification is a deletion of at least one gene selected from the group consisting of the genes dld, lldD, ldhA, dld, lldD, and any combination thereof.

In order to obtain (S)-lactate from pyruvate, and hence favour the production of (S)-1,2-propanediol, the deletion of the dld gene and/or the lldD gene can be preferably combined with an overexpression of at least one lactate racemase as defined above, such as the one from *Clostridium butyricum*.

Alternatively, (S)-lactate can be obtained from pyruvate via the deletion of at least one gene selected from the genes ldhA, dld and lldD combined with an overexpression of at least one lactate deshydrogenase such as the one from *Bacillus coagulans* (Niu et al, 2014).

In contrast, in order to obtain (R)-lactate from pyruvate, and hence favour the production of (R)-1,2-propanediol, the deletion of at least one gene selected from the genes ldhA, dld and lldD, preferably the dld gene, can be combined with an overexpression of at least one lactate deshydrogenase as defined above and an overexpression of at least one lactate racemase as defined above.

The production of 1,2-propanediol can be further improved by increasing NADPH availability in the microorganism. Strategies for increasing NADPH availability in the cell are well known in the art, and have notably been reviewed by Lee et al. (2013) and also described by U.S. Pat. No. 8,088,620, WO2012/055798 and EP14305691.9, herein incorporated by reference.

Thus, in a preferred embodiment, the microorganism of the invention comprises a further genetic modification of at least one gene involved in the production of NADPH as a source of reducing power.

Said genetic modification for improving the production of NADPH, and therefore its availability in the microorganism, is preferably selected from:
  overexpression of a gene or operon encoding a membrane-bound transhydrogenase,
  deletion or attenuation of a gene encoding a soluble transhydrogenase,
  overexpression of a gene encoding a NADPH generating glyceraldehyde 3-phosphate dehydrogenase,
  deletion or attenuation of a gene encoding a phosphoglucose isomerase,
  deletion or attenuation of a gene encoding a phosphofructokinase,
  overexpression of a gene encoding a glucose-6-phosphate dehydrogenase,
  overexpression of a mutant gene encoding a lipoamide dehydrogenase capable of generating NADPH,
  overexpression of a gene encoding a bi-functional NAD(P)H-hydrate repair enzyme, and
  any combination thereof.

The deletion or attenuation of a gene encoding a phosphofructokinase is more preferably combined with an overexpression of a gene encoding a glucose-6-phosphate dehydrogenase, in order to increase the flux of NADPH through the pentose phosphate pathway.

More preferably, the genetic modification for improving the production of NADPH is selected from:
  overexpression of a gene encoding a membrane-bound transhydrogenase,
  deletion or attenuation of a gene encoding a phosphoglucose isomerase and/or a soluble transhydrogenase, and
  overexpression of a gene encoding a NADPH generating glyceraldehyde 3-phosphate dehydrogenase.

Genes coding for the above described proteins are well-known in the art:
  genes or operons encoding a membrane-bound transhydrogenase include, without limitation the pntAB operon from *E. coli*, as notably described by WO2012/055798A1,
  genes encoding a soluble transhydrogenase include, without limitation, the udhA gene from *E. coli*, genes encoding a NADPH generating glyceraldehyde 3-phosphate dehydrogenase include, without limitation, the gapN from *Streptococcus mutans* (as described by Centeno-Leija et al., 2013) which can be used for example to substitute the endogenous gapA gene from *E. coli*, genes encoding a phosphoglucose isomerase include, without limitation the pgi gene from *E. coli*, genes encoding a phosphofructokinase include, without limitation, the pfkA gene from *E. coli* as notably described by WO2005/047498, genes encoding a glucose-6-phosphate dehydrogenase include, without limitation, the zwf gene from *E. coli* as notably described by Lim et al. (2002), mutant genes encoding a lipoamide dehydrogenase capable of generating NADPH include, without limitation, the mutant lpd gene (lpd*) from *E. coli* as notably described by Bocanegra et al. (1993), and genes encoding a bi-functional NAD(P)H-hydrate repair enzyme include, without limitation, the yjeF gene from *E. coli* as notably described by Marbaix et al. (2011).

In *E. coli*, should the pfkA gene be deleted or attenuated, such genetic modification is preferably combined with an overexpression of the zwf gene.

DRAWINGS

FIG. 1. Different pathways for the production of (R) or (S)-1,2-propanediol utilizing the intermediate Methylglyoxal or Lactate by a genetically modified microorganism for the production of 1,2-propanediol from different sources of carbon.

FIG. 2. Different pathways to produce (R) or (S)-1,2-propanediol by using the lactate as intermediate and an enzyme with a racemase activity to convert (R)-lactate into (S)-lactate and vice versa.

EXAMPLES

The present invention is further defined in the following examples. It should be understood that these examples, while indicating preferred embodiments of the invention, are given by way of illustration only. From above disclosure and these examples, the man skilled in the art can make various changes of the invention to adapt it to various uses and conditions without modifying the essentials means of the invention.

Exemplary genes and enzymes required for constructing microorganisms with these capabilities are described as well as methods for cloning and transformation, monitoring product formation and using the engineered microorganisms for production.

In particular, examples show modified *Escherichia coli* (*E. coli*) strains, but these modifications can easily be performed in other microorganisms of the same family or other microorganisms.

*Escherichia coli* belongs to the Enterobacteriaceae family, which comprises members that are Gram-negative, rod-shaped, non-spore forming and are typically 1-5 µm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organism, but other important members of the Enterobacteriaceae family include *Klebsiella*, in particular *Klebsiella terrigena*, *Klebsiella planticola* or *Klebsiella oxytoca*, *Pantoea* and *Salmonella*.

In the examples given below, methods well known in the art were used to construct *Escherichia coli* strains containing replicating vectors and/or various chromosomal deletions, and substitutions using homologous recombination well described by Datsenko & Wanner, (2000) for *E. coli*. In the same manner, the use of plasmids or vectors to express or overexpress one or several genes in a recombinant microorganisms are well known by the man skilled in the art. Examples of suitable *E. coli* expression vectors include pTrc, pACYC184n pBR322, pUC18, pUC19, pKC30, pRep4, pHS1, pHS2, pPLc236, etc. . . . (Studier et al., 1990 and Pouwels et al., 1985).

Several protocols have been used in the following examples. Protocol 1 (chromosomal modifications by homologous recombination, selection of recombinants), protocol 2 (transduction of phage P1) and protocol 3 (antibiotic cassette excision, the resistance genes were removed when necessary) used in this invention have been fully described in patent application EP 2532751, incorporated herein by reference. Chromosomal modifications were verified by a PCR analysis with appropriate oligonucleotides that the person skilled in the art is able to design.

Protocol 4: Construction of Recombinant Plasmids

Recombinant DNA technology is described in Molecular Cloning: Sambrook and Russell, (2001). Briefly, the DNA fragments were PCR amplified using oligonucleotides and appropriate genomic DNA as matrix (that the person skilled in the art will be able to define). The DNA fragments and chosen plasmid were digested with compatible restriction enzymes (that the person skilled in the art will be able to define), then ligated and transformed into competent cells. Transformants were analysed and recombinant plasmids of interest were verified by DNA sequencing.

Protocol 5: Flask Cultures for the Production of Recombinant Proteins

Flask cultures for the production of recombinant proteins were carried out as described in patent application WO 2010/076324 except that LB broth was supplemented with 5 g/L glucose.

Protocol 6: Evaluation of 1,2-Propanediol Production Strains 1,2-propanediol production strains were cultivated in flask cultures as described in patent application EP 2532751, except that 20 g/L glucose or sucrose and 40 g/L MOPS were used. 1,2-propanediol (MPG) was quantified by HPLC-RID with Biorad HPX-87H column. MPG enantiomeric form (S or R) was identified by GC-FID with Varian Chirasil-DEX column.

Example 1: Identification of New LAR Enzymes

Construction of Strain 1

To characterize the L-1,2-propanediol oxidoreductase from *Escherichia coli*, the gene fucO (SEQ ID No 2) was cloned into the expression plasmid pPAL7 (Biorad®). This plasmid was named pPG0249 and transformed into strain BL21(DE3)star, giving rise to strain 1.

Construction of Strain 2

To inactivate the aldehyde reductase encoded by the yqhD gene (SEQ ID No 8), the DyqhD::Km deletion described in patent application WO 2008/116853 was transferred by P1 phage transduction (according to Protocol 2) into strain BL21(DE3)star. To characterize the aldehyde reductase from *Escherichia coli*, the gene yqhD (SEQ ID No 8) was cloned into the expression plasmid pPAL7 (Biorad®). This plasmid was named pPG0332 and transformed into strain BL21(DE3)star DyqhD::Km, giving rise to strain 2.

Construction of Strain 3

To characterize the mutated yqhD*(G149E), site-directed mutagenesis on pPG0332 was used. This plasmid was named pPG0329 and transformed into strain BL21(DE3)star DyqhD::Km, giving rise to strain 3.

Construction of Strain 4

To inactivate the glyoxal reductase encoded by the yafB gene (SEQ ID No 10), the homologous recombination strategy was used (according to Protocols 1). Oligonucleotides for DyafB: SEQ ID No 29 and 30, were used to PCR amplify the resistance cassette. The strain retained was designated MG1655 DyafB::Km. Finally, the DyafB::Km deletion was transferred by P1 phage transduction (according to Protocol 2) into strain BL21(DE3)star. To characterize the glyoxal reductase from *Escherichia coli*, the gene yafB was cloned into the expression plasmid pPAL7 (Biorad®). This plasmid was named pPG0319 and transformed into strain BL21(DE3)star DyafB::Km, giving rise to strain 4.

Construction of Strain 5

To characterize the aldo-keto reductase from *Escherichia coli*, the gene yeaE (SEQ ID No 12) was cloned into the expression plasmid pPAL7 (Biorad®). This plasmid was named pPG0371 and transformed into strain BL21(DE3), giving rise to strain 5.

Construction of Strain 6

To characterize the predicted aldo/keto NAD(P) oxidoreductase from *Escherichia coli*, the gene ydhF (SEQ ID No 16) was cloned into the expression plasmid pPAL7 (Biorad®). This plasmid was named pPG0372 and transformed into strain BL21(DE3), giving rise to strain 6.

Construction of Strain 7

To characterize the predicted iron-containing alcohol dehydrogenase from *Escherichia coli*, the gene yiaY (SEQ ID No 4) was cloned into the expression plasmid pPAL7 (Biorad®). This plasmid was named pPG0270 and transformed into strain BL21(DE3), giving rise to strain 7.

Construction of Strain 8

To characterize the glycerol dehydrogenase from *Gluconobacter oxydans* (SEQ ID No 17), the synthetic gene gld optimized for *Escherichia coli* (SEQ ID No 31) was cloned into the expression plasmid pPAL7 (Biorad®). This plasmid was named pPG0381 and transformed into strain BL21(DE3), giving rise to strain 8.

Construction of Strain 9

To characterize the aldo keto reductase from *Bacillus subtilis*, the gene yhdN from *Bacillus subtilis* (SEQ ID No 20) was cloned into the expression plasmid pPAL7 (Biorad®). This plasmid was named pPG0357 and transformed into strain BL21(DE3), giving rise to strain 9.

Construction of Strain 10

To inactivate the gldA gene, the homologous recombination strategy was used (according to Protocols 1 and 3). Oligonucleotides for DgldA: SEQ ID No 32 and 33, were used to PCR amplify the resistance cassette. The strain retained was designated MG1655 DgldA::Km. Finally, the DgldA::Km deletion was transferred by P1 phage transduction (according to Protocol 2) into the strain BL21(DE3)star. To characterize the glycerol dehydrogenase from *Hypocrea jecorina* (SEQ ID No 21), the synthetic gene gld2 optimized for *Escherichia coli* (SEQ ID No 34) was cloned into the expression plasmid pPAL7 (Biorad®). This plasmid was named pPG0418 and transformed into strain BL21(DE3)star DgldA::Km previously described giving rise to strain 10.

Construction of Strain 11

To characterize the alcohol reductase from *Leishmania donovani* (SEQ ID No 23), the synthetic gene air optimized for *Escherichia coli* (SEQ ID No 35) was cloned into the expression plasmid pPAL7 (Biorad®). This plasmid was named pPG0259 and transformed into strain BL21(DE3), giving rise to strain 11.

Construction of Strain 12

To characterize the 1,2-propanediol:NAD+ oxidoreductase from *Escherichia coli*, the gene gldA (SEQ ID No 6) was cloned into the expression plasmid pET101/D-TOPO (Lifetechnologies®). This plasmid was named pPG0029 and transformed into strain BL21(DE3)star, giving rise to the strain 12.

Construction of Strain 13

To characterize the beta-keto ester reductase from *Escherichia coli*, the gene yqhE (SEQ ID No 14) was cloned into the expression plasmid pET TOPO (Lifetechnologies®). This plasmid was named pPG0153 and transformed into strain BL21(DE3)star, giving rise to the strain 13.

Construction of strains 14 to 33

To characterize the mutated aldehyde reductase from *Escherichia coli*, first the native gene yqhD (SEQ ID No 8) was cloned into the plasmid pTRC99A (Amersham Pharmacia®), this plasmid was named pME0103. Site-directed mutagenesis was used on pME0103 to introduce diverse mutations:

yqhD*(V151L); yqhD*(G149E); yqhD*(T142S); yqhD*(T142G); yqhD*(S144A); yqhD*(G149A); yqhD*(G149H); yqhD*(G149K); yqhD*(G149M); yqhD*(G149T); yqhD*(G149N); yqhD*(G149R); yqhD*(G149S); yqhD*(G149V); yqhD*(A1621); yqhD*(A162K); yqhD*(A162D); yqhD*(A162L); yqhD*(A162N); yqhD*(V151M).

The plasmids obtained were transformed into strain BL21 (DE3), giving rise to strains 14 to 33.

Preparation of Cell-Free Extract

The cells (400-600 mg dry weight) were resuspended in extraction buffer (60-100 ml). The suspended cells were disrupted by 8 sonication cycles of 30 sec on ice (Branson sonifier, 70 W). Cells were incubated for 45 minutes at room temperature with 1-5 mM MgCl2 and 2 Ul/ml of DNaseI. Cells debris were removed by centrifugation at 12000 g for 30 min at 4° C. The supernatant was kept as the crude extract.

For FucO, the extraction was also realized in anaerobia.

TABLE 3

Buffers used for preparation of cell-free extract

| Enzyme | Extraction buffer |
|---|---|
| FucO | 10 mM Tris-HCl pH 7.5 |
| | 2.5 mM NAD+ and protease inhibitor |
| YqhD wild-type and mutants | 100 mM Potassium phosphate pH 7.6 and protease inhibitor |
| YafB | 1M Tris-HCl pH 7 and protease inhibitor |
| YeaE | 100 mM Potassium phosphate pH 7.6 and protease inhibitor |
| YdhF | 100 mM Potassium phosphate pH 7.6 and protease inhibitor |
| YiaY | 100 mM Potassium phosphate pH 7.6 and protease inhibitor |
| GOX1615 | 100 mM Potassium phosphate pH 7.6 and protease inhibitor |
| YhdN | 100 mM Potassium phosphate pH 7.6 and protease inhibitor |
| Gld2 | 5 mM Sodium phosphate pH 7 and protease inhibitor |
| Alr | 100 mM Potassium phosphate pH 7.6 and protease inhibitor |

TABLE 3-continued

Buffers used for preparation of cell-free extract

| Enzyme | Extraction buffer |
|---|---|
| GldA | 100 mM Potassium phosphate pH 7.6 + 20 mM Imidazole and protease inhibitor |
| YqhE | 20 mM Tris-HCl pH 8.3 and protease inhibitor |

Purification

Subtilisine Affinity Purification

The enzymes were purified from the crude extract by using subtilisine affinity chromatography (Profinity 5 ml, BIORAD) according to the manufacturer's instructions. The crude extract was loaded on the column equilibrated with wash buffer. The Tag was removed from the protein by fluoride cleavage (incubation on the column with 100 mM fluoride at room temperature for 30 minutes). The protein was eluted with the elution buffer. The fractions which contain the protein were pooled, concentrated and loaded on a gel filtration column (Superdex 200 10/300 GL column, GE Healthcare) equilibrated with analysis buffer except for YafB, YeaE, YhdN and Gld2, the buffer was exchanged against analysis buffer by dialysis over night. Protein concentration was determined using Bradford assay.

For FucO, the purification was also realized in anaerobia condition.

Native Purification (YqhE)

The purification of YqhE was realized in 2 steps.

Step 1: Ion Exchange Chromatography

Using an Akta Purifier (GE Healthcare), the crude extract was loaded onto a 5 ml HiTrapQ FF column (GE Healthcare) equilibrated with the wash buffer. Proteins were eluted with a gradient of 20 column volumes from 0% to 100% of elution buffer. The fractions which contain the protein were pooled and the buffer was exchanged against analysis buffer by dialysis for 2 hours.

Step 2: Affinity Chromatography

Using an Akta Purifier (GE Healthcare), the protein from the first step was loaded onto a 1 ml HiTrapBlueHP1 column (GE Healthcare) equilibrated with the wash buffer. Proteins were eluted with a gradient of 20 column volumes from 0% to 100% of NaCl elution buffer. The fractions which contain the protein were pooled, concentrated and loaded on a gel filtration column (Superdex 200 10/300 GL column, GE Healthcare) equilibrated with analysis buffer. The fractions which contain the protein were pooled and concentrated. Protein concentrations were determined using Bradford assay.

TABLE 4

Buffers used for subtilisine affinity purification

| Enzyme | Wash buffer | Elution buffer | Analysis buffer |
|---|---|---|---|
| FucO | 50 mM Tris-HCl pH 7.5 | 50 mM Tris-HCl pH 7.5 100 mM Sodium fluoride | 50 mM Tris-HCl pH 7.5 |
| YqhD and YqhD*(G14 9E) | 100 mM Potassium Phosphate pH 7.6 | 100 mM Potassium Phosphate, 100 mM Sodium Fluoride pH 7.6 | 50 mM Hepes pH 7.5 |
| YafB | 1M Tris-HCl pH 7 | 1M Tris-HCl pH 7 100 mM Sodium Fluoride | 1M Tris-HCl pH 7 150 mM NaCl |
| YeaE | 100 mM Potassium Phosphate pH 7.6 | 100 mM Potassium Phosphate, 100 mM Sodium Fluoride pH 7.6 | 50 mM Hepes pH 7.5 |
| YdhF | 100 mM Potassium Phosphate pH 7.6 | 100 mM Potassium Phosphate, 100 mM Sodium Fluoride pH 7.6 | 50 mM Hepes pH 7.5 |
| YiaY | 100 mM Potassium Phosphate pH 7.6 | 100 mM Potassium Phosphate, 100 mM Sodium Fluoride pH 7.6 | 50 mM Potassium Phosphate 150 mM NaCl pH 7.6 |
| GOX1615 | 100 mM Potassium Phosphate pH 7.6 | 100 mM Potassium Phosphate, 100 mM Sodium Fluoride pH 7.6 | 50 mM HEPES pH 7.5 |
| YhdN | 100 mM Potassium Phosphate pH 7.6 | 100 mM Potassium Phosphate, 100 mM Sodium Fluoride pH 7.6 | 100 mM Potassium Phosphate pH 7.6 |
| Gld2 | 5 mM Sodium Phosphate pH 7 | 5 mM Sodium Phosphate 100 mM Sodium Fluoride pH 7 | 100 mM MES pH 6.5 |
| Alr | 100 mM Potassium Phosphate pH 7.6 | 100 mM Potassium Phosphate, 100 mM Sodium Fluoride pH 7.6 | 100 mM Potassium Phosphate pH 7.6 |

Nickel Affinity Purification (GldA)

The enzyme was purified from the crude extract by using Nickel affinity chromatography (HisTrapFF 1 mL, GE Healthcare) according to the manufacturer's instructions. The enzyme was eluted by using a linear gradient of imidazole (20 to 500 mM) in 100 mM potassium phosphate (pH 7.6). The fractions containing the protein were pooled, concentrated and the buffer was exchanged against 100 mM MES (pH6.5) by dialysis over night. Protein concentration was determined using Bradford assay.

TABLE 5

Buffers used for affinity chromatography

| Step | Column | Wash buffer | Elution buffer | Analysis buffer |
|---|---|---|---|---|
| 1 | HiTrapQ | 20 mM Tris-HCl pH 8.3 | 20 mM Tris-HCl pH 8.3 1M NaCl | 20 mM Tris-HCl pH 7 |

TABLE 5-continued

Buffers used for affinity chromatography

| Step | Column | Wash buffer | Elution buffer | Analysis buffer |
|---|---|---|---|---|
| 2 | HiTrapBlue | 20 mM Tris-HCl pH 7 | 20 mM Tris-HCl pH 7 1M NaCl | 20 mM Tris-HCl 150 mM NaCl |

Demonstration of the NAD(P)H Dependent Lactaldehyde Reductase Activity of Purified Proteins NAD(P)H dependent lactaldehyde reductase assay (R-LAR with R-lactaldehyde or S-LAR with S-lactaldehyde)

The R-LAR and S-LAR activity was determined by measuring the consumption of NAD(P)H at 340 nm on a spectrophotometer ($\epsilon_{340}$=6290 M$^{-1}$ cm$^{-1}$) and at 30° C. The reaction mixture (1 mL) containing assay buffer, 0.2 mM to 0.4 mM NAD(P)H and protein was incubated for 5 min at 30° C. Then, 5-10 mM of lactaldehyde was added to start the reaction. One unit of enzyme activity was defined as the amount of enzyme catalyzing the decrease of 1 µmol of NAD(P)H per min. Specific enzyme activity was expressed as units of enzyme activity per mg of protein. The activity value determined without substrate in the assay was subtracted.

For FucO, the assay was also realized in anaerobia condition.

The results are presented in Table 6 and 7

TABLE 6

Activity of purified enzymes

| Enzyme | Assay buffer | Cofactor | R-LAR (mUI/mg) | S-LAR (mUI/mg) |
|---|---|---|---|---|
| FucO anaerobia | 100 mM MES-KOH (pH 6.5) 0.1 mM FeSO4 30 mM ammonium sulfate | NADH | 1835 | 19362 |
| FucO | 100 mM MES-KOH (pH 6.5) 0.1 mM FeSO4 30 mM ammonium sulfate | NADH | 593 | 4313 |
| YiaY | 20 mM Hepes (pH 7.5) 0.1 mM FeSO4 | NADH | 4175 | 4199 |
| GldA | 100 mM MES-KOH (pH 6.5) 0.1 mM FeSO4 30 mM ammonium sulfate | NADH | 46891 | 13827 |
| YqhD | 20 mM Hepes (pH 7.5) 0.1 mM ZnSO4 | NADPH | 234 | 627 |
| YqhD* (G149E) | 20 mM Hepes (pH 7.5) 0.1 mM ZnSO4 | NADPH | 238 | 1654 |
| YafB | 20 mM Hepes (pH 7.5) | NADPH | 6698 | 2959 |
| YeaE | 20 mM Hepes (pH 7.5) | NADPH | 241 | 206 |
| YqhE | 20 mM Hepes (pH 7.5) 0.1 mM ZnSO4 | NADPH | 6768 | 4527 |
| YdhF | 20 mM Hepes (pH 7.5) | NADPH | 537 | 196 |
| GOX1615 | 20 mM Hepes (pH 7.5) | NADPH | 23594 | 1555 |
| YhdN | 20 mM Hepes (pH 7.5) 0.1 mM ZnSO4 | NADPH | 6880 | 5751 |
| Gld2 | 10 mM sodium phosphate (pH 7) | NADPH | 4875 | 2638 |
| Alr | 20 mM Hepes (pH 7.5) | NADPH | 1512 | 1453 |

TABLE 7

Activity of cell extracts

| Enzyme | Assay buffer | cofactor | R-LAR (mUI/mg) | S-LAR (mUI/mg) |
|---|---|---|---|---|
| YqhD* (G149E) | 20 mM Hepes (pH 7.5) 0.1 mM ZnSO4 | NADPH | 42 | 301 |
| YqhD* (T142S) | 20 mM Hepes (pH 7.5) 0.1 mM ZnSO4 | NADPH | 52 | 117 |
| YqhD* (T142G) | 20 mM Hepes (pH 7.5) 0.1 mM ZnSO4 | NADPH | 35 | 315 |
| YqhD* (S144A) | 20 mM Hepes (pH 7.5) 0.1 mM ZnSO4 | NADPH | 22 | 356 |
| YqhD* (G149A) | 20 mM Hepes (pH 7.5) 0.1 mM ZnSO4 | NADPH | 53 | 356 |
| YqhD* (G149H) | 20 mM Hepes (pH 7.5) 0.1 mM ZnSO4 | NADPH | 57 | 151 |
| YqhD* (G149K) | 20 mM Hepes (pH 7.5) 0.1 mM ZnSO4 | NADPH | 84 | 222 |
| YqhD* (G149M) | 20 mM Hepes (pH 7.5) 0.1 mM ZnSO4 | NADPH | 45 | 124 |
| YqhD* (G149T) | 20 mM Hepes (pH 7.5) 0.1 mM ZnSO4 | NADPH | 79 | 265 |
| YqhD* (G149N) | 20 mM Hepes (pH 7.5) 0.1 mM ZnSO4 | NADPH | 58 | 245 |
| YqhD* (G149R) | 20 mM Hepes (pH 7.5) 0.1 mM ZnSO4 | NADPH | 57 | 208 |
| YqhD* (G149S) | 20 mM Hepes (pH 7.5) 0.1 mM ZnSO4 | NADPH | 62 | 208 |
| YqhD* (G149V) | 20 mM Hepes (pH 7.5) 0.1 mM ZnSO4 | NADPH | 47 | 148 |
| YqhD* (A162I) | 20 mM Hepes (pH 7.5) 0.1 mM ZnSO4 | NADPH | 45 | 120 |
| YqhD* (A162K) | 20 mM Hepes (pH 7.5) 0.1 mM ZnSO4 | NADPH | 54 | 338 |
| YqhD* (A162D) | 20 mM Hepes (pH 7.5) 0.1 mM ZnSO4 | NADPH | 20 | 337 |
| YqhD* (A162L) | 20 mM Hepes (pH 7.5) 0.1 mM ZnSO4 | NADPH | 62 | 176 |
| YqhD* (A162N) | 20 mM Hepes (pH 7.5) 0.1 mM ZnSO4 | NADPH | 35 | 320 |
| YqhD* (V151L) | 20 mM Hepes (pH 7.5) 0.1 mM ZnSO4 | NADPH | 20 | 724 |
| YqhD* (V151M) | 20 mM Hepes (pH 7.5) 0.1 mM ZnSO4 | NADPH | 19 | 360 |

Example II: Production of 1,2-Propanediol with New LAR Enzymes

Construction of Strain 34

*Escherichia coli* strain MG1655 is modified to produce lactate. To inactivate the acetate kinase and phosphotransacetylase encoded by the ackA and pta genes respectively, the pyruvate oxydase encoded by the poxB gene, the alcohol dehydrogenase encoded by the adhE gene, the pyruvate formate lyase activating enzyme and the pyruvate formate lyase encoded by the pflA and pflB genes respectively, the aldehyde dehydrogenases encoded by the aldA and aldB genes, the DackA-pta, DpoxB, DadhE, DpflAB, DaldA and DaldB deletions described in patent application WO 2008/116852 are transferred by P1 phage (according to Protocol 2) into strain MG1655 and the resistance genes are removed according to protocol 3. To inactivate the lactate dehydrogenase encoded by the dld gene and the methylglyoxal synthase encoded by the gene mgsA, Ddld and DmgsA deletions described in patent application WO 2011/012693 are transferred by P1 phage (according to Protocol 2) into the previous strain and the resistance genes are removed according to protocol 3 giving rise to strain MG1655 DackA-pta DpoxB DadhE DpflAB DaldA DaldB Ddld DmgsA. To inactivate the fumarate reductase flavoprotein complex encoded by the frdABCD operon and the phosphoenol pyruvate synthase encoded by the ppsA gene, the homologous recombination strategy is used (according to Protocols 1). Oligonucleotides for DfrdABCD: SEQ ID No 36 and 37, and DppsA: SEQ ID No 38 and 39, are used to PCR amplify the resistance cassettes. The strains retained are designated MG1655 DfrdABCD::Cm and MG1655 DppsA::Km. Finally, the DfrdABCD::Cm and the DppsA::Km deletions are transferred by P1 phage transduction (according to Protocol 2) into the previous strain and the resistance genes are removed according to protocol 3 giving rise to strain 34.

Construction of Strains 35 to 66

First, to overproduce 1,2-propanediol, all the lactaldehyde reductase candidates (from *E. coli*: fucO, yafB, yeaE, ydhF, yiaY, gldA, yqhE, wild-type and mutated yqhD; from *Gluconobacter oxydans*: GOX1615; from *Bacillus subtilis*: yhdN; from *Hypocrea jecorina*: gld2; from *Leishmania donovani*: alr) are each cloned into the pME101VB06 plasmid described in patent application EP 2532751 giving rise to 33 pME101VB06-lactaldehyde reductase plasmids. Then, to overproduce racemic (R)-1,2-propanediol, the lactoyl-coA transferase from *Megasphaera elsdenii* encoded by the pct gene, and the lactoyl-coA reductase from *Salmonella enterica*, encoded by the pduP gene are heterologously expressed on plasmid. The synthetic gene pct optimized for *Escherichia coli* (SEQ ID No 40) and the pduP gene (SEQ ID No 41) are heterologously and separately expressed under a Ptrc artificial promoter and an artificial ribosome binding site (sequence given in patent WO 2007/0770441) on a pBBR1MCS5 plasmid (Kovach et al., 1995) giving rise to plasmid pBBR1MCS5-Ptrc01/RBS01-pctmeO1ec-Ptrc01/RBS01-pduPse. Finally each pME101VB06-lactaldehyde reductase plasmid and the pBBR1MCS5-Ptrc01/RBS01-pctmeO1ec-Ptrc01/RBS01-pduPse plasmid are transformed into strain 34 giving rise to strains 35 to 66.

Construction of Strains 67 to 98

To overproduce racemic (S)-1,2-propanediol, the lactate racemase from *Lactobacillus sakei* encoded by the larA gene (SEQ ID No 26) is heterologously and separately expressed under a Ptrc artificial promoter and an artificial ribosome binding site on the pBBR1MCS5-Ptrc01/RBS01-pctmeO1ec-Ptrc01/RBS01-pduPse plasmid giving rise to plasmid pBBR1MCS5-Ptrc01/RBS01-pctmeO1ec-Ptrc01/RBS01-pduPse-Ptrc01/RBS01-larAls. Finally each pME101VB06-lactaldehyde reductase plasmid and the pBBR1MCS5-Ptrc01/RBS01-pctmeO1ec-Ptrc01/RBS01-pduPse-Ptrc01/RBS01-larAls plasmid are transformed into the strain 34 giving rise to strains 67 to 98.

Construction of Strains 99 to 131

To overproduce (S)-lactate and (S)-1,2-propanediol, the lactate dehydrogenase encoded by the ldhA gene is deleted as described in patent application WO 2008/116852 and transferred by P1 phage (according to Protocol 2) into strain 34 giving rise to strain 99. Then the L-lactate dehydrogenase from *Bacillus coagulans* encoded by the ldh gene (SEQ ID No 42) is heterologously and separately expressed under a Ptrc artificial promoter and an artificial ribosome binding site on the pBBR1MCS5-Ptrc01/RBS01-pctmeO1ec-Ptrc01/RBS01-pduPse plasmid giving rise to plasmid pBBR1MCS5-Ptrc01/RBS01-pctmeO1ec-Ptrc01/RBS01-pduPse-Ptrc01/RBS01-ldhbc. Finally each pME101VB06-lactaldehyde reductase plasmid and the pBBR1MCS5-Ptrc01/RBS01-pctmeO1ec-Ptrc01/RBS01-pduPse-Ptrc01/RBS01-ldhbc plasmid are transformed into strain 99 giving rise to strains 100 to 131.

Construction of Strains 132 to 163

To overproduce (R)-lactate and (R)-1,2-propanediol, the lactate racemase from *Lactobacillus plantarum* encoded by the larA gene (SEQ ID No 28) is heterologously and separately expressed under a Ptrc artificial promoter and an artificial ribosome binding site on the pBBR1MCS5-Ptrc01/RBS01-pctmeO1ec-Ptrc01/RBS01-pduPse-Ptrc01/RBS01-ldhbc plasmid giving rise to plasmid pBBR1MCS5-Ptrc01/RBS01-pctmeO1ec-Ptrc01/RBS01-pduPse-Ptrc01/RBS01-ldhbc-Ptrc01/RBS01-larAlp. Finally each pME101VB06-lactaldehyde reductase plasmid and the pBBR1MCS5-Ptrc01/RBS01-pctmeO1ec-Ptrc01/RBS01-pduPse-Ptrc01/RBS01-ldhbc-Ptrc01/RBS01-larAlp plasmid are transformed into strain 99 giving rise to strains 132 to 163.

Construction of strains 164 to 196 To re-introduce the gloA gene, the homologous recombination strategy is used (according to Protocols 1 and 3). Oligonucleotides for gloA reconstruction: SEQ ID No 43 and 4, are used to PCR amplify the resistance cassette. The strain retained is designated MG1655 gloArc::Km and the gloArc::Km modification is transferred by P1 phage transduction (according to Protocol 2) into the evolved strain MG1655 lpd* DtpiA DpflAB DadhE DldhA DgloA DaldA DaldB Dedd DarcA Dndh described in patent application WO2008/116852. Then, to inactivate the lactate dehydrogenase from *Escherichia coli* encoded by the dld gene, Ddld::Cm deletion described in patent application WO 2011/012693 is transferred by P1 phage (according to Protocol 2) into the previous strain giving rise to strain 164. Finally, each pME101VB06-lactaldehyde reductase plasmid and the pBBR1MCS5-Ptrc01/RBS01-pctmeO1ec-Ptrc01/RBS01-pduPse plasmid are transformed into strain 164 giving rise to strains 165 to 196.

Construction of Strains 202 to 212

To inactivate the gldA and yqhD genes, the homologous recombination strategy is used as described for construction of strain 10 and strain 2 respectively (according to Protocols 1 and 3) the DgldA::Km and DyqhD::Km are transferred by P1 phage transduction (according to Protocol 2) into strain 164 giving rise to strain 197. Finally each pME101VB06-lactaldehyde reductase plasmid, except yqhD (wild-type and mutated) and gldA plasmids, and the pBBR1MCS5-Ptrc01/RBS01-pctmeO1ec-Ptrc01/RBS01-pduPse-Ptrc01/RBS01-larAls plasmid are transformed into strain 197 giving rise to strains 198 to 207.

Production of 1,2-Propanediol in Shake Flasks 1,2-propanediol (MPG) producing strains were cultivated and MPG was quantified as described in protocol 6.

Compared to strain 35, considered as the control strain and described in patent WO 2012/172050, all strains produced more MPG.

TABLE 8

1,2-propanediol produced by strains of the present invention

| Strain | LAR enzyme | MPG produced | Enantiomeric form of MPG |
|---|---|---|---|
| 35 | FucO | Control (WO 2012/172050) | R |
| 36 | YafB | ++ | R |
| 37 | YeaE | + | R |
| 38 | YdhF | + | R |
| 39 | YiaY | ++ | R |
| 40 | GldA | ++ | R |
| 41 | YqhE | ++ | R |
| 42 | YqhD | + | R |
| 43 | GOX1615 | ++ | R |
| 44 | YhdN | ++ | R |

TABLE 8-continued 1,2-propanediol produced by strains of the present invention

| Strain | LAR enzyme | MPG produced | Enantiomeric form of MPG |
|---|---|---|---|
| 45 | Gld2 | ++ | R |
| 46 | Alr | ++ | R |
| 47 | YqhD*(G149E) | ++ | R |
| 48 | YqhD*(T142S) | ++ | R |
| 49 | YqhD*(T142G) | ++ | R |
| 50 | YqhD*(S144A) | ++ | R |
| 51 | YqhD*(G149A) | ++ | R |
| 52 | YqhD*(G149H) | ++ | R |
| 53 | YqhD*(G149K) | ++ | R |
| 54 | YqhD*(G149M) | + | R |
| 55 | YqhD*(G149T) | ++ | R |
| 56 | YqhD*(G149N) | ++ | R |
| 57 | YqhD*(G149R) | ++ | R |
| 58 | YqhD*(G149S) | ++ | R |
| 59 | YqhD*(G149V) | + | R |
| 60 | YqhD*(A162I) | + | R |
| 61 | YqhD*(A162K) | ++ | R |
| 62 | YqhD*(A162D) | ++ | R |
| 63 | YqhD*(A162L) | ++ | R |
| 64 | YqhD*(A162N) | ++ | R |
| 65 | YqhD*(V151L) | ++ | R |
| 66 | YqhD*(V151M) | ++ | R |
| 67 | FucO | ++ | S |
| 68 | YafB | ++ | S |
| 69 | YeaE | + | S |
| 70 | YdhF | + | S |
| 71 | YiaY | + | S |
| 72 | GldA | ++ | S |
| 73 | YqhE | ++ | S |
| 74 | YqhD | + | S |
| 75 | GOX1615 | + | S |
| 76 | YhdN | ++ | S |
| 77 | Gld2 | ++ | S |
| 78 | Alr | + | S |
| 79 | YqhD*(G149E) | ++ | S |
| 80 | YqhD*(T142S) | ++ | S |
| 81 | YqhD*(T142G) | ++ | S |
| 82 | YqhD*(S144A) | ++ | S |
| 83 | YqhD*(G149A) | ++ | S |
| 84 | YqhD*(G149H) | ++ | S |
| 85 | YqhD*(G149K) | ++ | S |
| 86 | YqhD*(G149M) | + | S |
| 87 | YqhD*(G149T) | ++ | S |
| 88 | YqhD*(G149N) | ++ | S |
| 89 | YqhD*(G149R) | ++ | S |
| 90 | YqhD*(G149S) | ++ | S |
| 91 | YqhD*(G149V) | + | S |
| 92 | YqhD*(A162I) | + | S |
| 93 | YqhD*(A162K) | ++ | S |
| 94 | YqhD*(A162D) | ++ | S |
| 95 | YqhD*(A162L) | ++ | S |
| 96 | YqhD*(A162N) | ++ | S |
| 97 | YqhD*(V151L) | ++ | S |
| 98 | YqhD*(V151M) | ++ | S |
| 100 | FucO | ++ | S |
| 101 | YafB | ++ | S |
| 102 | YeaE | + | S |
| 103 | YdhF | + | S |
| 104 | YiaY | + | S |
| 105 | GldA | ++ | S |
| 106 | YqhE | ++ | S |
| 107 | YqhD | + | S |
| 108 | GOX1615 | + | S |
| 109 | YhdN | ++ | S |
| 110 | Gld2 | ++ | S |
| 111 | Alr | + | S |
| 112 | YqhD*(G149E) | ++ | S |
| 113 | YqhD*(T142S) | ++ | S |
| 114 | YqhD*(T142G) | ++ | S |
| 115 | YqhD*(S144A) | ++ | S |
| 116 | YqhD*(G149A) | ++ | S |
| 117 | YqhD*(G149H) | ++ | S |
| 118 | YqhD*(G149K) | ++ | S |
| 119 | YqhD*(G149M) | + | S |
| 120 | YqhD*(G149T) | ++ | S |
| 121 | YqhD*(G149N) | ++ | S |
| 122 | YqhD*(G149R) | ++ | S |
| 123 | YqhD*(G149S) | ++ | S |
| 124 | YqhD*(G149V) | + | S |
| 125 | YqhD*(A162I) | + | S |
| 126 | YqhD*(A162K) | ++ | S |
| 127 | YqhD*(A162D) | ++ | S |
| 128 | YqhD*(A162L) | ++ | S |
| 129 | YqhD*(A162N) | ++ | S |
| 130 | YqhD*(V151L) | ++ | S |
| 131 | YqhD*(V151M) | ++ | S |
| 132 | FucO | + | R |
| 133 | YafB | ++ | R |
| 134 | YeaE | + | R |
| 135 | YdhF | + | R |
| 136 | YiaY | ++ | R |
| 137 | GldA | ++ | R |
| 138 | YqhE | ++ | R |
| 139 | YqhD | + | R |
| 140 | GOX1615 | ++ | R |
| 141 | YhdN | ++ | R |
| 142 | Gld2 | + | R |
| 143 | Alr | + | R |
| 144 | YqhD*(G149E) | ++ | R |
| 145 | YqhD*(T142S) | ++ | R |
| 146 | YqhD*(T142G) | ++ | R |
| 147 | YqhD*(S144A) | ++ | R |
| 148 | YqhD*(G149A) | ++ | R |
| 149 | YqhD*(G149H) | ++ | R |
| 150 | YqhD*(G149K) | ++ | R |
| 151 | YqhD*(G149M) | + | R |
| 152 | YqhD*(G149T) | ++ | R |
| 153 | YqhD*(G149N) | ++ | R |
| 154 | YqhD*(G149R) | ++ | R |
| 155 | YqhD*(G149S) | ++ | R |
| 156 | YqhD*(G149V) | + | R |
| 157 | YqhD*(A162I) | + | R |
| 158 | YqhD*(A162K) | ++ | R |
| 159 | YqhD*(A162D) | ++ | R |
| 160 | YqhD*(A162L) | ++ | R |
| 161 | YqhD*(A162N) | ++ | R |
| 162 | YqhD*(V151L) | ++ | R |
| 163 | YqhD*(V151M) | ++ | R |
| 165 | FucO | + | R/S |
| 166 | YafB | ++ | R/S |
| 167 | YeaE | + | R/S |
| 168 | YdhF | + | R/S |
| 169 | YiaY | ++ | R/S |
| 170 | GldA | ++ | R/S |
| 171 | YqhE | ++ | R/S |
| 172 | YqhD | + | R/S |
| 173 | GOX1615 | ++ | R/S |
| 174 | YhdN | ++ | R/S |
| 175 | Gld2 | + | R/S |
| 176 | Alr | + | R/S |
| 177 | YqhD*(G149E) | ++ | R/S |
| 178 | YqhD*(T142S) | ++ | R/S |
| 179 | YqhD*(T142G) | ++ | R/S |
| 180 | YqhD*(S144A) | ++ | R/S |
| 181 | YqhD*(G149A) | ++ | R/S |
| 182 | YqhD*(G149H) | ++ | R/S |
| 183 | YqhD*(G149K) | ++ | R/S |
| 184 | YqhD*(G149M) | + | R/S |
| 185 | YqhD*(G149T) | ++ | R/S |
| 186 | YqhD*(G149N) | ++ | R/S |
| 187 | YqhD*(G149R) | ++ | R/S |
| 188 | YqhD*(G149S) | ++ | R/S |
| 189 | YqhD*(G149V) | + | R/S |
| 190 | YqhD*(A162I) | + | R/S |
| 191 | YqhD*(A162K) | ++ | R/S |
| 192 | YqhD*(A162D) | ++ | R/S |
| 193 | YqhD*(A162L) | ++ | R/S |
| 194 | YqhD*(A162N) | ++ | R/S |
| 195 | YqhD*(V151L) | ++ | R/S |
| 196 | YqhD*(V151M) | ++ | R/S |

TABLE 8-continued 1,2-propanediol produced by strains of the present invention

| Strain | LAR enzyme | MPG produced | Enantiomeric form of MPG |
|---|---|---|---|
| 198 | FucO | + | R |
| 199 | YafB | ++ | R |
| 200 | YeaE | + | R |
| 201 | YdhF | + | R |
| 202 | YiaY | ++ | R |
| 203 | YqhE | ++ | R |
| 204 | GOX1615 | ++ | R |
| 205 | YhdN | ++ | R |
| 206 | Gld2 | + | R |
| 207 | Alr | + | R |

(the symbol + indicates an increase of more than 10% compared to the control strain, and the symbol ++ indicates an increase of more than 50% compared to the control strain)

REFERENCES

Altaras N E and Cameron D C (2000), Biotechnol. Prog., 16: 940-946

Altaras N E and Cameron D C (1999), Appl. Environ. Microbiol., 65: 1180-1185

Altschul S, Gish W, Miller W, Myers E, Lipman D J (1990), J. Mol. Biol. 215 (3): 403-410

Badia J, Ros J, Aguilar J (1985), *J. Bacteriol.* 161: 435-437

Bennett G N and San K Y (2001), Appl. Microbiol. Biotechnol. 55: 1-9

Berrios-Rivera S J, San K Y, Bennett G N (2003), J. Ind. Microbiol. Biotechnol., 30: 34-40

Blikstad C, Widersten M (2010), J Mol Catal B-Enzym., 66:148-155

Bocanegra J, Scrutton N, Perham R (1993) Biochemistry, 32 (11): 2737-2740

Boronat A, Aguilar J (1979) J Bacteriol 140: 320-326

Bradford M M (1976) Anal Biochem., 72: 248-254.

Cabiscol E, Badia J, Baldoma L, Hidalgo E, Aguilar J, Ros J (1992). Biochim Biophys Acta 1118 (2): 155-60.

Cameron D C, Altaras N E, Hoffman M L, Shaw A J (1998), Biotechnol. Prog., 14: 116-125

Cantwell A, Dennis D (1974), Biochemistry, 13(2):287-291

Carrier T & Keasling J (1999), Biotechnol Prog., 15 (1): 58-64

Centeno-Leija S, Utrilla J, Flores N, Rodriguez A, Gosset G, Martinez A (2013) Antonie Van Leeuwenhoek., 104 (6), 913-924.

Cooper R A (1984), Annu. Rev. Microbiol. 38: 49-68

Davis J J & Olsen G J., 2001, Mol. Biol. Evol., 28(1):211-221.

Deml L, Bojak A, Steck S, Graf M, Wild J, Schirmbeck R, Wolf H, Wagner R., 2011, J. Virol., 75(22): 10991-11001.

Desguin B, Goffin P, Bakouche N, Diman A, Viaene E, Dandoy D, Fontaine L, Hallet B, Hols P (2014), J. Bacteriol. doi:10.1128/JB.02192-14

Desguin B, Goffin P, Viaene E, Kleerebezem M, Martin-Diaconescu V, Maroney M J, Declercq J P, Soumillion P, Hols P (2014), Nature Comm. DOI: 10.1038/ncomms4615

Graf M, Bojak A, Deml L, Bieler K, Wolf H, Wagner R., 2000, J. Virol., 74(22): 10/22-10826.

Goffin P, Deghorain M, Mainardi J L, Tytgat I, Champomier-Verges M C, Kleerebezem M, Hols P (2005), J. Bacteriol. 187(19):6750-6761

Hino T, Kuroda S (1993), Appl. Environ. Microbiol. 59(1): 255-259

Hiyama T, Fukui S, Kitahara K (1968), J Biochem. 64(1): 99-107

Huang K, Rudolph F B, Bennett G N (1999), Appl. Environ. Microbiol., 65: 3244-3247

Kovach M E, Elzer P H, Hill D S, Robertson G T, Farris M A, Roop R M, Peterson K M (1995) Gene, 166(1):175-176

Lee S, McCormick M, Lippard S, Cho U (2013), Nature, 494: 380-384

Lim S, Jung Y, Shin H, Lee Y (2002), J Biosci Bioeng., 93 (6):543-549

Marbaix A, Noel G, Detroux A, Vertommen D, Schaftingen E, Linster C (2011), J Biol Chem., 286 (48), 41246-41252

Misra K, Banerjee A R, Ray S, Ray M (1995), Biochem. J. 305: 999-1003

Needleman S B and Wunsch C D, 1970, Journal of Molecular Biology, 48(3):443-453

Niu W, Guo J (2014), ACS Synth Biol., DOI: 10.1021/sb500240p

Pepple J S, Dennis D (1976), Biochim Biophys Acta. 429(3):1036-1040

Pouwels P. H. et al., Eds. (1985) Cloning Vectors. Elsevier: New York

Salis H (2011), Methods Enzymol., 498:19-42

Sambrook and Russell, (2001), Molecular Cloning: 3$^{rd}$ edition, Cold Spring Harbor Laboratory Press, N Y, Vol 1, 2, 3

Segel I (1993), Enzyme kinetics, John Wiley & Sons, pp. 44-54 and 100-112

Studier et al., *Gene Expression Technology: Methods in Enzymology* 185, Academic Press, San Diego, Calif. (1990) 60-89)

Sulzenbacher G, Alvarez K, Van den Heuvel R H H, Versluis C, Spinelli S, Campanacci V, Valencia C, Cambillau C, Eklund H, Tegoni M (2004), J. Mol. Biol. 342: 489-502

The invention claimed is:

1. A method for producing 1, 2-propanediol, comprising the steps of:
   a) culturing a recombinant microorganism in a culture medium comprising a carbon source, wherein said microorganism is genetically modified to comprise at least one pathway for the production of (R), (S) and/or (R,S) lactaldehyde and wherein said microorganism is genetically modified to overexpress at least one of YiaY, functional fragments, and functional mutants thereof having lactaldehyde reductase activity,
   wherein the YiaY, functional fragments, and functional mutants thereof having lactaldehyde reductase activity converts said (R), (S) and/or (R,S) lactaldehyde into 1, 2-propanediol, and
   b) recovering said 1,2-propanediol from the microorganism or cell culture medium.

2. The method according to claim 1, wherein YiaY has the sequence of SEQ ID NO: 3.

3. The method according to claim 1, wherein said recombinant microorganism is genetically modified to overexpress at least one enzyme selected from:
   methylglyoxal synthase;
   methylglyoxal reductase;
   glyoxalase;
   lactate dehydrogenase;
   lactate coA-transferase;
   lactoyl coA reductase; and
   any combination thereof.

4. The method according to claim 1, wherein said recombinant microorganism is selected from the group consisting of Enterobacteriaceae, Bacillaceae, Clostridiaceae, Streptomycetaceae and yeasts.

5. The method according to claim 4, wherein said Enterobacteriaceae is *Escherichia coli*.

* * * * *